US012673931B2

(12) United States Patent
Scarneo et al.

(10) Patent No.: US 12,673,931 B2
(45) Date of Patent: Jul. 7, 2026

(54) COMPOUNDS FOR DISEASE TREATMENT

(71) Applicant: Duke University, Durham, NC (US)

(72) Inventors: Scott Scarneo, Durham, NC (US); Philip F. Hughes, Durham, NC (US); Andrea Neely, Durham, NC (US); Timothy A.J. Haystead, Durham, NC (US)

(73) Assignee: Duke University, Durham, NC (US)

( * ) Notice: Subject to any disclaimer, the term of this patent is extended or adjusted under 35 U.S.C. 154(b) by 316 days.

(21) Appl. No.: 18/273,843

(22) PCT Filed: Jan. 25, 2022

(86) PCT No.: PCT/US2022/013742
§ 371 (c)(1),
(2) Date: Jul. 24, 2023

(87) PCT Pub. No.: WO2022/164822
PCT Pub. Date: Aug. 4, 2022

(65) Prior Publication Data

US 2024/0116893 A1 Apr. 11, 2024

Related U.S. Application Data

(60) Provisional application No. 63/141,794, filed on Jan. 26, 2021.

(51) Int. Cl.
*C07D 401/06* (2006.01)
*A61P 11/00* (2006.01)
(Continued)

(52) U.S. Cl.
CPC ............ *C07D 401/06* (2013.01); *A61P 11/00* (2018.01); *A61P 19/02* (2018.01); *A61P 25/02* (2018.01)

(58) Field of Classification Search
CPC ........ C07D 401/06; A61P 11/00; A61P 19/02; A61P 25/02
(Continued)

(56) References Cited

U.S. PATENT DOCUMENTS

2005/0203158 A1 9/2005 Bentzien et al.
2018/0105500 A1 4/2018 Derbyshire et al.

FOREIGN PATENT DOCUMENTS

WO 2004083854 A1 9/2004
WO 2020097398 A1 5/2020

OTHER PUBLICATIONS

Raphemot et al , Plasmodium PK9 Inhibitors Promote Growth of Liver Stage Parasites, Cell Chemical Biology (2019), 26(3), 411-419.e7). (Year: 2019).*

(Continued)

*Primary Examiner* — Taylor V Oh
(74) *Attorney, Agent, or Firm* — Polsinelli

(57) ABSTRACT

The present disclosure provides compounds according to Formula (I),

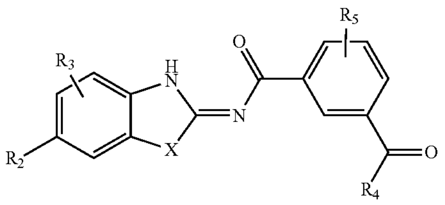

wherein X, $R_2$, $R_3$, $R_4$, and $R_5$ are defined herein. Further disclosed herein are pharmaceutical compositions, orally administrable dosage forms, and methods for using such compounds in the treatment of various (Continued)

diseases and disorders including inflammation, autoimmune disorders, chronic pain and cancer. In particular embodiments, the present disclosure provides orally bioavailable compounds capable of selectively modulating an activity (e.g., inhibition) of the serine/threonine protein kinase TAK1 and/or related kinases.

20 Claims, 15 Drawing Sheets

(51) Int. Cl.
*A61P 19/02* (2006.01)
*A61P 25/02* (2006.01)

(58) Field of Classification Search
USPC .......................................................... 514/322
See application file for complete search history.

(56) References Cited

OTHER PUBLICATIONS

Totzke et al. "Takinib, a Selective TAK1 Inhibitor, Broadens the Therapeutic Efficacy of TNF-a Inhibition for Cancer and Autoimmune Disease" Cell Chemical Biology, Aug. 17, 2017, vol. 24, pp. 1029-1039 1.

International Search Report and Written Opinion mailed Jun. 16, 2022 for PCT/US2022/013742 filed on Jan. 25, 2022 (Applicant—Duke University) (9 pages).

* cited by examiner

HS-276

Etanercept (Enbrel)

Methotrexate

Xeljanz (Tofacitinib)

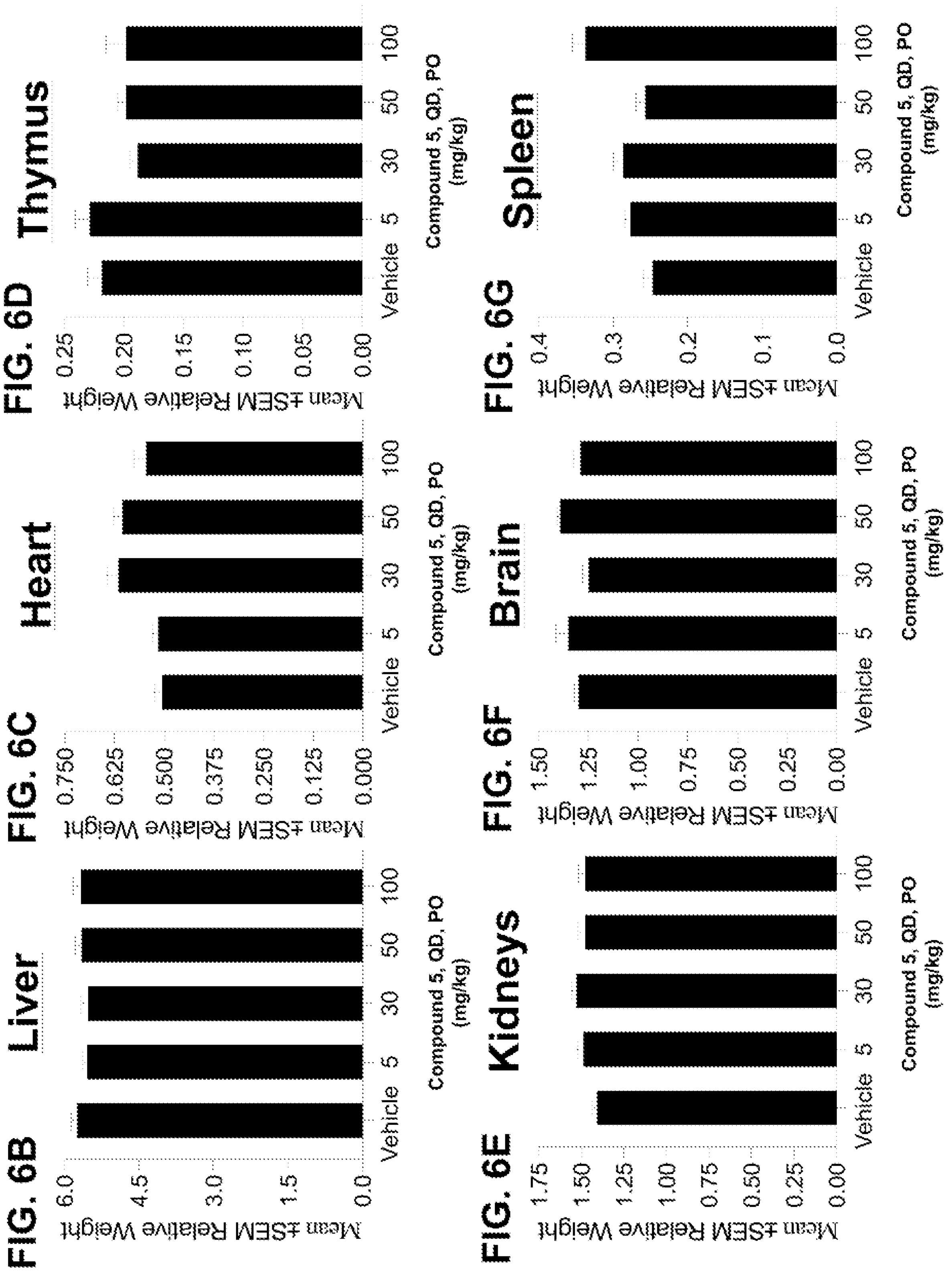
FIG. 6B
Liver
Mean ±SEM Relative Weight
6.0
4.5
3.0
1.5
0.0
Vehicle 5 30 50 100
Compound 5, QD, PO (mg/kg)
FIG. 6C
Heart
Mean ±SEM Relative Weight
0.750
0.625
0.500
0.375
0.250
0.125
0.000
Vehicle 5 30 50 100
Compound 5, QD, PO (mg/kg)
FIG. 6D
Thymus
Mean ±SEM Relative Weight
0.25
0.20
0.15
0.10
0.05
0.00
Vehicle 5 30 50 100
Compound 5, QD, PO (mg/kg)
FIG. 6E
Kidneys
Mean ±SEM Relative Weight
1.75
1.50
1.25
1.00
0.75
0.50
0.25
0.00
Vehicle 5 30 50 100
Compound 5, QD, PO (mg/kg)
FIG. 6F
Brain
Mean ±SEM Relative Weight
1.50
1.25
1.00
0.75
0.50
0.25
0.00
Vehicle 5 30 50 100
Compound 5, QD, PO (mg/kg)
FIG. 6G
Spleen
Mean ±SEM Relative Weight
0.4
0.3
0.2
0.1
0.0
Vehicle 5 30 50 100
Compound 5, QD, PO (mg/kg)

Formula (I)

Formula (II)

COMPOUNDS FOR DISEASE TREATMENT

CROSS-REFERENCE TO RELATED APPLICATIONS

This application is a national phase application of International Application No. PCT/US2022/013742 filed Jan. 25, 2022, which claims the benefit of U.S. Provisional Application No. 63/141,794, filed Jan. 26, 2021, the contents of each are hereby incorporated by reference in their entirety.

STATEMENT REGARDING FEDERALLY SPONSORED RESEARCH

This invention was made with government support under AR076772 awarded by the National Institutes of Health. The government has certain rights in the invention.

BACKGROUND OF THE INVENTION

The development of orally bioavailable kinase inhibitors, particularly inhibitors of the serine/threonine protein kinase TAK1 (also referred to herein as TGF-β-activated protein kinase 1 or MAPK3K7), has been a major research effort for many years. However, none of the previously described TAK1 inhibitors have been advanced clinically, largely due to selectivity issues in vivo and poor oral bioavailability.

SUMMARY OF THE INVENTION

The present disclosure provides orally bioavailable TAK1 modulators, capable of selectively modulating (e.g., inhibiting) TAK1. In various aspects, the present disclosure provides a TAK modulator according to Formula (I):

(I)

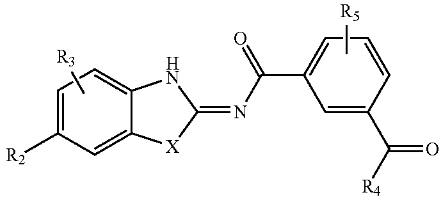

or a pharmaceutically acceptable salt, a tautomer, or a prodrug thereof, wherein; X is $NR_1$; $R_1$ is H, $C_{1-6}$ alkyl, $C_{1-6}$ carbonyl, $C_{1-6}$ carboxy, substituted or unsubstituted aryl, substituted or unsubstituted heteroaryl, substituted or unsubstituted cyclo($C_{3-8}$) alkyl, or substituted or unsubstituted heterocyclo($C_{3-8}$) alkyl; $R_2$ is $C_{1-6}$ alkyl, $C_{1-6}$ alkoxy, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6; $R_3$ is H, $C_{1-6}$ alkyl, $C_{1-6}$ alkoxy, halogen, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_8R_9$, $C_{1-6}$ alkyl-$NR_8R_9$, or $C_{1-6}$ alkoxy-$NR_8R_9$, wherein $R_8$ and $R_9$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_8$ and $R_9$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6; $R_4$ is OH, $C_{1-6}$ alkoxy, $NH_2$, NH($C_{1-6}$ alkyl), or N($C_{1-6}$ alkyl)($C_{1-6}$ alkyl); and $R_5$ is H, $C_{1-6}$ alkyl, $C_{1-6}$ alkoxy, or halogen; wherein the $C_{1-6}$ alkyl, $C_{1-6}$ alkoxy, $C_{1-6}$ carbonyl and $C_{1-6}$ carboxy of $R_1$, $R_2$, $R_3$, $R_4$, $R_5$, $R_6$, $R_7$, $R_8$, and $R_9$ are optionally and independently substituted by halo, OH, $NH_2$, NH($C_{1-6}$ alkyl), or N($C_{1-6}$ alkyl)($C_{1-6}$ alkyl). In some aspects, $R_4$ is $NH_2$. In some aspects, $R_5$ is H. In some aspects, $R_1$ is H, $C_{1-6}$ alkyl, or substituted or unsubstituted cyclo($C_{3-8}$) alkyl. In some aspects, $R_1$ is $C_{1-6}$ alkyl or substituted cyclohexyl. In some aspects, $R_3$ is H. In some aspects, $R_2$ is substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6. In some aspects, $R_2$ is —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring. In some aspects, $R_2$ is —$CH_2$—N($C_{1-6}$ alkyl)($C_{1-6}$ alkyl) or —$CH_2$—$NR_6R_7$, wherein $R_6$ and $R_7$ are combined with the nitrogen atom to form a 5-, 6-, 7- or 8-membered, substituted or unsubstituted heterocycloalkane or substituted or unsubstituted heteroaromatic ring. In some aspects, $R_2$ is —$CH_2$—$NR_6R_7$, wherein $R_6$ and $R_7$ are combined with the nitrogen atom to form a 5- or 6-membered, substituted or unsubstituted heterocycloalkane or substituted or unsubstituted heteroaromatic ring. In some aspects, $R_2$ is —$CH_2$—$NR_6R_7$, wherein $R_6$ and $R_7$ are combined with the nitrogen atom to form a 6-membered, substituted or unsubstituted heterocycloalkane ring. In some aspects, $R_2$ is substituted or unsubstituted piperidinomethyl. In some aspects, the compound according to Formula (I) is selected from the group consisting of

5

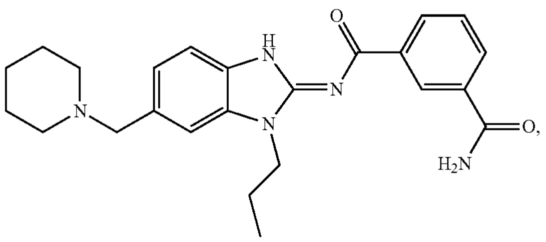

-continued

6

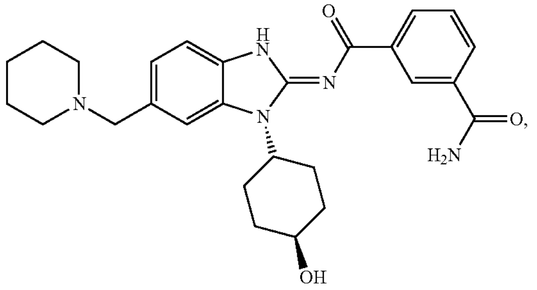

and

10

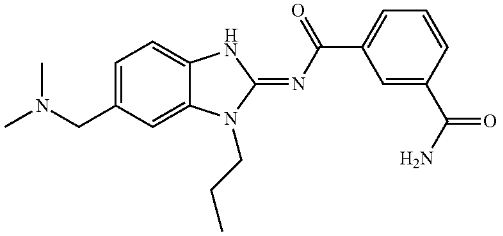

or a pharmaceutically acceptable salt, a tautomer, or a prodrug thereof. In some aspects, the compound according to Formula (I) is:

5

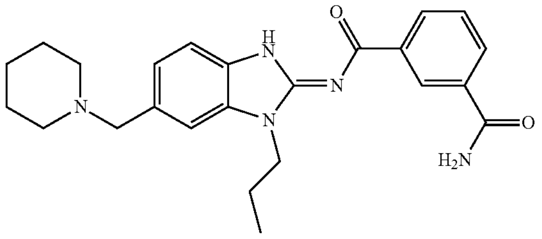

or a pharmaceutically acceptable salt, a tautomer, or a prodrug thereof.

In various aspects, provided herein is a compound according to Formula (II):

(II)

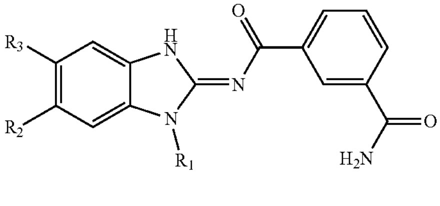

or a pharmaceutically acceptable salt, a tautomer, or a prodrug thereof, wherein $R_1$ is H, $C_{1-6}$ alkyl, $C_{1-6}$ carbonyl, $C_{1-6}$ carboxy, substituted or unsubstituted aryl, substituted or unsubstituted heteroaryl, substituted or unsubstituted cyclo ($C_{3-8}$) alkyl, or substituted or unsubstituted heterocyclo ($C_{3-8}$) alkyl; and $R_2$ and $R_3$ are independently selected from the group consisting of H, $C_{1-6}$ alkyl, $C_{1-6}$ alkoxy, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_4R_5$, $C_{1-6}$ alkyl-$NR_4R_5$, and $C_{1-6}$ alkoxy-$NR_4R_5$, wherein $R_4$ and $R_5$ are independently selected from the group consisting of H, $C_{1-6}$ alkyl, hetero-$C_{1-6}$ alkyl, substituted or unsubstituted aryl or substituted and unsubstituted aryl-$C_{1-6}$ alkyl; alternatively, $R_4$ and $R_5$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6, with the proviso that $R_2$ and $R_3$ are not simultaneously H; and wherein the $C_{1-6}$ alkyl and $C_{1-6}$ alkoxy of $R_1$, $R_2$, $R_3$, $R_4$, and $R_5$ are optionally and independently substituted by halo, OH, $NH_2$, NH($C_{1-6}$ alkyl), or N($C_{1-6}$ alkyl)($C_{1-6}$ alkyl). In some aspects, $R_1$ is H, $C_{1-6}$ alkyl, or substituted or unsubstituted cyclo($C_{3-8}$) alkyl. In some aspects, $R_1$ is $C_{1-6}$ alkyl or substituted or unsubstituted cyclo($C_{3-8}$) alkyl. In some aspects, $R_2$ is H and $R_3$ is —$CH_2$—$NR_6R_7$, and wherein $R_6$ and $R_7$ are combined with the nitrogen atom to form a 5-, 6-, 7- or 8-membered, substituted or unsubstituted heterocycloalkane or substituted or unsubstituted heteroaromatic ring. In some aspects, the compound according to Formula (II) is:

3

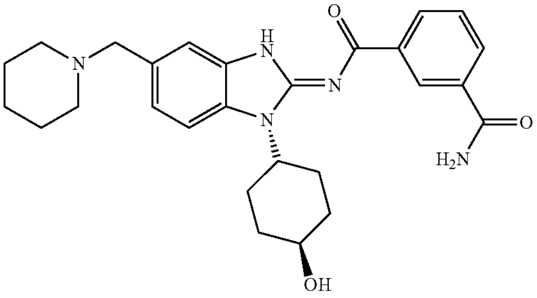

or

9

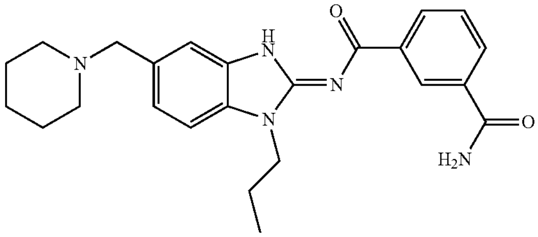

or a pharmaceutically acceptable salt, a tautomer, or a prodrug thereof. In some aspects, $R_3$ is H. In other aspects, $R_2$ is substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6. In some aspects, $R_2$ is —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring. In some aspects, $R_2$ is —$CH_2$—$N(C_{1-6}$ alkyl)($C_{1-6}$ alkyl) or —$CH_2$—$NR_6R_7$, wherein $R_6$ and $R_7$ are combined with the nitrogen atom to form a 5-, 6-, 7- or 8-membered, substituted or unsubstituted heterocycloalkane or substituted or unsubstituted heteroaromatic ring. In some aspects, $R_2$ is —$CH_2$—$NR_6R_7$, wherein $R_6$ and $R_7$ are combined with the nitrogen atom to form a 5- or 6-membered, substituted or unsubstituted heterocycloalkane or substituted or unsubstituted heteroaromatic ring. In some aspects, $R_2$ is —$CH_2$—$NR_6R_7$, wherein $R_6$ and $R_7$ are combined with the nitrogen atom to form a 6-membered, substituted or unsubstituted heterocycloalkane ring. In some aspects, $R_2$ is substituted or unsubstituted piperidinomethyl. In some aspects, the compound according to Formula (II) is selected from the group consisting of

2

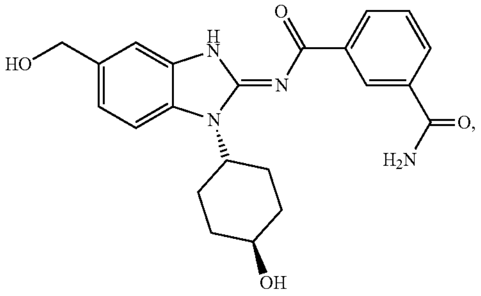

3

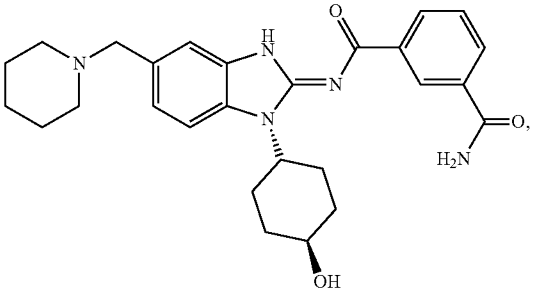

4

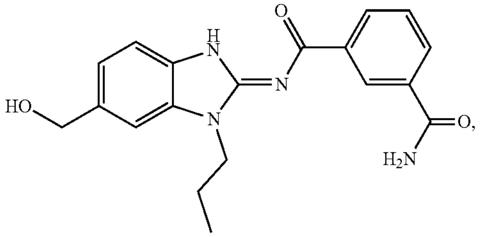

5

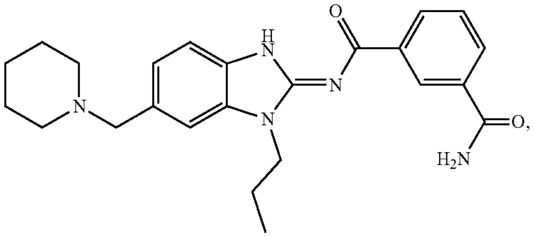

-continued

6

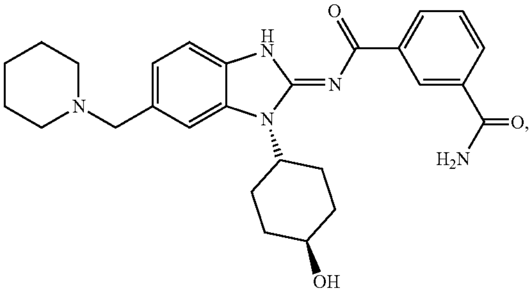

7

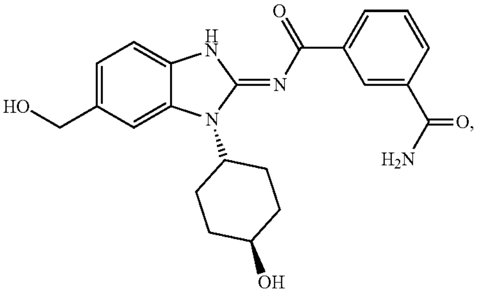

8

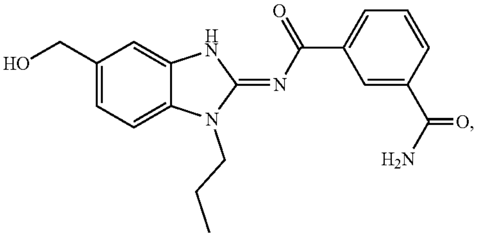

9

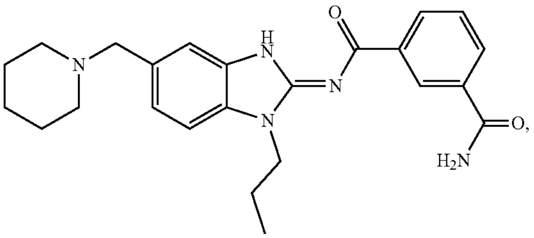

and

10

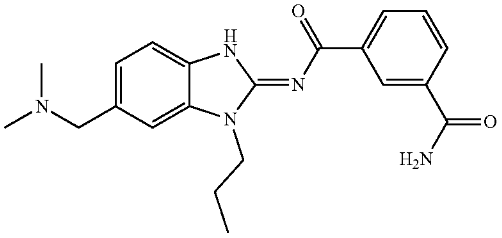

or a pharmaceutically acceptable salt, a tautomer, or a prodrug thereof. In some aspects, the compound according to Formula (II) is:

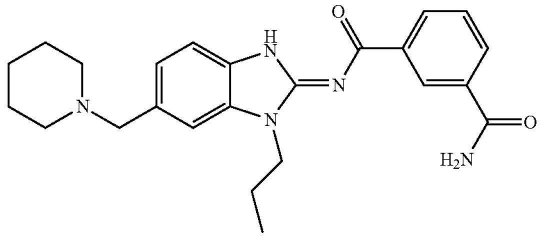

or a pharmaceutically acceptable salt, a tautomer, or a prodrug thereof.

In various aspects, provided herein is a pharmaceutical composition comprising a compound according the present disclosure, and a pharmaceutically acceptable carrier or excipient. In some aspects, the pharmaceutical composition is formulated into an oral dosage form. In some aspects, the oral dosage form is a solid oral dosage form. In some aspects, the solid oral dosage form is a capsule or a tablet.

In various aspects, further provided herein is a kit comprising a pharmaceutical composition of this disclosure that comprises a TAK1 modulator (e.g., TAK1 inhibitor), and instructions for treating a TAK1-mediated disease or disorder. In some aspects, the TAK1-mediated disease or disorder is an inflammatory condition, an autoimmune condition, or a cancer.

In various aspects, the present disclosure provides an oral dosage form comprising a compound according to the present disclosure. In some aspects, such oral dosage form is a tablet or a capsule.

In various aspects, provided herein is a compound capable of inhibiting TAK1 with a high selectivity over other kinases. In such aspects, the TAK1 inhibitor is a compound according to any one of Formulas (I)-(IV) having a ratio of $IC_{50}$ (IRAK) to $IC_{50}$ (TAK1) of at least about 25. In some instances, the ratio of $IC_{50}$ (IRAK) to $IC_{50}$ (TAK1) is at least about 50, 100, 500, 1,000, or 2,000. In some aspects, the IRAK is IRAK1 or IRAK4. In some aspects, the IRAK is IRAK4.

In various aspects, provided herein is a compound capable of selectively inhibiting TAK1 while being orally bioavailable. In such aspects, the TAK1 inhibitor is a compound according to any one of Formulas (I)-(IV) having a blood plasma concentration of at least about 0.25 μM measured 2 hours after oral administration of 50 mg/kg of the compound to a subject. In some instances, the blood plasma concentration is at least about 0.5, 1.0, or 1.5 μM.

Further provided herein is a method for modulating an activity of the serine/threonine protein kinase TAK1 in a subject in need thereof, the method comprising administering to the subject a pharmaceutical composition comprising an effective amount of a compound according to any one of Formulas (I)-(IV), thereby modulating the activity of the serine/threonine protein kinase TAK1. In some aspects, the activity of the serine/threonine protein kinase TAK1 is inhibited. In some aspects, the compound that inhibits TAK1 activity is any one of compounds 2-10 described herein. In some instances, the TAK1 inhibitor herein is compound 5.

Further provided herein is a method of treating a disease in a subject in need thereof, the method comprising administering to the subject a pharmaceutical composition comprising an effective amount of a compound according to any one of Formulas (I)-(IV). In some aspects, the disease is a TAK1-mediated disease. In some aspects, the disease is selected from the group consisting of an inflammatory disease, an autoimmune disease, and cancer. In some aspects, the disease is rheumatoid arthritis, osteoarthritis, gout, psoriatic arthritis, ankylosing spondylitis, diabetes, Sjogren's syndrome, lupus, inflammatory bowel disease, and psoriasis. In some aspects, the compound that is administered to the subject is any one of compounds 2-10. In some instances, the compound is compound 5. In some aspects, the compound is orally administered to the subject.

Further provided herein is a method of treating chronic pain in a subject in need thereof, the method comprising administering to the subject a pharmaceutical composition comprising an effective amount of a compound according to Formula (I):

(I)

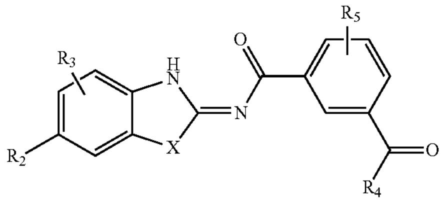

or a pharmaceutically acceptable salt, a tautomer, or a prodrug thereof, wherein X is $NR_1$; $R_1$ is H, $C_{1-6}$ alkyl, $C_{1-6}$ carbonyl, $C_{1-6}$ carboxy, substituted or unsubstituted aryl, substituted or unsubstituted heteroaryl, substituted or unsubstituted cyclo($C_{3-8}$) alkyl, or substituted or unsubstituted heterocyclo($C_{3-8}$) alkyl; $R_2$ is $C_{1-6}$ alkyl, $C_{1-6}$ alkoxy, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6; $R_3$ is H, $C_{1-6}$ alkyl, $C_{1-6}$ alkoxy, halogen, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_8R_9$, $C_{1-6}$ alkyl-$NR_8R_9$, or $C_{1-6}$ alkoxy-$NR_8R_9$, wherein $R_8$ and $R_9$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_8$ and $R_9$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6; $R_4$ is OH, $C_{1-6}$ alkoxy, $NH_2$, NH($C_{1-6}$ alkyl), or N($C_{1-6}$ alkyl)($C_{1-6}$ alkyl); and $R_5$ is H, $C_{1-6}$ alkyl, $C_{1-6}$ alkoxy, or halogen; wherein the $C_{1-6}$ alkyl, $C_{1-6}$ alkoxy, $C_{1-6}$ carbonyl and $C_{1-6}$ carboxy of $R_1$, $R_2$, $R_3$, $R_4$, $R_5$, $R_6$, $R_7$, $R_8$, and $R_9$ are optionally and independently substituted by halo, OH, $NH_2$, NH($C_{1-6}$ alkyl), or N($C_{1-6}$ alkyl)($C_{1-6}$ alkyl). In some aspects, the compound has a ratio of $IC_{50}$ (IRAK) to $IC_{50}$ (TAK1) of at least about 25, 50, 100, 500, 1,000 or 2,000. In some aspects, the IRAK is IRAK1 or IRAK4. In some aspects, the IRAK is IRAK4. In some aspects, the compound has a blood plasma concentration of at least about 0.25, 0.5, 1.0, or 1.5 μM measured 2 hours after oral administration of 50 mg/kg of the compound to a subject. In some aspects, the pharmaceutical composition is orally administered to the subject. In some aspects, the pharmaceutical composition is in the form of a tablet or a capsule. In some aspects, the pharmaceutical composition is orally administered to the subject at least once daily. In some aspects, the subject is treatment refractory to a previously administered anti-inflammatory agent. In some aspects, the anti-inflammatory agent is an anti-TNF biologic. In some aspects, the anti-TNF biologic is Enbrel®. In some aspects, the subject is a human or a rodent.

DESCRIPTION OF THE FIGURES

FIG. 1A shows that TAK1 was most potently inhibited by compound 5 with a half maximal inhibitory concentration ($IC_{50}$) value of 8 nM, 3.6-fold more potent than the next kinase CLK2 (29 nM), and 4.1-fold more potent than GCK (33 nM). Half maximal inhibitory concentrations of other kinases such as ULK2 (63 nM), MAP4K5 (124 nM), IRAK1 (264 nM), NUAK (270 nM), CSNK1G2 (809 nM), CAMKKβ-1 (1,280 nM) and MLK1 (5,585 nM) are also shown.

FIGS. 6B-6G show that daily dosing of compound 5 as described in FIG. 6A did also not cause a significant or dose-dependent change in relative weight of liver (FIG. 6B), heart (FIG. 6C), thymus (FIG. 6D), kidneys (FIG. 6E), brain (FIG. 6F), and spleen (FIG. 6G).

DETAILED DESCRIPTION

I. Introduction

Figure 1A:
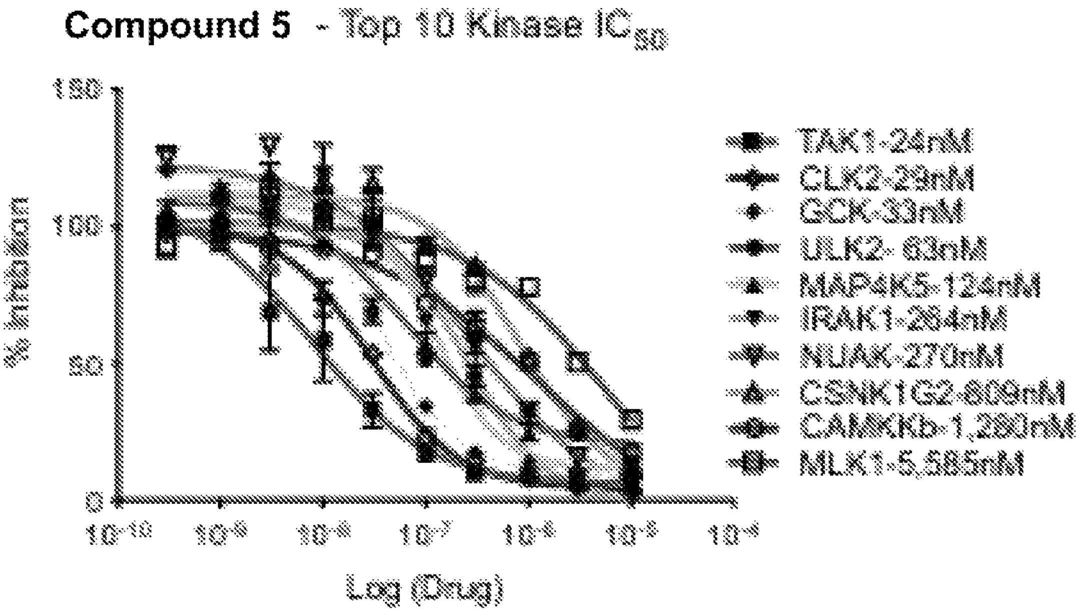
FIG. 1A shows percent inhibition of 10 selected kinases by compound 5 in a dose-response experiment. The top 10 kinases were selected based on results obtained from initial kinome screens.

The present disclosure provides orally bioavailable compounds capable of selectively modulating at least one kinase such as TAK1, as well as pharmaceutical compositions, orally administrable dosage forms, and methods for using the such compounds in the treatment of various diseases and disorders, e.g., TAK1-mediated diseases and disorders, including, but not limited to, inflammation, autoimmune disorders, chronic pain and cancer. In various embodiments, the present disclosure provides orally bioavailable, benzimidazole-derived compounds capable of selectively and potently modulating an activity of at least one kinase. Such kinase can be the serine/threonine protein kinase TAK1 (transforming growth factor (3-activated kinase 1). In other aspects, provided herein are compounds that can selectively and potently modulate an activity of at least two kinases. In some embodiments, such two kinases are TAK1 and an interleukin-1 receptor-associated kinase (IRAK). Such IRAK can be IRAK4.

Unless otherwise defined herein, all technical and scientific terms used herein have the same meaning as commonly understood by one of ordinary skill in the art. Furthermore, and for all compounds described herein, in the event the nomenclature is in conflict with the structure, it shall be understood that the compound is defined by the structure.

The terms "comprise(s)", "include(s)", "having", "has", "can", "contain(s)", and variants thereof, as used herein, are intended to be open-ended transitional phrases, terms, or words that do not preclude the possibility of additional acts, steps, or structures. The singular forms "a", "an" and "the" generally include plural references unless the context clearly dictates otherwise. The present disclosure also contemplates other embodiments "comprising", "consisting of" and "consisting essentially of", the embodiments or elements presented herein, whether explicitly set forth or not.

Section headings as used in this disclosure are not intended to be limiting.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

The term "about", as used herein, and unless clearly indicated otherwise, generally refers to and encompasses plus or minus 10% of the indicated numerical value(s). For example, "about 10%" may indicate a range of 9% to 11%, and "about 1" may include the range 0.9-1.1.

Compounds provided herein that contain one or more asymmetric carbon atoms may occur as racemates and racemic mixtures, single enantiomers, diastereomeric mixtures and individual diastereomers. All such isomeric forms of these compounds are expressly included in the present disclosure, unless otherwise stated. Each stereogenic carbon may be in the R or S configuration, or a combination of configurations.

Compounds provided herein can exist in more than one tautomeric form. For example, tautomeric forms of benzimidazole derivatives according to Formula (I) can be described as follows:

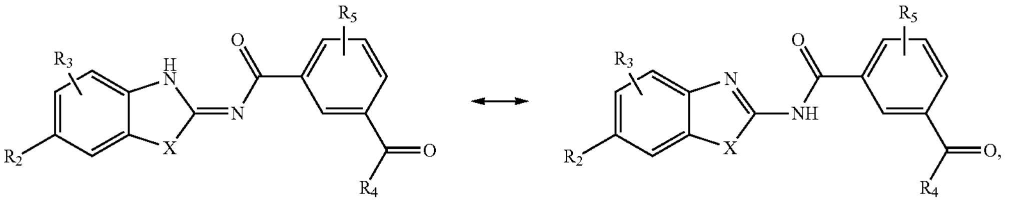

and other tautomers may be apparent to those of ordinary skill in the art, the present disclosure includes all such tautomers and methods of making and using the same.

For the description of chemical formulas, terms used herein may be preceded and/or followed by a single dash, "-", or a double dash, "=", to indicate the bond order of the bond between the named substituent and its parent moiety; in such instances, a single dash indicates a single bond and a double dash indicates a double bond. In the absence of a single or double dash it is generally understood that a single bond is formed between the substituent and its parent moiety.

The term "saturated", as used herein, generally refers to the referenced chemical structure that does not contain any multiple (e.g., double or triple) carbon-carbon bonds. For example, a saturated cycloalkyl group as defined herein includes cyclohexyl, cyclopropyl, and the like.

The term "unsaturated", as used herein, generally refers to the referenced chemical structure that contains at least one multiple (e.g., double or triple) carbon-carbon bond, but is generally not aromatic. For example, an unsaturated cycloalkyl group as defined herein includes cyclohexenyl, cyclopentenyl, cyclohexadienyl, and the like.

The term "heteroatom", as used herein, generally refers to an atom other than carbon, such as O, N, S, P, and Si.

As used herein, "nitrogen" and "sulfur" generally include any oxidized form of nitrogen and sulfur and the quarternized form of any basic nitrogen. For example, for an alkylthio radical such as —S—$C_{1-6}$ alkyl, unless otherwise specified, this shall be understood to include —S(O)—$C_{1-6}$ alkyl and —S($O_2$)—$C_{1-6}$ alkyl.

The term "alkenyl", as used herein, generally refers to a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy", as used herein, generally refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl", as used herein, generally refers to a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—, and the like.

The term "heteroalkyl", as used herein, generally refers to an alkyl, alkenyl or alkynyl group as defined herein, wherein at least one carbon atom of the alkyl group is replaced with a heteroatom. In some instances, heteroalkyl groups may contain from 1 to 18 non-hydrogen atoms (carbon and heteroatoms) in the chain, or from 1 to 12 non-hydrogen atoms, or from 1 to 6 non-hydrogen atoms, or from 1 to 4 non-hydrogen atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include, but are not limited to, alkoxyalkyl (e.g., methoxymethyl), and aminoalkyl (e.g., alkylaminoalkyl and dialkylaminoalkyl). Heteroalkyl groups may be optionally substituted with one or more substituents.

The term "alkylene", as used herein, generally refers to a bivalent alkyl group. An "alkylene chain" is a polymethylene group, i.e., —$(CH_2)_n$—, wherein n can be a positive integer, preferably from zero to six, from one to six, from one to four, from one to three, from one to two, or from two to three. Unless otherwise stated herein, an alkylene chain can be substituted or unsubstituted. A substituted alkylene chain is a polymethylene group in which one or more methylene hydrogen atoms is replaced with a substituent. Suitable substituents include those described below for a substituted aliphatic group. An alkylene chain may also be substituted at one or more positions with an aliphatic group or a substituted aliphatic group.

The term "alkynyl", as used herein, generally refers to a straight or branched chain hydrocarbon group containing from 2 to 10 carbon atoms, unless otherwise stated, and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, and unless specifically defined otherwise, generally refers to a phenyl (i.e., monocyclic aryl), or a bicyclic ring system containing at least one phenyl ring or an aromatic bicyclic ring containing only carbon atoms in the aromatic bicyclic ring system. For example, the bicyclic aryl can be azulenyl, naphthyl, or a phenyl fused to a monocyclic cycloalkyl, a monocyclic cycloalkenyl, or a monocyclic heterocyclyl. The bicyclic aryl can be attached to the parent molecular moiety through any carbon atom contained within the bicyclic system. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]-oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

An "aralkyl" or "arylalkyl" group, as used herein, generally comprises an aryl group covalently attached to an alkyl group, either of which independently is optionally substituted. Preferably, the aralkyl group is aryl-$C_{1-6}$ alkyl, including, without limitation, benzyl, phenethyl, and naphthylmethyl.

The term "cycloalkyl", as used herein, generally refers to a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form $-(CH_2)_w-$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The terms "halo" or "halogen", as used herein, generally refer to —F, —Cl, —Br, or —I. Thus, the terms "haloaliphatic", "haloalkyl", "haloalkenyl" and "haloalkoxy", for example, refer to an aliphatic, alkyl, alkenyl or alkoxy group, as the case may be, which is substituted with one or more halogen atoms.

The term "heteroaryl," as used herein, generally refers to a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The terms "heterocyclyl" and "heterocycloalkyl", as used herein, refer to a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring can contain 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothio-morpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydro-benzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term “potent”, as used herein in the context of a kinase-inhibiting compound, generally refers to a compound having a half maximal inhibitory concentration ($IC_{50}$) value of at most 1 μM for a specific kinase (e.g., TAK1, IRAKs, etc.) that this compound potently inhibits. In various instances, a compound described herein that is a potent inhibitor of a kinase has an $IC_{50}$ value for such kinase (e.g., TAK1 or IRAK) of at most about 1 μM, 500 nM, 250 nM, 100 nM, 50 nM, 25 nM or at most about 10 nM.

The terms “selective” or “kinase-selective”, as used herein in the context of a kinase-binding compound, generally refers to a compound that exhibits a high affinity for at least one kinase over other kinases from the mammalian (e.g., human) kinome. In some instances, “kinase-selectivity”, as used herein for a kinase-inhibiting compound, can be expressed as a ratio of $IC_{50}$ values. For example, a compound herein can be kinase-selective for a first kinase, kinase 1, over a second kinase, kinase 2, when the ratio ($IC_{50}$ (kinase 2))/($IC_{50}$ (kinase 1)) is at least about 25, 50, 100, 250, 500, 1,000, 1,500, 2,000, 2,500, or higher.

II. TAK1 Modulators

Provided herein are compounds capable of modulating an activity of a kinase. In various aspects, the compounds of the present disclosure are capable of inhibiting such kinase. Such kinase inhibition can be performed selectively, e.g., with a high selectivity for a specific kinase over one or more other kinases, e.g., one or more related or homogenous kinases.

The term “modulate”, as used herein in the context of kinase activity modulation, generally refers to the ability of a compound to increase or decrease the function and/or expression of a kinase, where kinase function may include kinase activity and/or protein-binding. Modulation may occur in vitro and/or in vivo. Modulation, as described herein, includes the inhibition or activation of kinase function and/or the downregulation or upregulation of kinase expression, either directly or indirectly. In various embodiments of the present disclosure, a kinase modulator compound of this disclosure can inhibit kinase function and/or downregulate kinase expression. The ability of such compound to inhibit kinase function can be demonstrated in an enzymatic assay or a cell-based assay as described elsewhere herein. In various embodiments, compounds of this disclosure are capbale of inhibiting TGF-β-activated protein kinase 1 (TAK1). In other instances, the kinase that can be inhibited by a compound of this disclosure is an interleukin-1 receptor-associated kinase (IRAK). In such cases, the IRAK can be IRAK4. In yet other embodiments, a compound described herein can inhibit both TAK1 and an IRAK (e.g., IRAK4).

In various embodiments, the present disclosure provides kinase inhibiting compounds according to the following Formula (I):

(I)

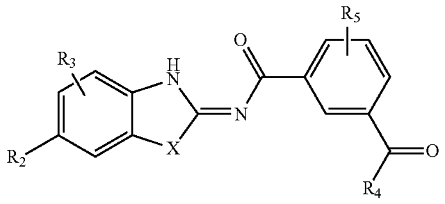

or a pharmaceutically acceptable salt, a tautomer, or a prodrug thereof, wherein X is $NR_1$; $R_1$ is H, $C_{1-6}$ alkyl, $C_{1-6}$ carbonyl, $C_{1-6}$ carboxy, substituted or unsubstituted aryl, substituted or unsubstituted heteroaryl, substituted or unsubstituted cyclo($C_{3-8}$) alkyl, or substituted or unsubstituted heterocyclo($C_{3-8}$) alkyl; $R_2$ is $C_{1-6}$ alkyl, $C_{1-6}$ alkoxy, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6; $R_3$ is H, $C_{1-6}$ alkyl, $C_{1-6}$ alkoxy, halogen, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_8R_9$, $C_{1-6}$ alkyl-$NR_8R_9$, or $C_{1-6}$ alkoxy-$NR_8R_9$, wherein $R_8$ and $R_9$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_8$ and $R_9$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6; $R_4$ is OH, $C_{1-6}$ alkoxy, $NH_2$, NH($C_{1-6}$ alkyl), or N($C_{1-6}$ alkyl)($C_{1-6}$ alkyl); and $R_5$ is H, $C_{1-6}$ alkyl, $C_{1-6}$ alkoxy, or halogen; wherein the $C_{1-6}$ alkyl, $C_{1-6}$ alkoxy, $C_{1-6}$ carbonyl and $C_{1-6}$ carboxy of $R_1$, $R_2$, $R_3$, $R_4$, $R_5$, $R_6$, $R_7$, $R_8$, and $R_9$ are optionally and independently substituted by halo, OH, $NH_2$, NH($C_{1-6}$ alkyl), or N($C_{1-6}$ alkyl)($C_{1-6}$ alkyl).

In some embodiments, a compound according to Formula (I) is capable of potently and selectively inhibiting at least one, at least two, or more kinases as further described herein. Such one or more kinases can belong to a mammalian kinome. In some cases, the one or more kinases belong to the human kinome. In some instances, a compound according to Formula (I) is capable of potently and selectively inhibiting one of a pair of two homologous kinases, or both homologous kinases. In some cases, such pair of two homologous kinases is the TAK1-IRAK4 pair.

In various embodiments, the present disclosure provides compounds capable of potently and selectively modulating TAK1. In such embodiments, a TAK1 modulator of this disclosure is a TAK1 inhibitor. In such cases, the TAK1 inhibitor is a compound according to Formula (I), wherein $R_4$ is $NH_2$. In some instances, $R_5$ is H. In yet other embodiments, $R_1$ is H, $C_{1-6}$ alkyl, or substituted or unsubstituted cyclo($C_{3-8}$) alkyl. In some aspects, $R_1$ is $C_{1-6}$ alkyl or substituted cyclohexyl. In some embodiments, $R_3$ is H.

In various aspects, a TAK1 inhibitor of the present disclosure is a compound according to Formula (I), wherein $R_2$ is a bulky substituent other than $CH_3$ or $OCH_3$. In such embodiment, $R_2$ can be substituted or unsubstituted $C_{2-6}$ alkyl, $C_{2-6}$ alkoxy, —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl, wherein Y is selected from the group consisting of a bond, O and S, and wherein the subscript n is an integer from 0 to 6; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring. In some instances, $R_2$ is —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring. In yet other instances, $R_2$ is —$CH_2$—N($C_{1-6}$ alkyl)($C_{1-6}$ alkyl) or —$CH_2$—$NR_6R_7$, wherein $R_6$ and $R_7$ are combined with the nitrogen atom to form a 5-, 6-, 7- or 8-membered, substituted or unsubstituted heterocycloalkane or substituted or unsubstituted heteroaromatic ring. In yet other instances, $R_2$ is —$CH_2$—$NR_6R_7$, wherein $R_6$ and $R_7$ are combined with the nitrogen atom to form a 5- or 6-membered, substituted or unsubstituted hetero-cycloalkane or substituted or unsubstituted heteroaromatic ring. In yet other instances, $R_2$ is —$CH_2$—$NR_6R_7$, wherein $R_6$ and $R_7$ are combined with the nitrogen atom to form a 6-membered, substituted or unsubstituted heterocycloalkane ring.

In some embodiments, $R_2$ is substituted or unsubstituted piperidinomethyl. In some case, $R_2$ is unsubstituted piperidinomethyl.

In various embodiments, a TAK1 inhibitor of the present disclosure is a compound according to Formula (I), and is selected from the group consisting of (compounds 2-10):

2

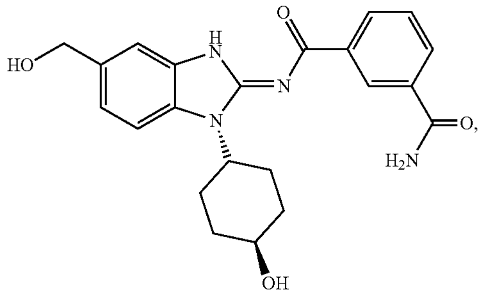

3

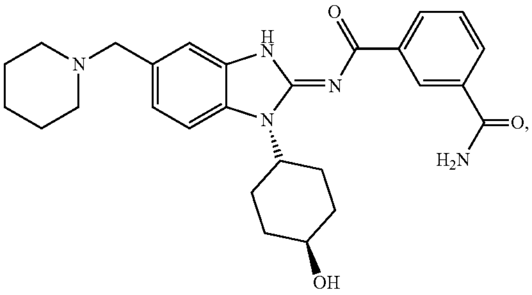

4

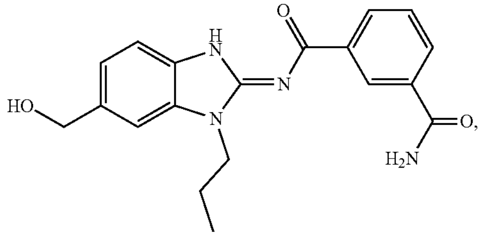

5

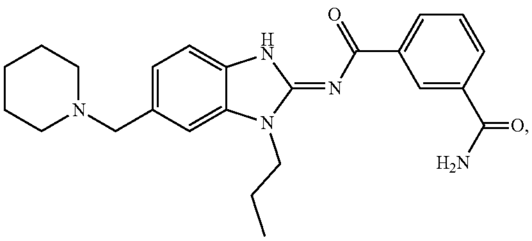

6

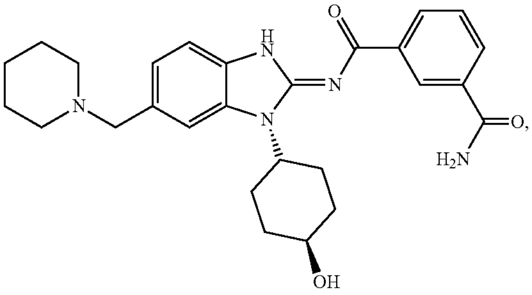

-continued

7

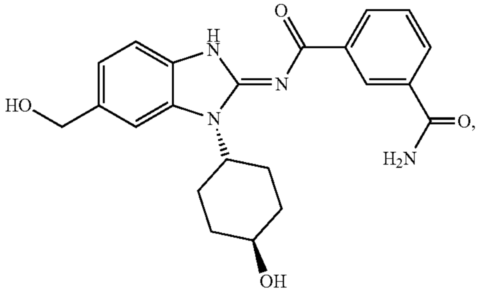

8

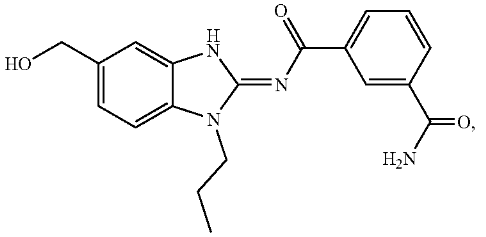

9

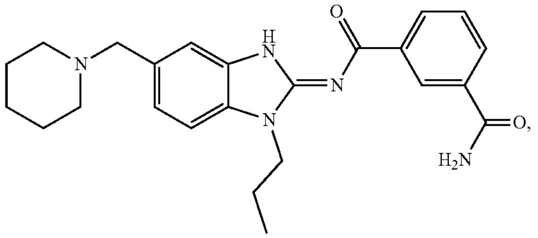

and

10

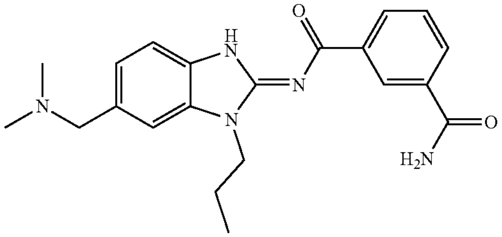

or a pharmaceutically acceptable salt, a tautomer, or a prodrug thereof.

In various embodiments, a TAK1 inhibitor of the present disclosure has a selectivity for TAK1 over an IRAK, wherein the TAK1-selectivity is expressed as a ratio of ($IC_{50}$ (IRAK))/($IC_{50}$ (TAK1)), and wherein such ratio is at least about 25. In various instances, the ratio of ($IC_{50}$ (IRAK))/($IC_{50}$ (TAK1)) is at least about 50, 100, 250, 500, 1,000, 1,500, 2,000, 2,500, or higher. In some cases, the IRAK is IRAK1 or IRAK4. In some cases, the IRAK is IRAK4. Hence, in some embodiments herein, a TAK1 inhibitor of the present disclosure has a selectivity for TAK1 over IRAK4, wherein the ratio of ($IC_{50}$ (IRAK4))/($IC_{50}$ (TAK1)) is at least about 25, 50, 100, 250, 500, 1,000, 1,500, 2,000, 2,500, or higher.

Surprisingly, it was found that introducing $R_2$ substituents that are larger and bulkier than H or $CH_3$ at the 1-position of the benzimidazole moiety (see, e.g., FIG. 8B, pos. 1) can drive selectivity of compounds herein towards TAK1 over homologous kinases, such as an IRAK, e.g., IRAK1 or IRAK4.

Thus, in some embodiments, $R_2$ is a larger and bulkier substituent than H or $CH_3$ as described herein, and $R_3$ is H.

In various embodiments, such TAK1 inhibitor of the present disclosure has a selectivity for TAK1 over IRAK4 of at least about 25. In some aspects, such compound is selected from the group consisting of:

5

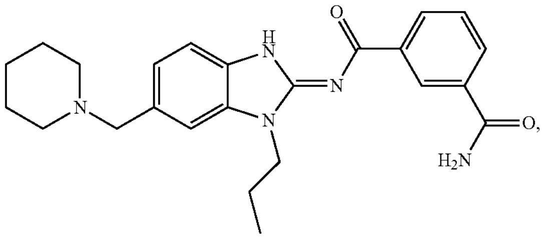

6

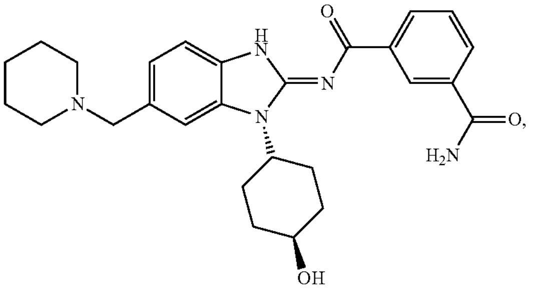

and

10

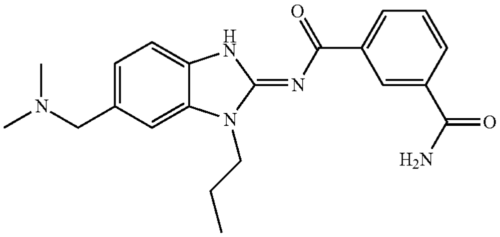

or a pharmaceutically acceptable salt, a tautomer, or a prodrug thereof.

In various embodiments, a TAK1 inhibitor of the present disclosure has a selectivity for TAK1 over IRAK4 of at least about 500. In some aspects, such compound is:

5

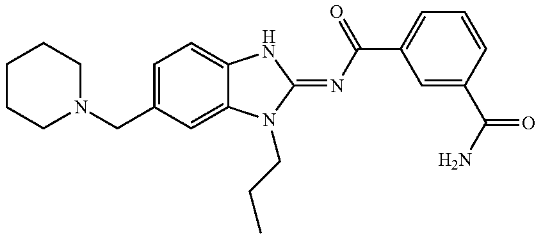

or a pharmaceutically acceptable salt, a tautomer, or a prodrug thereof.

In various embodiments, a TAK1 inhibitor of the present disclosure is a compound according to Formula (II):

(II)

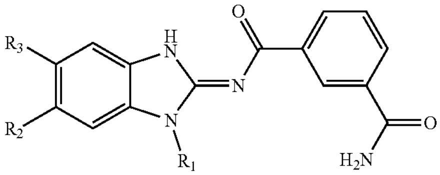

or a pharmaceutically acceptable salt, a tautomer, or a prodrug thereof, wherein $R_1$ is H, $C_{1-6}$ alkyl, $C_{1-6}$ carbonyl, $C_{1-6}$ carboxy, substituted or unsubstituted aryl, substituted or unsubstituted heteroaryl, substituted or unsubstituted cyclo ($C_{3-8}$) alkyl, or or substituted or unsubstituted heterocyclo ($C_{3-8}$) alkyl; and $R_2$ and $R_3$ are independently selected from the group consisting of H, $C_{1-6}$ alkyl, $C_{1-6}$ alkoxy, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_4R_5$, $C_{1-6}$ alkyl-$NR_4R_5$, and $C_{1-6}$ alkoxy-$NR_4R_5$, wherein $R_4$ and $R_5$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_4$ and $R_5$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6, with the proviso that $R_2$ and $R_3$ are not simultaneously H; wherein the $C_{1-6}$ alkyl and $C_{1-6}$ alkoxy of $R_1$, $R_2$, $R_3$, $R_4$, and $R_5$ are optionally and independently substituted by halo, OH, $NH_2$, NH($C_{1-6}$ alkyl), or N($C_{1-6}$ alkyl)($C_{1-6}$ alkyl).

In some embodiments, a TAK1 inhibitor is a compound according to Formula (II), wherein $R_1$ is H, $C_{1-6}$ alkyl, or substituted or unsubstituted cyclo($C_{3-8}$) alkyl. In some aspects, $R_1$ is $C_{1-6}$ alkyl or substituted or unsubstituted cyclo($C_{3-8}$) alkyl.

In various embodiments, a TAK1 inhibitor according to Formula (II) is selected from the group consisting of

2

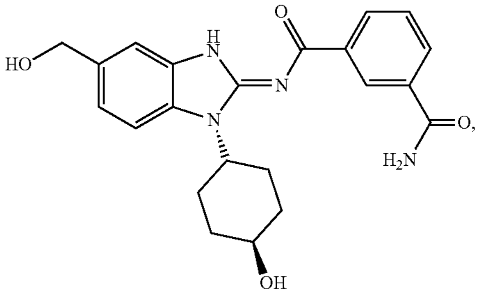

3

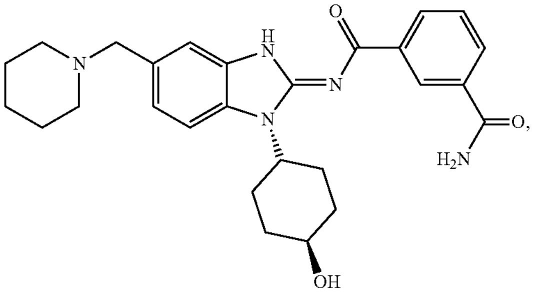

-continued

4

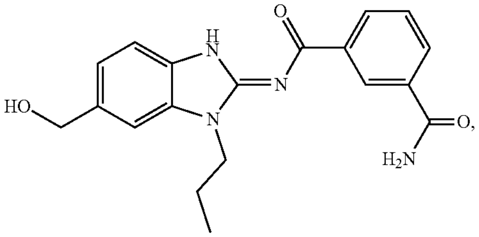

5

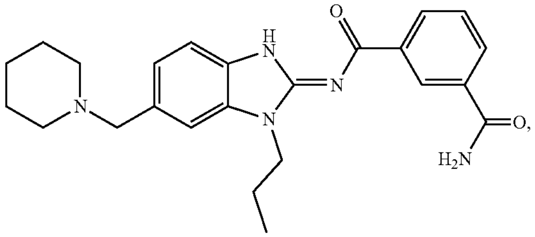

6

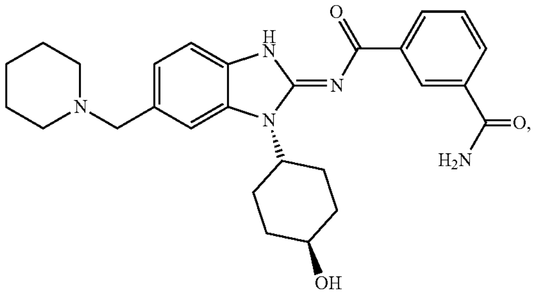

7

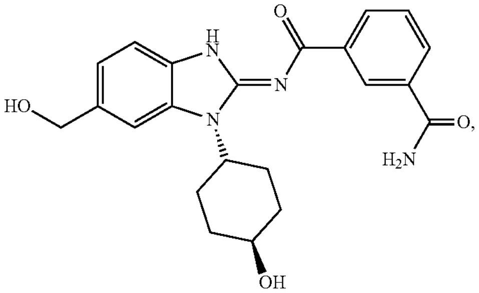

8

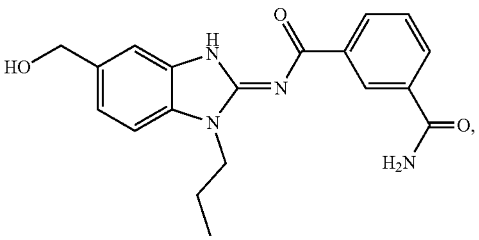

9

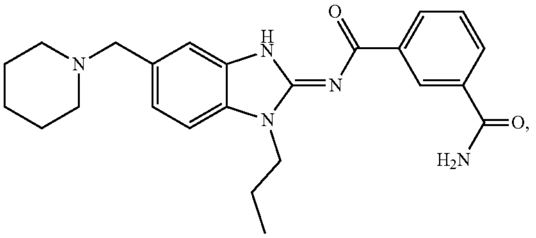

and

-continued

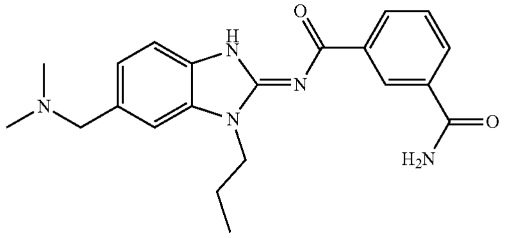

or a pharmaceutically acceptable salt, a tautomer, or a prodrug thereof.

In some embodiments, a TAK1 inhibitor according to Formula (II) has a selectivity for TAK1 over IRAK4, wherein the ratio of ($IC_{50}$ (IRAK4))/($IC_{50}$ (TAK1)) is at least about 25, 50, 100, 250, 500, 1,000, 1,500, 2,000, 2,500, or higher. In such instances, $R_3$ is H, according to Formula (III) below:

(III)

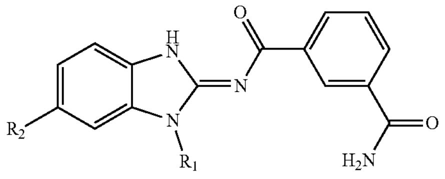

In further aspects, and with respect to Formula (III), $R_1$ can be $C_{1-6}$ alkyl or substituted or unsubstituted cyclo($C_{3-8}$) alkyl, and $R_2$ can be substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6. In some aspects, $R_2$ is —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring. In some aspects, $R_2$ is —$CH_2$—N($C_{1-6}$ alkyl)($C_{1-6}$ alkyl) or —$CH_2$—$NR_6R_7$, wherein $R_6$ and $R_7$ are combined with the nitrogen atom to form a 5-, 6-, 7- or 8-membered, substituted or unsubstituted heterocycloalkane or substituted or unsubstituted hetero-aromatic ring. In some aspects, $R_2$ is —$CH_2$—$NR_6R_7$, wherein $R_6$ and $R_7$ are combined with the nitrogen atom to form a 5- or 6-membered, substituted or unsubstituted heterocycloalkane or substituted or unsubstituted heteroaromatic ring. In some aspects, $R_2$ is —$CH_2$—$NR_6R_7$, wherein $R_6$ and $R_7$ are combined with the nitrogen atom to form a 6-membered, substituted or unsubstituted heterocycloalkane ring. In some aspects, $R_2$ is substituted or unsubstituted piperidinomethyl In some aspects, $R_2$ is unsubstituted piperidinomethyl. In such instances, a selective TAK1 inhibitor is:

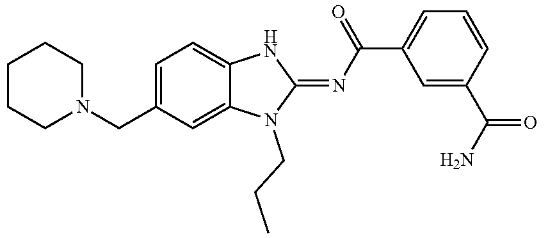

or

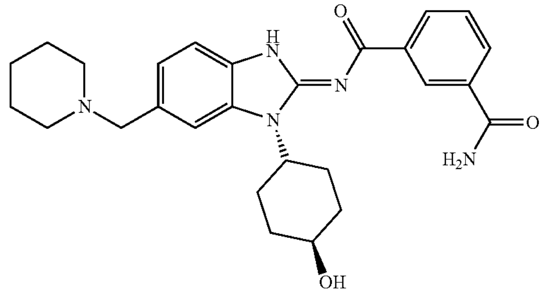

or a pharmaceutically acceptable salt, a tautomer, or a prodrug thereof.

In some aspects, the selective TAK1 inhibitor is:

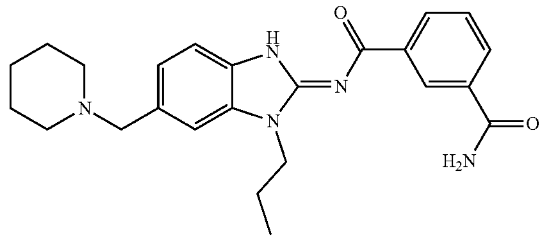

or a pharmaceutically acceptable salt, a tautomer, or a prodrug thereof.

In various aspects, provided herein are potent and selective TAK1 inhibitors according to Formula (I) or Formula (II) that are also orally bioavailable. In some instances, an orally bioavailable TAK1 inhibitor is a compound according to Formula (II). In some instances, an orally bioavailable TAK1 inhibitor can comprise a hydrophobic substituent at position N-7 of the benzimidazole (see, e.g., FIG. 8C, pos. 7). Such hydrophobic substituent can include any alkyl, cycloalkyl, or aryl groups, that can optionally be unsubstituted or substituted with one or more hydrophobic substituent(s).

In some embodiments, an orally bioavailable TAK1 inhibitor of the present disclosure can be characterized by a blood plasma concentration of at least about 0.25 μM measured 1, 2, 4, 8, and/or 12 hours after oral administration of 50 mg/kg of the compound to a subject. In some cases, an orally bioavailable TAK1 inhibitor of the present disclosure can have a blood plasma concentration of at least about 0.25 μM measured 1, 2, 4 and 8 hours after oral administration of 50 mg/kg of the compound to a subject. In some aspects, an orally bioavailable TAK1 inhibitor of the present disclosure can have a blood plasma concentration of at least about 0.25 μM measured 2 hours after oral administration of 50 mg/kg of the compound to a subject. In some aspects, an orally bioavailable TAK1 inhibitor of the present disclosure can have a blood plasma concentration of at least about 0.5, 0.75, 1.0, 1.25, 1.5, 1.75, or 2.0 μM measured 1, 2, 4 and/or 8 hours after oral administration of 50 mg/kg of the compound to a subject. In such cases, an orally bioavailable TAK1 inhibitor herein can have a blood plasma concentration of at least about 0.25, 0.5, 0.75, 1.0, 1.25, 1.5, 1.75, or 2.0 μM measured 2 or 4 hours after oral administration of 50 mg/kg of the compound to a subject. In some cases, the subject is a rodent. In other cases, the subject is a human.

In various aspects, an orally bioavailable TAK1 inhibitor herein can have a blood plasma concentration of at least about 0.25 μM measured 2 hours after oral administration of 50 mg/kg of the compound to a subject.

In some cases, the selective and orally bioavailable TAK1 inhibitor is:

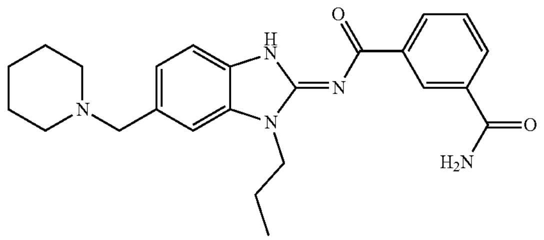

or a pharmaceutically acceptable salt, a tautomer, or a prodrug thereof.

A TAK1 inhibitor of the present disclosure, or a pharmaceutically acceptable salt thereof, can have a water solubility of at least about 5, 10, 20, 30, 40, 50, 60, 70, 100, 150, 200, or 250 mg/mL. In various instances, TAK1 inhibitor of the present disclosure, or a pharmaceutically acceptable salt thereof, can have a water solubility of at least about 50 mg/mL. In some instances, a water soluble TAK1 inhibitor of the present disclosure can be present as a pharmaceutically acceptable formate salt. In some aspects, a water soluble TAK1 inhibitor is a compound according to any one of Formulas (I)-(III). In some instances, a water soluble TAK1 inhibitor is a compound according to Formula (II), or a pharmaceutically acceptable formate salt thereof.

In various embodiments, the selective, orally bioavailable, or water soluble TAK1 inhibitor is:

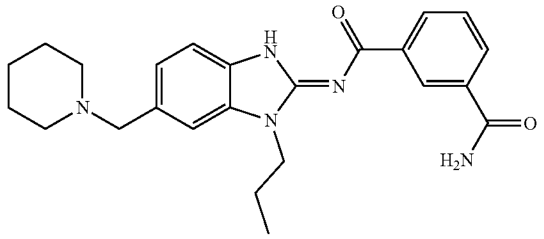

or a pharmaceutically acceptable salt (e.g., formate salt), a tautomer, or a prodrug thereof.

III. Dual-TAK1/IRAK Modulators

Further provided herein are compounds capable of inhibiting two or more kinases with $IC_{50}$ values in the low nanomolar ranges. In some instances, such dual-kinase inhibitors are capable of modulating two related or homologous kinases. Such a homologous pair of kinases can be the TAK1/IRAK4 pair. In such cases, a compound of the present disclosure can potently inhibit both TAK1 and IRAK4.

In various instances, a dual-TAK1/IRAK4 inhibitor can be a compound according to Formula (IV):

(IV)

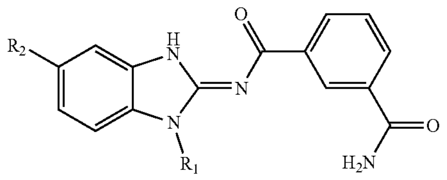

or a pharmaceutically acceptable salt, a tautomer, or a prodrug thereof, wherein $R_1$ is $C_{1-6}$ alkyl or substituted or unsubstituted cyclo($C_{3-8}$) alkyl, and $R_2$ is $C_{1-6}$ alkyl, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_3R_4$, $C_{1-6}$ alkyl-$NR_3R_4$, or $C_{1-6}$ alkoxy-$NR_3R_4$, wherein $R_3$ and $R_4$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_3$ and $R_4$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6. In some aspects, $R_2$ is —$NR_3R_4$, $C_{1-6}$ alkyl-$NR_3R_4$, or $C_{1-6}$ alkoxy-$NR_3R_4$, wherein $R_3$ and $R_4$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_3$ and $R_4$ may be combined with the nitrogen atom to form a 5-, 6-, 7- or 8-membered, substituted or unsubstituted heterocycloalkane or substituted or unsubstituted heteroaromatic ring. In some aspects, $R_2$ is —$CH_2$—N($C_{1-6}$ alkyl)($C_{1-6}$ alkyl) or —$CH_2$—$NR_3R_4$, wherein $R_3$ and $R_4$ are combined with the nitrogen atom to form a 5-, 6-, 7- or 8-membered, substituted or unsubstituted heterocycloalkane or substituted or unsubstituted hetero-aromatic ring. In some aspects, $R_2$ is —$CH_2$—$NR_3R_4$, wherein $R_3$ and $R_4$ are combined with the nitrogen atom to form a 5- or 6-membered, substituted or unsubstituted heterocycloalkane or substituted or unsubstituted heteroaromatic ring. In some aspects, $R_2$ is —$CH_2$—$NR_3R_4$, wherein $R_3$ and $R_4$ are combined with the nitrogen atom to form a 6-membered, substituted or unsubstituted heterocycloalkane ring. In some aspects, $R_2$ is substituted or unsubstituted piperidinomethyl.

In some aspects, $R_2$ is substituted or unsubstituted piperidinomethyl. In such instances, a dual-TAK1/IRAK4 inhibitor can be selected from:

3

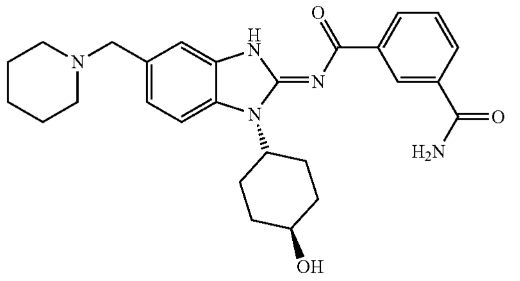

or

9

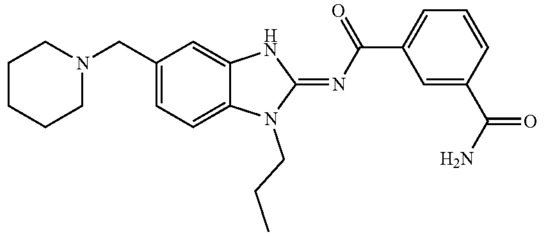

or a pharmaceutically acceptable salt, a tautomer, or a prodrug thereof.

IV. Synthesis

Further provided herein are methods and processes for synthesizing the compounds of the present disclosure. In all schemes, and unless otherwise specified, R substituents in the formulas shall have the meaning of the R substituents in Formula (I) as described throughout the present disclosure. Synthetic routes to exemplary compounds described herein are presented in EXAMPLES 1-4 below.

In some embodiments, a compound of the present disclosure can be prepared as shown below in exemplary SCHEME 1:

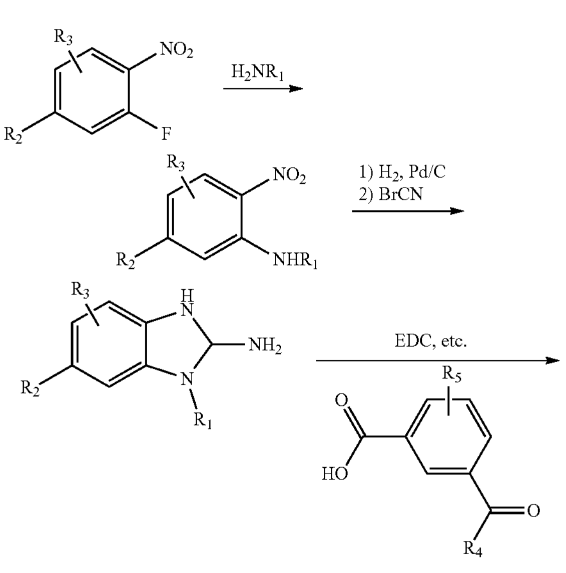

-continued

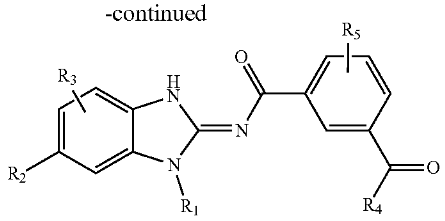

One of skill in the art may appreciate that the substituents (e.g., $R_1$, $R_2$, $R_3$, $R_4$, and $R_5$, etc.) can be altered before, during or after preparation of the heterocyclic scaffolding and that suitable adjustments in the exemplary conditions (e.g., temperatures, solvents, etc.) can be made. Additionally, one of skill in the art may recognize that protecting groups may be necessary for the preparation of certain compounds and may be aware of those conditions compatible with a selected protecting group.

V. Pharmaceutical Compositions and Dosage Forms

The present disclosure provides pharmaceutical compositions comprising a compound of the present disclosure and a pharmaceutically acceptable carrier and/or excipient. In various instances, such pharmaceutical compositions can be used to inhibit the kinase TAK1 in a subject, such as a rodent or a human.

The term "pharmaceutical composition", as used herein, is generally intended to encompass a product comprising the specified ingredients such as compounds, carriers, excipients, etc. (and in the specified amounts, if indicated), as well as any product which results, directly or indirectly, from combination of the specified ingredients in the specified amounts. The term "pharmaceutically acceptable" generally refers to a carrier or excipient that is compatible with the other ingredients of the formulation (e.g., active compound such as a TAK1 inhibitor) and not deleterious to the recipient thereof.

Thus, in some embodiments, the disclosure provides one or more compound(s) described herein (e.g., TAK1 inhibitor(s)) combined with a pharmaceutically acceptable excipient such as sterile saline, methylcellulose solutions, detergent solutions or other medium, water, gelatin, oils, etc. The compounds or compositions may be administered alone or in combination with any convenient carrier, diluent, etc., and such administration may be provided in single or multiple dosages. Useful carriers include water soluble and water insoluble solids, fatty acids, micelles, inverse micelles, liposomes and semi-solid or liquid media, including aqueous solutions and non-toxic organic solvents. All of the above formulations may be treated with ultrasounds, stirred, mixed, high-shear mixed, heated, ground, milled, aerosolized, pulverized, lyophilized, etc. to form pharmaceutically acceptable compositions.

In some embodiments, a pharmaceutical composition herein can comprise a pharmaceutically acceptable derivative of any compound (e.g., a TAK1 inhibitor) described herein. Such "pharmaceutically acceptable derivative" generally refers to any pharmaceutically acceptable salt or ester of such compound, a pharmacologically active metabolite or pharmacologically active residue thereof, or any other compound which, upon administration to a subject, is capable of providing (directly or indirectly) a compound useful to exert a therapeutic effect, e.g., TAK1 modulation, in such subject.

In some embodiments, a pharmaceutical composition herein comprises a pharmaceutically acceptable salt of a compound (e.g., TAK1 inhibitor) of the present disclosure. The term “pharmaceutically acceptable salt(s)”, as used herein, generally refers to salt(s) of an active compounds provided herein (e.g., TAK1 inhibitor) which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the selected base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the selected acid, either neat or in a suitable inert solvent. Examples of pharmaceutically acceptable acid addition salts include those derived from inorganic acids such as hydrochloric, hydrobromic, nitric, carbonic, monohydrogencarbonic, phosphoric, monohydrogenphosphoric, dihydrogen-phosphoric, sulfuric, monohydrogensulfuric, hydriodic, or phosphorous acids and the like, as well as the salts derived from relatively nontoxic organic acids like formic, acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Other acids, such as oxalic acid, while they may not themselves be pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium salts and their mono-, di-, tri-, and tetra-alkyl derivatives, e.g., N—$(C_{1-4}\ alkyl)_4^+$ salts. Also included are salts of amino acids such as arginate and the like, and salts of organic acids like glucuronic or galacturonic acids and the like. Certain specific compounds of the present invention can contain both basic and acidic functionalities that allow the compounds to be converted into either base or acid addition salts.

In other embodiments, a pharmaceutical composition can comprise a compound of this disclosure in its neutral form. The neutral form of a compound herein may be regenerated by contacting the salt with a base or acid and isolating the parent compound in the conventional manner. The parent form of the compound can differ from the various salt forms in certain physical properties, such as solubility in polar solvents but otherwise the salts are equivalent to the parent form of the compound for the purposes of the present disclosure.

In some embodiments, a pharmaceutically acceptable derivative of a compound that is part of a pharmaceutical composition may be a prodrug. Prodrugs of the compounds described herein can be those compounds that readily undergo chemical changes under physiological conditions to provide the compounds of the present disclosure. For example, a prodrug can, upon administration to a subject (e.g., a rodent or a human), be enzymatically or chemically metabolized (e.g., hydrolyzed, oxidized, reduced, etc.) to a pharmacologically active metabolite, e.g., the compound of the present disclosure. Additionally, prodrugs can be converted to the compounds of the present invention by chemical or biochemical methods in an ex vivo environment. Prodrugs may be useful in instances where such prodrug may be easier to administer than the parent drug. They may, for instance, exhibit an increased bioavailability by oral administration compared to the parent drug. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the “prodrug”), but then is metabolically hydrolyzed to the carboxylic acid, the active entity.

The pharmaceutical compositions provided herein and that comprise a compound of the present disclosure (e.g., a TAK1 inhibitor) can be provided in unit dosage form for administration to a subject, and may be prepared by any of the methods well known in the art. Such methods can include the step of bringing the active ingredient (e.g., TAK1 inhibitor) into association with a carrier which constitutes one or more accessory ingredients. In general, the pharmaceutical compositions can be prepared by uniformly and intimately bringing the active ingredient into association with a liquid carrier or a finely divided solid carrier or both, and then, if necessary, shaping the product into the desired formulation. In a pharmaceutical composition provided herein, the active compound (e.g., TAK1 inhibitor) can be included in an amount sufficient to produce the biological and/or therapeutic effect (e.g., TAK1 inhibition and/or decrease of its expression).

The compounds of the present disclosure may be administered in any conventional dosage form as described herein and in any conventional manner. Routes of administration include, but are not limited to, intravenously, intramuscularly, subcutaneously, intrasynovially, by infusion, sublingually, transdermally, orally, topically, using skin patches, or by inhalation. In various embodiments, a pharmaceutical composition herein comprising a compound of the present disclosure can be administered orally due to high oral bioavailability of the compounds, and this can provide therapeutically effective in vivo concentrations (e.g., serum concentrations) in a subject in need thereof.

The pharmaceutical compositions comprising a compound of the present disclosure as the active ingredient may be in a form suitable for oral use and administration, for example, as tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets can contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use described herein may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

In some embodiments, aqueous suspensions containing a compound of this disclosure in admixture with excipients suitable for the manufacture of aqueous suspensions can be provided. Such excipients can be suspending agents, for example sodium carboxymethyl-cellulose, methylcellulose, hydroxy-propylmethylcellulose, sodium alginate, polyvinylpyrrolidone, gum tragacanth and gum acacia; dispersing or wetting agents may be a naturally occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

In some aspects, dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the present disclosure may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

In some embodiments, the pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and can therefore melt in the rectum to release the drug. Such materials include cocoa butter and polyethylene glycols.

For topical use, creams, ointments, jellies, solutions or suspensions, etc., containing the compounds of the present invention are employed. As used herein, topical application is also meant to include the use of mouthwashes and gargles.

In some embodiments, the pharmaceutical compositions of the present disclosure, and methods using the same, may further comprise other therapeutically active compounds as described elsewhere herein, which can include standard-of-care or frontline treatments used in the treatment or prevention of the pathological conditions described herein (e.g., TAK-mediated disease or condition).

VI. Methods of Use

Provided herein are methods for using the compounds (e.g., TAK1 inhibitors) of the present disclosure to treat a disease or disorder in a subject. The term "subject", as used herein, generally includes animals such as mammals, including, but not limited to, primates (e.g., humans, monkeys), cows, sheep, goats, horses, dogs, cats, rabbits, rodents (e.g., rats, mice and the like). In various embodiments, the subject to be treated with a compound of the present disclosure is a human or a rodent.

In various embodiments, the subject treated with a compound of the present disclosure can be refractory to one or more previous treatments with frontline or standard-of-care therapeutics. In various cases, a TAK1 inhibitor of the present disclosure can provide favorable responses (e.g., alleviation or abrogation of the disease and/or its attendant symptoms) in refractory subjects.

In various embodiments, and without being bound to any theory, the compounds provided herein can exert their anti-inflammatory potential by reducing or blocking cytokine release locally, e.g., in specific tissues or organs of a subject. In various instances, the cytokine can be a tumor necrosis factor (TNF), and compounds of the present disclosure can attenuate inflammation induced by aberrant TNF-mediated intracellular signaling. Thus, in various cases, a compound of this disclosure may not remove all TNF function(s) systemically, but rather exert local, reversible blockage of cytokine release where cytokine (e.g., TNF) function is upregulated relative to baseline cytokine levels. Such approach may include local and reversible cytokine blockage or reduction, which can be allowed to increase to endogenous, healthy levels following treatment.

Thus, in various aspects, provided herein are TAK1 inhibitors that are capable of reducing cytokine expression in vitro as well as in vivo, wherein the reduction in cytokine expression is compared to baseline cytokine expression levels. In some instances, a TAK1 inhibitor provided herein can reduce the expression of a cytokine by at least about 2-fold, 3-fold, 4-fold, 5-fold, 7-fold, 10-fold, 11-fold, 15-fold, 20-fold or more. In some instances, the cytokine which expression can be reduced by a compound of this disclosure can be a tumor necrosis factor (TNF), chemokine (C—C motif) ligand 1 (CCL1), chemokine (C—X—C motif) ligand 1 (CXCL1), C—X—C motif chemokine 11 (CXCL11), intercellular adhesion molecule 1 (ICAM-1), interleukin-1 beta (IL-1b), interleukin-6 (IL-6), macrophage migration inhibitory factor (MIF), or a combination thereof. In various instances, a compound of this disclosure can reduce TNF expression at least about 11-fold.

Diseases and disorders that can be treated using one or more compounds of the present disclosure can include TAK1-responsive as well as TAK1-mediated diseases and disorders as described herein. In various embodiments, such diseases and disorders can include, but are not limited to, inflammation, autoimmune diseases, cancer, and/or chronic pain.

As used herein, the term "TAK1-responsive disease or disorder" and related phrases and terms, generally refer to a disease or disorder that responds favorably to modulation of TAK1 activity. Favorable responses to TAK1 modulation include alleviation or abrogation of the disease and/or its attendant symptoms, inhibition of the disease, i.e., arrest or reduction of the development of the disease, or its clinical symptoms, and regression of the disease or its clinical symptoms. A TAK1-responsive disease or disorder may be completely or partially responsive to TAK1-modulation. A TAK1-responsive disease or disorder may be associated with inappropriate, e.g., less than or greater than normal, TAK1-activity. Inappropriate TAK1 functional activity might arise as the result of TAK1 expression in cells which normally do not express TAK1, decreased TAK1 expression (leading to, e.g., lipid and metabolic disorders and diseases) or increased TAK1 expression. In some instances, a TAK1-responsive disease or disorder herein is favorably responsive to TAK1 inhibition.

As used herein, the term "TAK1-mediated disease or disorder" and related phrases and terms, generally refer to a disease or disorder characterized by inappropriate, e.g., less than or greater than normal, TAK1 activity. Inappropriate TAK1 functional activity might arise as the result of TAK1 expression in cells which normally do not express TAK1, increased TAK1 expression or degree of intracellular activation (leading to, e.g., inflammatory and autoimmune disorders and diseases and cancer) or decreased TAK1 expression. A TAK1-mediated disease or disorder may be completely or partially mediated by inappropriate TAK1 functional activity. However, a TAK1-mediated disease or disorder is one in which modulation of TAK1 results in some effect on the underlying disease or disorder. In some aspects, a TAK1-mediated disease or disorder can be characterized by greater than normal TAK1 activity. In such instances, TAK1 inhibition using a compound of the present disclosure can result in at least some improvement in patient well-being in at least some of the patients being treated with the TAK1 inhibitor.

Thus, the present disclosure provides methods for treating in a subject in need thereof a disease or disorder responsive to TAK1, and, in some cases TAK1 and/or IRAK modulation. Such methods can comprise administering to the subject in need thereof a therapeutically effective amount of a compound (e.g., TAK1 inhibitor) provided herein, e.g., a compound according to Formula (I). In various embodiments, such method comprises orally administering the compound provided herein capable of selectively modulating (e.g., inhibiting) TAK1 and/or IRAK4 as described herein.

As used herein, the terms "treat", "treating" and "treatment" generally refer to a method of alleviating or abrogating a disease and/or its attendant symptoms, and include a method of barring a subject from acquiring a disease and thus includes methods for reducing a subject's risk for acquiring a disease (e.g., prophylaxis). Furthermore, the term "therapeutically effective amount", as used herein, generally refers to the amount of a compound of the disclosure that can elicit the biological (e.g., TAK1 inhibition) or medical (e.g., alleviating or abrogating a disease) response of a tissue, system, animal or human that is being sought by the researcher, veterinarian, medical doctor or other clinician.

Examples of diseases and disorders that can be treated using the compounds of the present disclosure can include, but are not limited to inflammatory or allergic diseases such as systemic anaphylaxis or hypersensitivity responses, drug allergies, insect sting allergies and food allergies, inflammatory bowel diseases, such as Crohn's disease, ulcerative colitis, ileitis and enteritis, vaginitis, psoriasis and inflammatory dermatoses such as dermatitis, eczema, atopic dermatitis, allergic contact dermatitis, urticaria and pruritus, vasculitis, spondyloarthropathies, scleroderma, asthma and respiratory allergic diseases such as allergic asthma, allergic rhinitis, hypersensitivity lung diseases and the like, autoimmune diseases, such as arthritis (including rheumatoid and psoriatic), multiple sclerosis, systemic lupus erythematosus, type I diabetes, glomerulonephritis and the like, graft rejection (including allograft rejection and graft-v-host disease), other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, and cell proliferative or neoplastic diseases such as cancer, e.g., cancer of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, and diseases in which angiogenesis and neovascularization play a role.

In various embodiments, the present methods are directed to the treatment of diseases or disorders selected from rheumatoid (or inflammatory) arthritis, inflammatory bowel disease, systemic lupus erythematosus, psoriasis, asthma, multiple sclerosis, graft rejection and sepsis. In various embodiments, the presently described compounds and methods using the same can be directed to the treatment of chronic pain in a subject in need thereof. In other cases, the compounds of the present disclosure can be used to treat a viral disease, such as viral-induced pulmonary hyperinflammation (e.g., those caused by SARS-associated coronaviruses).

Depending on the disease or disorder to be treated and the subject's condition, the compounds of the present disclosure may be administered by, e.g., oral, parenteral (e.g., intramuscular, intraperitoneal, intravenous, intracisternal injection or infusion, subcutaneous injection or implant), inhalation, nasal, vaginal, rectal, sublingual, or topical routes of administration as further described elsewhere herein, and may be formulated, alone or together, in suitable dosage unit formulations containing conventional non-toxic pharmaceutically acceptable carriers, adjuvants and vehicles appropriate for each route of administration. The present disclosure also contemplates administration of the described compounds in a depot formulation, in which the active ingredient is released over a defined time period.

In the treatment of inflammatory diseases and immune disorders or other diseases or disorders mediated by TAK1, IRAK (e.g., IRAK4), or a combination thereof, an appropriate dosage level can generally be from about 0.001 to about 100 mg per kg patient body weight per day, which can be administered in single or multiple doses. In some instances, the dosage level can be from about 0.01 to about 25 mg/kg per day, or from about 0.05 to about 10 mg/kg per day. A suitable dosage level may be from about 0.01 to about 25 mg/kg per day, from about 0.05 to about 10 mg/kg per day, or from about 0.1 to about 5 mg/kg per day. Within this range, the dosage may be from about 0.005 to about 0.05, from about 0.05 to about 0.5 or from about 0.5 to about 5.0 mg/kg per day. For oral administration, the compositions can be provided in the form of tablets or capsules containing from about 1.0 to about 1000 milligrams of the active compound, particularly about 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active compound for the symptomatic adjustment of the dosage to the patient to be treated. The compounds may be administered on a regimen of, for example, 1 to 4 times per day, e.g., once or twice per day. Such dosage regimens can include administration schedules over multiple consecutive or non-consecutive days, weeks, or months, e.g., administration for at least 1, 2, 3, 4, 5, 6, 7, 8, 9, 10, 15, 20, or 25 days, weeks, and/or months.

It can be understood, however, that the specific dose level and frequency of dosage for any particular patient may be varied and may depend upon a variety of factors including the activity of the specific compound of this disclosure that is being employed, the metabolic stability and length of action of that compound, the age, body weight, general health, sex, and diet of the subject, the mode and time of administration, rate of excretion, drug combination, the severity of the particular condition, and the host undergoing therapy.

In various embodiments, the compounds of the present invention can be combined with other compounds having related or complementary utilities to treat a TAK1- (and/or IRAK-) mediated inflammation, immunerelated condition and disease, including rheumatoid arthritis, inflammatory bowel disease, systemic lupus erythematosus, cancer, pain as well as the additional pathologies noted above. In some embodiments, such combination therapy is used in the treatment or prevention of a condition or disorder mediated by TAK1.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound can be used. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

The weight ratio of a presently disclosed compound to the second active ingredient that it is combined with can be varied and can depend upon the effective dose of each ingredient. Generally, an effective dose of each can be used. Thus, for example, when a compound of the present disclosure is combined with another agent, the weight ratio of a disclosed compound to the other agent can generally range from about 1000:1 to about 1:1000, preferably from about 200:1 to about 1:200. Combinations of a compound of the present disclosure and other active ingredients can generally also be within the aforementioned range, but in each case, an effective dose of each active ingredient may be used. In such combinations disclosed compounds and other active agents can be administered separately or in conjunction. In addition, the administration of one element can be prior to, concurrent to, or subsequent to the administration of other agent(s).

In certain embodiments, a presently disclosed compound and pharmaceutical compositions comprising such compound can be used in combination with an anti-cancer/chemotherapeutic agent. In other cases, a compound of the present disclosure and/or a pharmaceutical composition comprising such compound, can be used in combination with one or more therapeutic agent(s) used for the treatment of inflammatory, autoimmune, and pain related diseases and disorders.

In some embodiments, a compound of this disclosure can be used in combination with an inhibitor of a mammalian IRAK. Such IRAK inhibitor can be directed against any one or more of IRAK-1, IRAK-2, IRAK-3, and/or IRAK-4. Such IRAK inhibitor can comprise an amino-benzimidazole moiety, an imidazo[1,2-a]pyridine moiety, an imidazo[1,2-b]pyridazine moiety, or an indazole moiety. In some instances, the IRAK inhibitor is, without limitation, JH-X-119-01, JH-I-25, PF-06650833, PF-06426779, CA-4948, AZ1495, Ginsenoside Rb1, IRAK4-IN-1, IRAK4-IN-4, IRAK4-IN-6, IRAK4-IN-7, IRAK-4 protein kinase inhibitor 2, HS271, IRAK inhibitor 1, IRAK inhibitor 2, IRAK inhibitor 3, IRAK inhibitor 4, IRAK inhibitor 6, FRI0016 R835, or N-(2-Morpholinylethyl)-2-(3-nitrobenzoylamido)-benzimidazole.

In some embodiments, a compound of this disclosure can be used in combination with an inhibitor of a mammalian Janus kinase (JAK), e.g., JAK1, JAK2, JAK3, TYK2, and/or a signal transducer and activator of transcription (STAT) protein, and hence such compound can alter the JAK/STAT pathway. Such JAK/STAT inhibitors can include, without limitation, tofacinib, ruxolitinib, oclacitinib, baricitinib, peficitinib, fedratinib, upadacitinib, filgotinib, cerdulatinib, gandotinib, lestaurtinib, momelotinib, pacritinib, abrocitinib, decernotinib, solcitinib, itacitinib, SHR0302, BMS-986165, BMS-911543, PF-04965842, CYT387, TG101348, AZD1480, AZC4205, R348, VX-509, GLPG0634, GSK2586184, AC-430, BP-1-102 tyrphostin AG 490, 2-naphthyl vinyl ketone, nifuroxazide, stattic, cryptotanshinone, S3I-201, niclosamide, diosgenin, icaritin, or 6-p-toluidino-2-naphthalenesulfonic acid.

In some embodiments, a compound of this disclosure can be used in combination with an anti-TNF compound. Such compounds can include small molecules, peptides, as well as proteins such as antibodies and binding fragments thereof. Therapeutic anti-TNF biologics that can be used in combination, can include afelimumab, certolizumab, etanercept, adalimumab, infliximab, and/or golimumab, or binding fragments thereof.

In some embodiments, a compound of this disclosure can be used in combination with small molecule therapeutics (e.g., anti-inflammatory agents) such as prednisone, methotrexate, hydroxychloroquine, leflunomide, sulfalazanine, ibuprofen, naproxen, ketoprofen, aspirin, meloxicam, celecoxib, indomethacin, tolmetin, etolodac, fenoprofen, and/or diclofenac.

VII. Methods for Evaluating TAK1 Modulators

Further provided herein are methods to evaluate putative specific agonists or antagonists of TAK1 (and/or an IRAK such as IRAK1 or IRAK4) function. Accordingly, the present disclosure is directed to the use of these compounds in the preparation and execution of screening assays for compounds which modulate the function of the TAK1 (and/or an IRAK, such as IRAK4). For example, the compounds of this disclosure can be useful for isolating receptor mutants, which are established screening tools for potent compounds. Furthermore, the compounds of this disclosure can be useful in establishing or determining of protein binding sites, geometry of potential binding pockets, as well as the binding site of other compounds to TAK1, e.g., by competitive inhibition. The compounds of the instant disclosure can also be useful for the evaluation of putative specific modulators of TAK1.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

Example 1

Synthesis of Compound 3

3

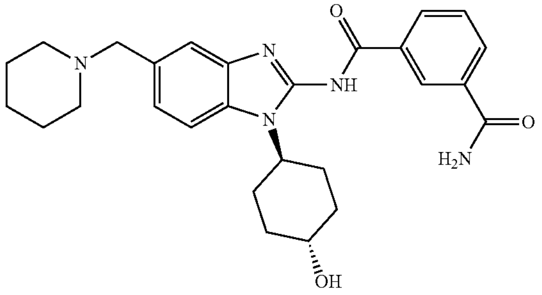

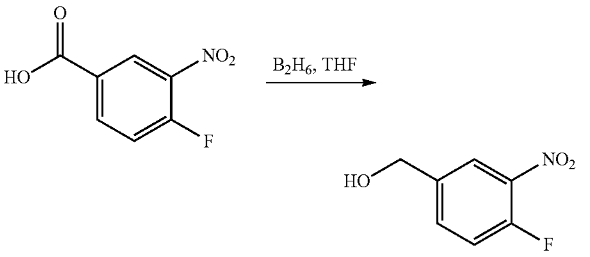

11

A solution of 4-fluoro-3-nitrobenzoic acid (4.35 g, 23.5 mmol) was slurried in THF (20 mL) and borane (1M in THF, 45 mL) was added dropwise. After stirring for 20 h, the reaction mixture was quenched by the slow addition of water (20 mL). The reaction mixture was then concentrated and partitioned between almost saturated sodium bicarbonate (100 mL) and ethyl acetate (200 mL). The organic layer was washed with brine (100 mL), dried ($MgSO_4$), and concentrated to give 11 (3.86 g, 96%) as a light tan oil. The oil crystalized over the weekend.

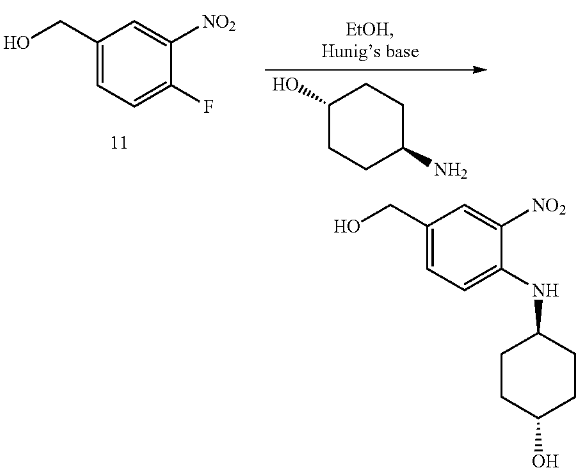

11

12

Alcohol 11 (3.5 g, 20.4 mmol) and trans-4-aminocyclohexanol (2.8 g, 24.5 mmol) were dissolved in ethanol (20 mL) and treated with Hunig's base (5.29 g, 7.1 mL, 40.9 mmol). The mixture was heated to 80° C. in a water bath for about 10 h, then allowed to cool and stir for 4 days. The mixture was concentrated, slurried in water and solid filtered off, washed with water and air-dried overnight to give 12 (3.74 g, 68%) as an orange powder.

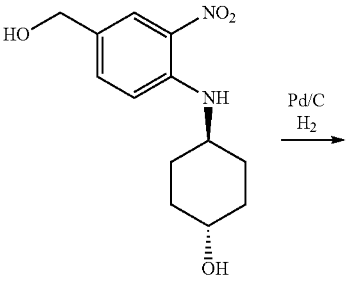

12

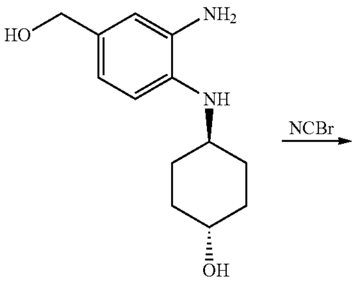

13

-continued

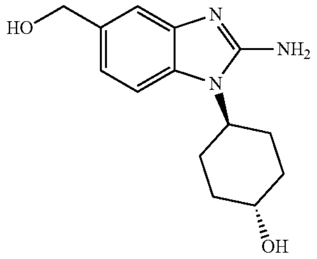

14

Alcohol 12 (1.2 g, 4.51 mmol) and 10% Pd/C (200 mg) were mixed in ethanol (100 mL) and vacuum/purged with hydrogen multiple times and stirred under a hydrogen atmosphere. After about 1.5 h, the orange color dissipated and TLC showed the reaction almost done. The reaction mixture was vacuum/argon purged multiple times, filtered through Celite and washed with more ethanol. The filtrate was treated with cyanogen bromide (1.1 g, 10.4 mmol) and stirred for 3 days. The reaction was concentrated to an oil, dissolved in DMSO and chromatographed (120 g isco C-18, 0 to 100% MeOH in 0.2% formic acid) to give product as a clear oil. The product was dissolved in water (~20 mL) and treated with 1N NaOH until the pH was around 12-13 which led to substantial precipitation. The solid was filtered off, washed with water and air-dried overnight to give 14 (443 mg, 37%) as a slightly mint colored powder; $^1$H-NMR (dmso-$d_6$) 7.24 (d, J=8 Hz, 1H), 7.06 (s, 1H), 6.78 (d, J=8 Hz, 1H), 6.23 (br s, 2H), 4.91 (t, J=5.7 Hz, 1H), 4.65 (d, J=4.4 Hz, 1H), 4.45 (d, J=5.7 Hz, 2H), 4.13 (tt, J=4, 12 Hz, 1H), 3.62 (m, 1H), 2.19 (dq, J=3, 12 Hz, 2H), 1.94 (d, J=12 Hz, 2H), 1.67 (d, J=12 Hz, 2H), 1.38 (dq, J=3, 12 Hz, 2H).

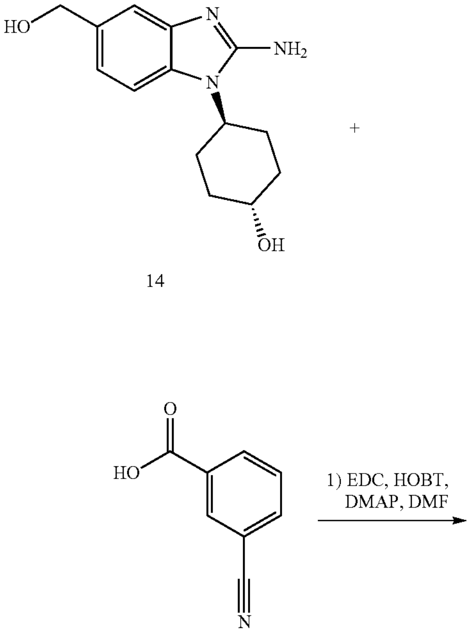

-continued

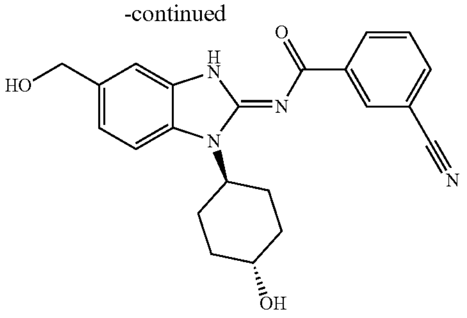

15

A mixture of 3-cyanobenzoic acid (100 mg, 680 μmol), compound 14 (178 mg, 680 mol), DMAP (20 mg, 140 μmol) and EDC (3.13 g, 16.3 mmol) were slurried in DMF (2 mL). Hunig's base (176 mg, 237 μL, 1.4 mmol) was added and the mixture stirred at RT for 18 h. The entire reaction mixture was added to a column and chromatographed (50 g isco C-18, 0 to 100% MeOH in 0.2% formic acid) to give 15 (75 mg, 28%) as a white powder. LC/MS gave a single peak with m/z=391.2 for $[M+H]^+$; $^1$H-NMR (dmso-$d_6$) 12.85 (s, 1H), 8.51 (d, J=8 Hz, 1H), 8.49 (s, 1H), 8.00 (d, J=8 Hz, 1H), 7.72 (t, J=8 Hz, 1H), 7.65 (d, J=8 Hz, 1H), 7.55 (s, 1H), 7.19 (d, J=8 Hz, 1H), 5.24 (br s, 1H), 4.81 (br t, J=12 Hz, 1H), 4.74 (br s, 1H), 4.55 (br s, 2H), 3.69 (m, 1H), 2.47 (m, 2H), 2.02 (br d, J=12 Hz, 2H), 1.79 (br d, J=12 Hz, 2H), 1.48 (br q, J=12 Hz, 2H).

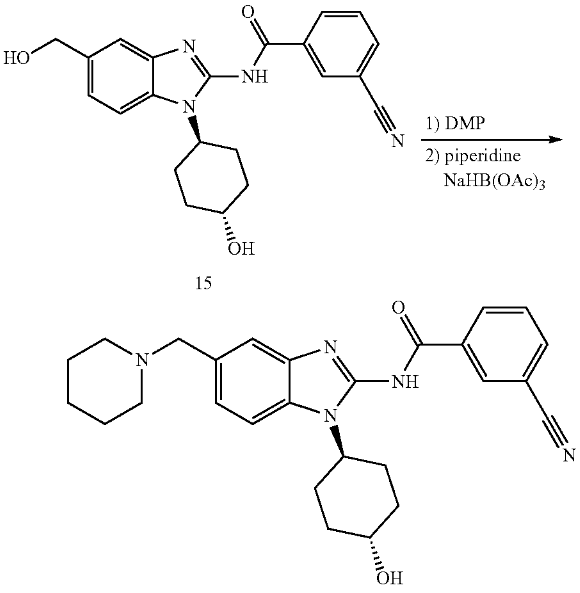

Alcohol 15 (70 mg, 179 μmol) was almost dissolved in methylene chloride (10 mL). Solid Dess-Martin periodinane (84 mg, 197 μmol) was added slowly as a powder. After stirring for 20 minutes, the mixture was then treated with piperidine (150 μL) and sodium triacetoxyborohydride (114 mg, 1.38 mmol) and stirred at RT overnight. The reaction mixture was homogenized by methanol addition and then concentrated. The residue was dissolved in DMSO and chromatographed (50 g isco C-18, 0 to 100% MeOH in 0.2% formic acid) to give 16 (50 mg, 55%) as a glass. LC/MS gave a single peak with m/z=458.3 for $[M+H]^+$; $^1$H-NMR (dmso-$d_6$) 12.83 (br s, 1H), 8.51 (d, J=8 Hz, 1H), 8.49 (s, 1H), 8.17 (s, 1H), 8.00 (d, J=8 Hz, 1H), 7.72 (t, J=8 Hz, 1H), 7.64 (d, J=8 Hz, 1H), 7.52 (s, 1H), 7.17 (d, J=8 Hz, 1H), 4.80 (br t, J=12 Hz, 1H), 3.68 (tt, J=4, 11 Hz, 1H), 3.51 (s, 2H), 2.46 (q, J=12 Hz, 2H), 2.36 (br s, 4H), 2.02 (br d, J=12 Hz, 2H), 1.79 (dr d, J=12 Hz, 2H), 1.43-1.54 (m, 6H), 1.40 (m, 2H).

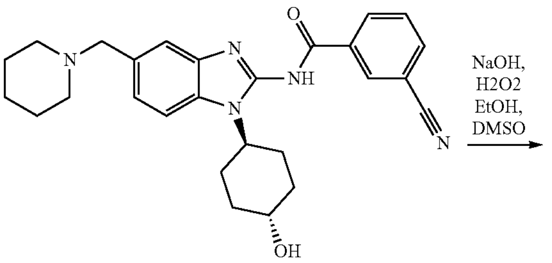

16

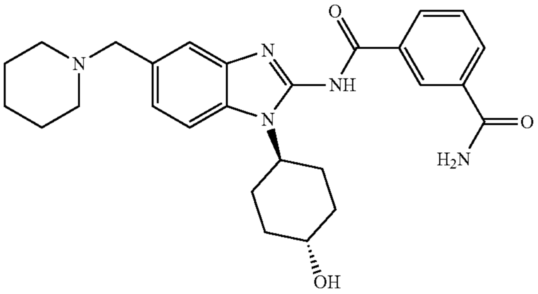

3

Nitrile 16 (65 mg, 142 μmol) was dissolved in ethanol (3 mL) and treated with dmso (3 drops) and 50% NaOH (4 drops) and 30% hydrogen peroxide (4 drops). After 50 m, TLC showed complete reaction. The mixture was treated with formic acid, concentrated and chromatographed (50 g isco C-18, 0 to 100% MeOH in 0.2% formic acid) to give a glass. Trituration with ethyl acetate gave compound 3 (39.8 mg, 54%) as a white powder. LC/MS shows a single peak at m/z=476.3 for $[M+H]^+$; $^1$H-NMR (dmso-$d_6$) 12.77 (br s, 1H), 8.67 (s, 1H), 8.53 (d, J=8 Hz, 1H), 8.18 (s, 1H), 8.10 (br s, 1H), 7.98 (d, J=8 Hz, 1H), 7.61 (d, J=8 Hz, 1H), 7.55 (t, J=8 Hz, 1H), 7.51 (s, 1H), 7.39 (br s, 1H), 7.16 (d, J=8 Hz, 1H), 4.79 (m, 1H), 3.70 (tt, J=4, 11 Hz, 1H), 3.51 (s, 2H), 2.48 (q, J=12 Hz, 2H), 2.36 (br s, 4H), 2.01 (br d, J=12 Hz, 2H), 1.79 (dr d, J=12 Hz, 2H), 1.36-1.53 (m, 8H).

Example 2

Synthesis of Compounds 4 and 5

4

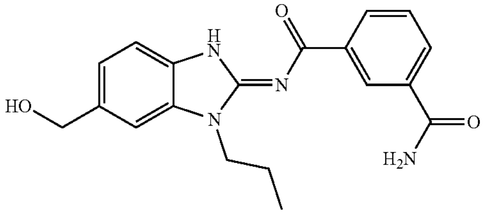

-continued

5

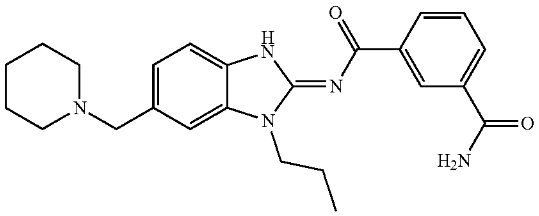

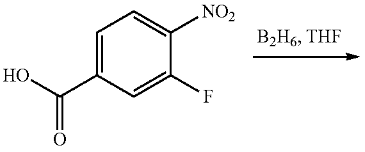

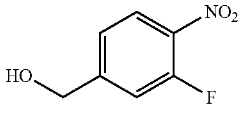

17

A solution of 3-fluoro-4-nitrobenzoic acid (12 g, 64.8 mmol) was slurried in THF (30 mL) and borane (1N in THF, 84.8 mL) was added dropwise and the mixture stirred at RT for 2 days. The reaction mixture was quenched with water (60 mL) and left to stir overnight. The next day, the mixture was concentrated to give a slurry of white solid. The slurry was diluted with water and stirred for 3 d. The slurry was filtered off, washed with water and and air-dried to give 17 (10.37 g, 93.5%) as an off-white crystalline solid.

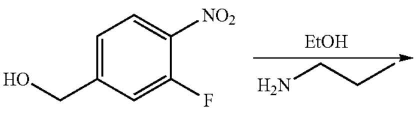

17

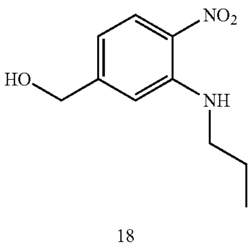

18

Benzyl alcohol 17 (3.92 g, 22.9 mmol) and n-propylamine (6.8 g, 9.4 mL, 115 mmol) were mixed in ethanol (20 mL) and heated to 70° C. in a water bath. After about an hour, the mixture was allowed to cool and stirred overnight. The next day, the mixture was treated with 1N NaOH (25 mL) and concentrated to an orange solid. The solid was triturated with water, filtered off and washed with water and air-dried to give 18 (4.72 g, 98%) as an orange solid.

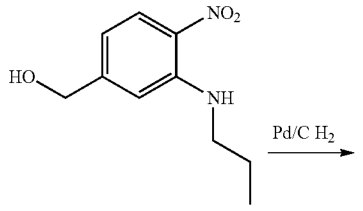

18

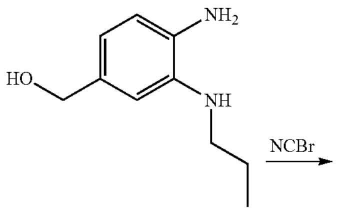

19

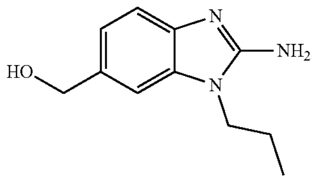

20

Alcohol 18 (1 g, 4.76 mmol) and 10% Pd/C (130 mg) were dissolved in ethanol (100 mL) and with vigorous stirring was vacuumed then purged with hydrogen twice and stirred under hydrogen. After 3 h, the orange color seemed to be gone giving 19 so the reaction was purged with nitrogen thrice and filtered through Celite and washed with more ethanol. The solution was then treated with solid cyanogen bromide (1.16 g, 10.9 mmol) and stirred overnight. The reaction mixture was concentrated and loaded onto a column with DMSO/water (the water was necessary) and chromatographed (120 g isco C-18, 0 to 100% MeOH in 0.2% formic acid) to give the formate salt as a white crystalline solid. The mixture was treated with 1N HCl (10 mL) and methanol and concentrated again to give a fluffy powder. The powder was scraped out to give 20 (887 mg, 77%) as a white solid. LC/MS gave a single peak with m/z=206.1 for $[M+H]^+$; $^1$H-NMR (dmso-$d_6$) 12.65 (s, 1H), 8.66 (s, 2H), 7.48 (s, 1H), 7.34 (d, J=8 Hz, 1H), 7.22 (d, J=8 Hz, 1H), 4.57 (s, 2H), 4.09 (t, J=7 Hz, 2H), 3.59 (v br s, $H_2O$), 1.71 (hex, J=7 Hz, 2H), 0.92 (t, J=7 Hz, 3H).

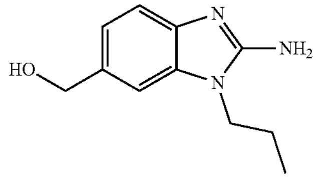
+

20

-continued

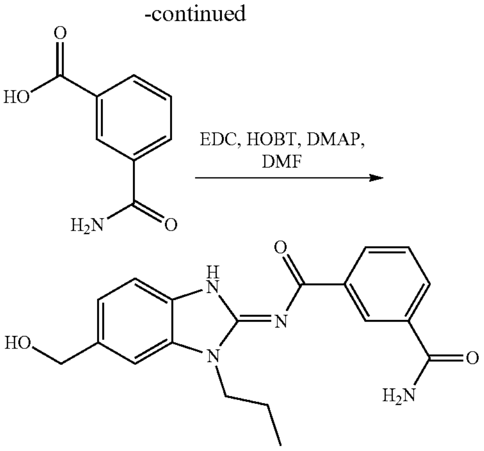

4

A mixture of 3-carbamoylbenzoic acid (205 mg, 1.24 mmol), HOBT (168 mg, 1.24 mmol), DMAP (30 mg, 248 μmol) and EDC (476 mg, 2.48 mmol) were slurried in DMF (4 mL). Hunig's base (321 mg, 432 μL, 2.48 mmol) was added and the mixture stirred at RT for 15 m. The mixture was then added dropwise to a solution of 20 (300 mg, 1.24 mmol) in DMF (2 mL). After 2 h, the reaction mixture was added to a column and chromatographed (120 g C-18 column, 0 to 100% MeOH in 0.2% formic acid) compound 4 (108 mg, 24%) as a flaky cream-colored solid. LC/MS gave a peak with m/z=353.2 for $[M+H]^+$; $^1$H-NMR (dmso-$d_6$) 12.71 (br s, 1H), 8.68 (s, 1H), 8.37 (d, J=8 Hz, 1H), 8.06 (br s, 1H), 7.98 (d, J=8 Hz, 1H), 7.54 (t, J=8 Hz, 1H), 7.48 (d, J=8 Hz, 1H) 7.47 (s, 1H), 7.40 (br s, 1H), 7.18 (d, J=8 Hz, 1H), 5.25 (t, J=4 Hz, 1H), 4.59 (d, J=4 Hz, 2H), 4.26 (t, J=7 Hz, 2H), 1.85 (hex, J=7 Hz, 2H), 0.94 (t, J=7 Hz, 3H).

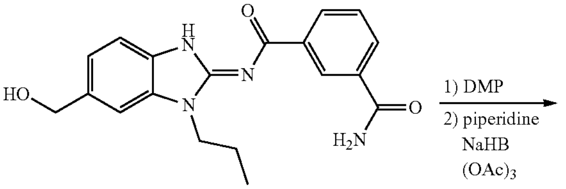

4

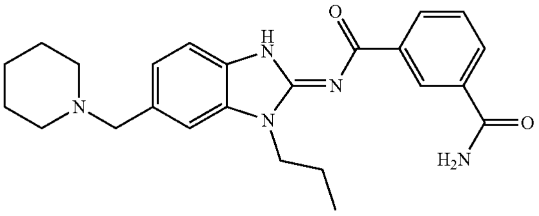

5

Compound 4 (93 mg, 264 μmol) was treated with water and DMF and concentrated to a dry powder to try to remove any possible methanol solvate. The residue was dissolved in DMF (1 mL). Solid Dess-Martin periodinane (DMP, 134 mg, 317 μmol) was added slowly as a powder. After stirring for 1 h, the mixture was then treated with piperidine (131 uL) and sodium triacetoxyborohydride (224 mg, 1.05 mmol) and stirred for a day. The next day, more DMP (100 mg) was added. After 1 h, more piperidine (131 μL), sodium triacetoxyborohydride (224 mg, 1.05 mmol) and DMF (1 mL) were added. After 2 h, the reaction mixture was added to a column and chromatographed (50 g C-18 column, 0 to 100% MeOH in 0.2% formic acid) to give the product as a glass which was triturated with ethyl acetate to give compound 5 (32 mg, 26%) as a cream colored solid. $^1$H-NMR (dmso-$d_6$) 12.70 (br s, 1H), 8.68 (s, 1H), 8.37 (d, J=8 Hz, 1H), 8.18 (s, 1H formic acid), 8.09 (br s, 1H), 7.98 (d, J=8 Hz, 1H), 7.54 (t, J=8 Hz, 1H), 7.47 (d, J=8 Hz, 1H), 7.42 (s, 1H), 7.40 (br s, 1H), 7.16 (d, J=8 Hz, 1H), 4.26 (t, J=7 Hz, 2H), 3.53 (s, 2H), 2.36 (m, 4H), 1.84 (hex, J=7 Hz, 2H), 1.50 (m, 4H), 1.39 (m, 2H), 0.94 (t, J=7 Hz, 3H).

Example 3

Synthesis of Compounds 6 and 7

6

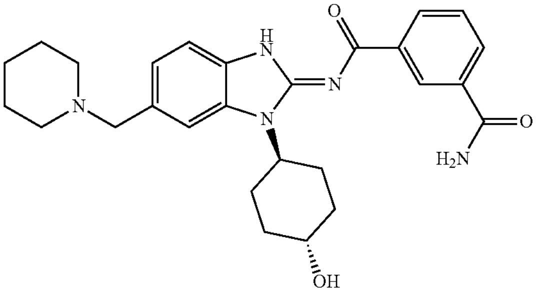

7

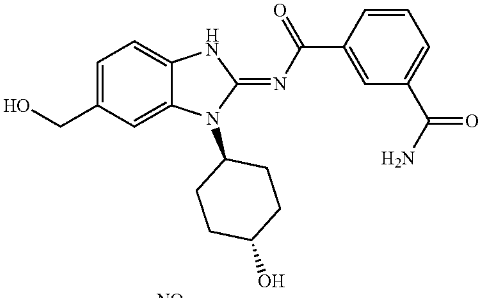

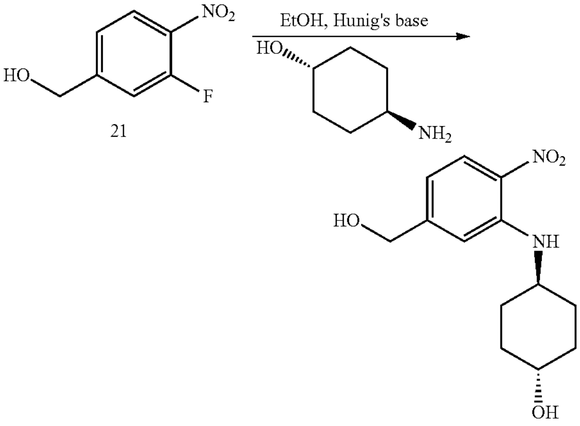

21

22

Nitro compound 21 (2 g, 11.7 mmol) and trans-4-amino-cyclohexanol (2.05 g, 18 mmol) were dissolved in ethanol (10 mL) and treated with Hunig's base (3 g, 4 mL, 23.4 mmol). The mixture was heated to 60° C. until starting material was consumed. The entire reaction was added to water (~100 mL) with rapid stirring. After about 2 h, the solid was filtered off, washed with water and air-dried to give 22 (2.58 g, 83%) as an orange powder. $^1$H-NMR (dmso-$d_6$) 8.00 (d, J=9 Hz, 1H), 8.00 (br d, J=7 Hz, 1H), 7.02 (s, 1H), 6.61 (d, J=9 Hz, 1H), 5.42 (t, J=6 Hz, 1H), 4.61 (d, 4 Hz, 1H), 4.51 (d, J=6 Hz, 2H), 3.57 (m, 1H), 3.49 (m, 1H), 2.01 (m, 2H), 1.84 (m, 2H), 1.30-1.43 (m, 4H).

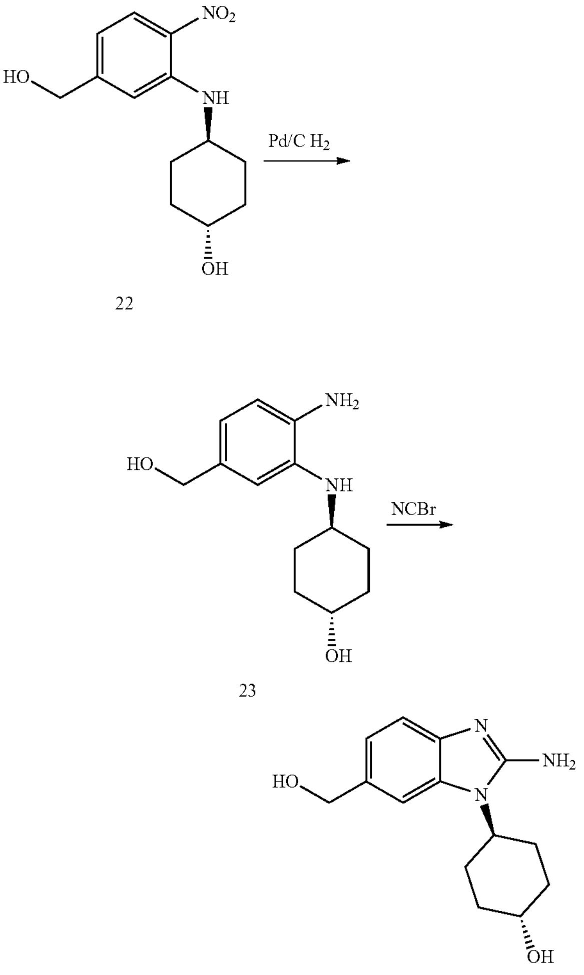

22

23

24

Nitro compound 22 (2 g, 7.51 mmol) and 10% Pd/C (400 mg) were dissolved in ethanol (200 mL) and with vigorous stirring was vacuumed then purged with nitrogen, then hydrogen thrice and stirred under a hydrogen atmosphere. At about 90 m, TLC showed essentially complete reaction to compound 23. The reaction mixture vacuum purged with nitrogen and was filtered through Celite. The filtrate was then treated with solid cyanogen bromide (1.8 g, 17.3 mmol) and stirred at RT for 4 days over which substantial solid formed. The solid was filtered off and washed with a little ethanol, then air-dried to give 24 (1.89 g, 73%), the HBr salt, as an off-white powder. The powder is water-soluble. $^1$H-NMR (dmso-$d_6$) 12.51 (br s, 1H), 8.47 (br s, 2H), 7.62 (s, 1H), 7.32 (d, J=8 Hz, 1H), 7.21 (d, J=8 Hz, 1H), 5.26 (br t, J=4 Hz, 1H), 4.76 (br d, 1H), 4.57 (d, J=4 Hz, 2H), 4.37 (tt, J=4, 12 Hz, 1H), 3.67 (m, 1H), 2.23 (dq, J=4, 12 Hz, 2H), 1.98 (br d, J=12 Hz, 2H), 1.81 (br d, J=12 Hz, 2H), 1.40 (br q, J=12 Hz, 2H).

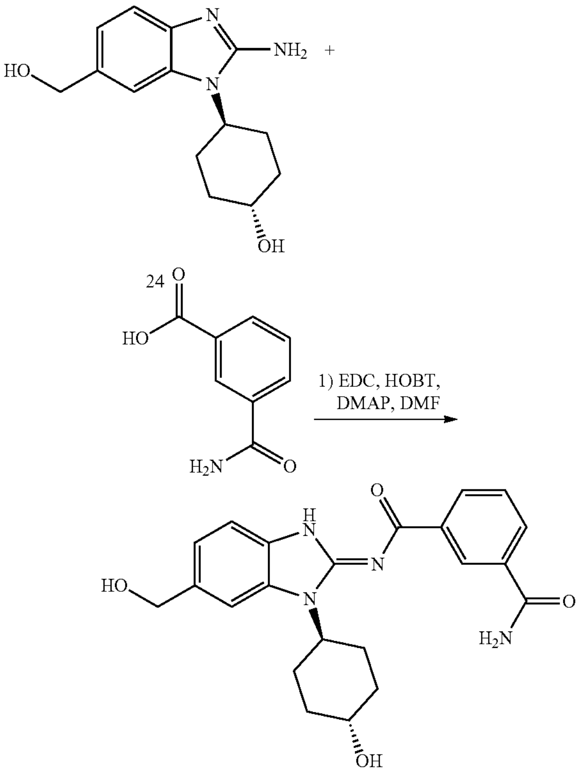

24

7

A mixture of 3-carbamoylbenzoic acid (290 mg, 1.75 mmol), alcohol 24 (500 mg, 1.46 mmol), HOBT (198 mg, 1.46 mmol), DMAP (36 mg, 292 μmol) and Hunig's base (566 mg, 763 L, 4.38 mmol) were slurried in DMF (10 mL). EDC (560 mg, 2.92 mmol) was added and the mixture stirred at RT for 1 d. The mixture was treated with 50% NaOH (15 drops) to cleave bis-acylated by-product and stirred overnight. The reaction mixture was then neutralized with acetic acid, concentrated and then chromatographed (120 g C-18, 0 to 100% MeOH in 0.2% formic acid) compound 7 (~310 mg, 48%) as a white solid. $^{1}$H-NMR (dmso-$d_6$) 12.78 (br s, 1H), 8.67 (s, 1H), 8.35 (d, J=7.5 Hz, 1H), 8.10 (br s, 1H), 7.98 (d, J=7.5 Hz, 1H), 7.60 (s, 1H), 7.55 (t, J=7.5 Hz, 1H), 7.50 (d, J=8 Hz, 1H), 7.39 (br s, 1H), 7.17 (d, J=8 Hz, 1H), 5.23 (t, J=6 Hz, 1H, —OH), 4.79 (br m, 1H), 4.74 (d, J=6 Hz, 1H, —OH), 4.59 (d, J=6 Hz, 2H), 4.09 (q, J=5 Hz, 1H, $CH_3$—OH), 3.71 (m, 1H), 3.71 (d, J=5 Hz, 3H, $CH_3$—OH), 2.53 (m, 2H), 2.03 (br d, J=11 Hz, 2H), 1.79 (br d, J=11 Hz, 2H), 1.48 (br q, J=11 Hz, 2H). Compound 7 can form a solvate with methanol.

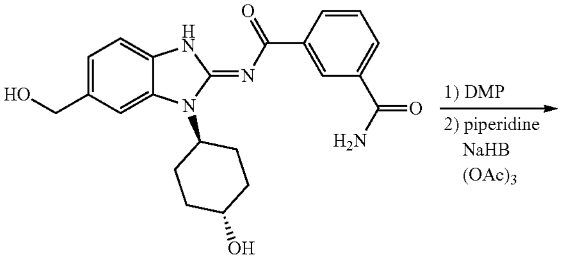

7

-continued

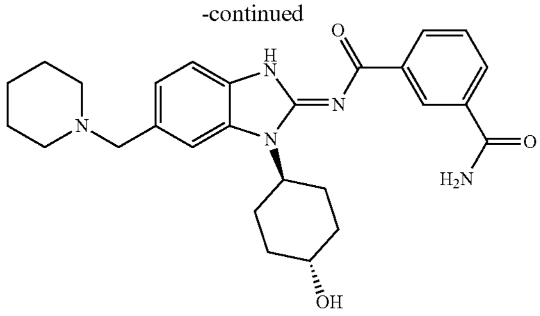

6

Compound 7 (35 mg, 86 μmol) was treated with water and DMF and concentrated to a dry powder to try to remove the methanol solvate. The residue was dissolved in DMF (1 mL). Solid Dess-Martin periodinane (44 mg, 94 μmol) was added slowly as a powder. After stirring for 30 minutes, TLC (19/1=$CH_2Cl_2$/MeOH) showed mostly a new product and little starting material and maybe some doubly oxidized material. The mixture was then treated with piperidine (40 μL) and sodium triacetoxyborohydride (72 mg, 343 μmol) and stirred overnight. The reaction mixture chromatographed (50 g isco C-18, 0 to 100% MeOH in 0.2% formic acid) to give, after concentration and trituration with ethyl acetate, compound 6 (29 mg, 75%) as a white powder. $^{1}$H-NMR (dmso-$d_6$) 12.79 (br s, 1H), 8.67 (s, 1H), 8.35 (d, J=8 Hz, 1H), 8.19 (s, 1H, formate), 8.10 (br s, 1H), 7.98 (d, J=8 Hz, 1H), 7.57 (s, 1H), 7.56 (t, J=8 Hz, 1H), 7.50 (d, J=8 Hz, 1H), 7.39 (br s, 1H), 7.17 (d, J=8 Hz, 1H), 4.77 (m, 1H), 3.71 (tt, J=4, 11 Hz, 1H), 2.54 (m, 2H), 2.42 (m, 4H), 2.03 (br d, J=12 Hz, 2H), 1.80 (br d, J=12 Hz, 2H), 1.53 (m, 4H), 1.47 (m, 2H), 1.41 (m, 2H).

Example 4

Synthesis of Compounds 8 and 9

8

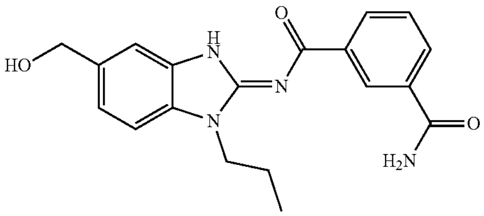

9

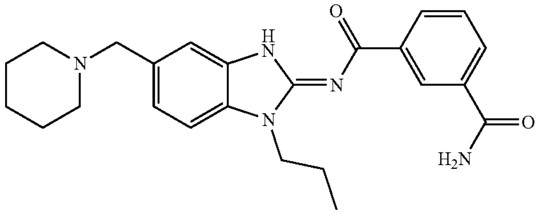

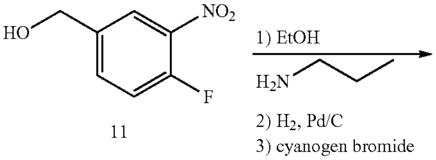

11

-continued

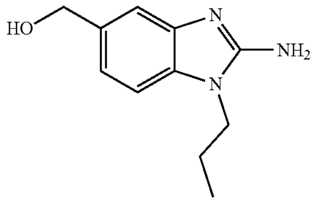

25

Benzyl alcohol 11 (1.26 g, 7.36 mmol) and n-propylamine (4.28 g, 5.9 mL, 72.7 mmol) were dissolved in ethanol (20 mL) and stirred at RT for a day. TLC showed complete reaction. The reaction mixture was concentrated to give the product, 25, as an oil. The oil was dissolved in ethanol (35 mL), treated with 10% Pd/C (160 mg) in an ethanol slurry and vacuum/purged with hydrogen gas 4 times and left to stir under hydrogen. When the color disappeared (after around 3 h), the mixture was filtered through Celite and treated with cyanogen bromide (1.8 g, 17 mmol) and left to stir for 3 days. The mixture was concentrated to an oil. The oil was dissolved in DMSO and water and chromatographed twice (120 g isco C-18, 0 to 100% MeOH in 0.2% formic acid) to give the product as a glass. The glass was treated with 1N HCl (10 mL) and concentrated from ethanol, then triturated with ethyl acetate to give the HCl salt of 25 (754 mg, 42%) as a crunchy white solid.

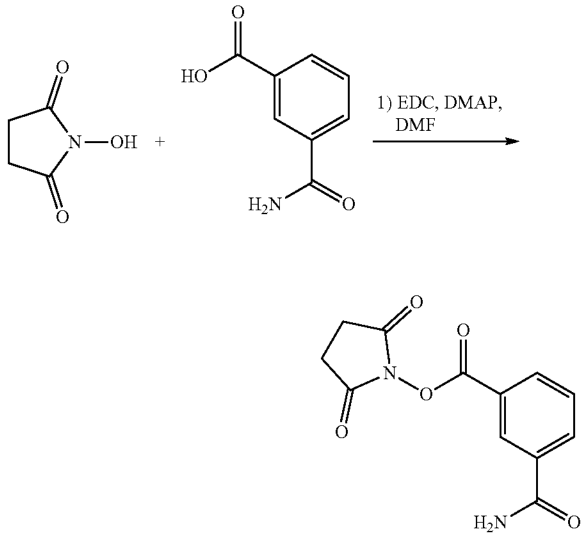

26

A mixture of 3-carbamoylbenzoic acid (2 g, 12.1 mmol), N-hydroxysuccinimide (1.39 g, 12.1 mmol), DMAP (14 mg, 121 μmol) and EDC (2.79 g, 14.5 mmol) were slurried in methylene chloride (20 mL). Hunig's base (3.1 g, 4.2 mL, 24 mmol) was added and the mixture stirred at RT overnight. The reaction mixture was concentrated and the residue was triturated and shaken with water, then filtered off, washed with water, and air-dried to give 26 (2.35 g, 74%) as a white powder. $^1$H-NMR (dmso-$d_6$) 8.57 (br s, 1H), 8.30 (d, J=8 Hz, 1H), 8.30 (br s, 1H), 7.76 (t, J=8 Hz, 1H), 7.63 (br s, 1H), 2.91 (s, 4H).

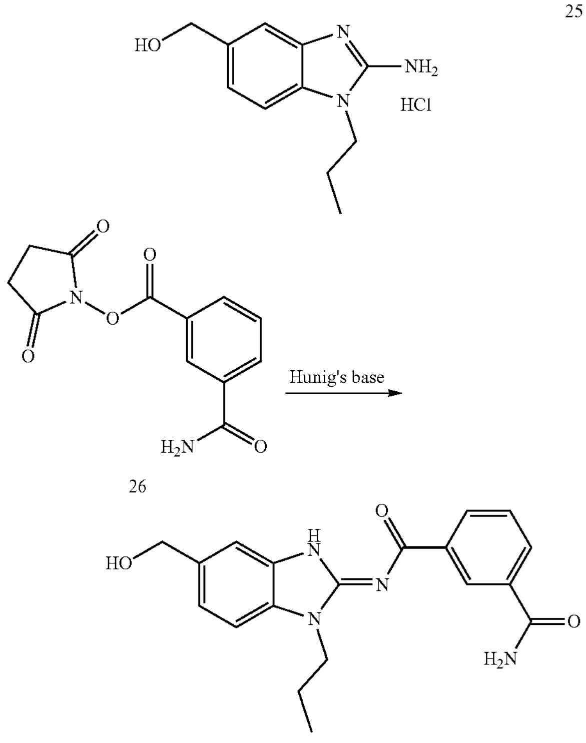

26

8

Amino benzimidazole 25 (400 mg, 1.65 mmol) and NHS ester 26 (434 mg, 1.65 mmol) were mixed in DMF (4 mL) and treated with Hunig's base (867 μL, 642 mg, 4.96 mmol) and stirred at RT for 1 d. The reaction mixture was loaded directly onto a column and chromatographed (120 g isco C-18, 0 to 100% MeOH in 0.2% formic acid) and concentrated to give compound 8 (192 mg, 32%) as a white powder. $^1$H-NMR (dmso-$d_6$) 12.73 (br s, 1H), 8.68 (s, 1H), 8.37 (d, J=8 Hz, 1H), 8.06 (br s, 1H), 7.98 (d, J=8 Hz, 1H), 7.54 (t, J=8 Hz, 1H), 7.53 (s, 1H), 7.47 (d, J=8 Hz, 1H), 7.40 (br s, 1H), 7.20 (d, J=8 Hz), 5.33 (t, J=5.7 Hz, 1H), 4.56 (d, J=5.7 Hz, 2H), 4.26 (t, J=7 Hz, 2H), 1.85 (hex, J=7 Hz, 2H), 0.92 (t, J=7 Hz, 3H).

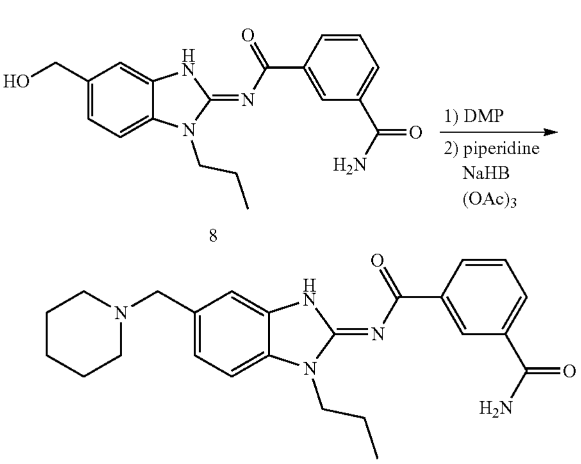

8

9

Compound 8 (160 mg, 454 μmol) was dissolved in DMF (2 mL). Dess-Martin periodinane (200 mg, 472 μmol) was quickly added as a powder. After 1 h, TLC showed no apparent starting material so the mixture was then treated with piperidine (77 mg, 89 μL, 908 μmol) followed by acetic acid (100 μL) and sodium triacetoxyborohydride (192 mg, 908 μmol) and stirred for 3 days. The reaction mixture was added to a column with some DMSO and chromatographed (120 g isco C-18, 0 to 100% MeOH in 0.2% formic acid) give, after concentration and trituration with ethyl acetate, the product compound 9 (136 mg, 64%) as an off-white powder. $^1$H-NMR (dmso-$d_6$) 12.69 (br s, 1H), 8.68 (s, 1H), 8.37 (d, J=8 Hz, 1H), 8.16 (s, 1H, formate), 8.09 (br s, 1H), 7.98 (d, J=8 Hz, 1H), 7.54 (t, J=8 Hz, 1H), 7.49 (s, 1H), 7.46 (d, J=8 Hz, 1H), 7.40 (br s, 1H), 7.18 (dm J=8 Hz, 1H), 4.25 (t, J=7 Hz, 2H) 3.51 (s, 2H), 2.36 (m, 4H), 1.84 (hex, J=7 Hz, 2H), 1.50 (m, 4H), 1.40 (m, 2H), 0.93 (t, J=7 Hz, 3H).

Example 5

General Experimental Procedures

Macrophage Differentiation

THP-1 cells were treated with 100 nM phorbol 12-myristate 13-acetate (PMA) for 72 hours in RPMI 1640X media. Cells were rested in PMA free media 24 hours prior to treatments. LPS (10 ng/mL) was used for pro-inflammatory stimulation.

Cytokine Profile

THP-1 cells were treated with 10 μM of designated drug or vehicle (DMSO) and 24 hours after treatment, supernatant was added to Human Cytokine XL proteome array (R&D Systems) in accordance with manufacturer protocol. Chemiluminescence was used to visualize protein quantities.

Animal Care

The DBA/1 CIA model was conducted in accordance with The Guide for the Care & Use of Laboratory Animals (8th Edition) and therefore in accordance with all Bolder BioPATH IACUC approved policies and procedures. The Bolder Biopath IACUC approved a “blanket” IACUC protocol for this specific working protocol (BBP-001). No acceptable alternative test systems were identified for the animals used in this study. Unless otherwise specified, studies were performed in male DBA/1 mice, and animals which failed to develop CIA arthritis by day 21 were excluded from analysis. Clinical evaluation was performed under experimenter blinded conditions. Pharmacokinetic studies were approved and carried out in accordance with the University of North Carolina-Chapel Hill, Institution Animal Care and Use Committee (IACUC) and conformed to the National Institutes of Health Guide for the Care and Use of Laboratory Animals. Mice were housed in a temperature and humidity-controlled facility under 12-hour light/dark cycle (lights on at 7 am) with access to food and water ad libitum.

Collagen Type II Induced Arthritis (CIA) Induction

Collagen was prepared as a 4 mg/ml solution in 0.01M acetic acid. Equal volumes of 4 mg/ml collagen and 5 mg/ml Freund’s complete adjuvant were emulsified by hand mixing with syringes for approximately 5 min, at which point a bead of this material holds its form when placed in water. On study days 0 & 21, animals were anesthetized with Isoflurane and given intradermal injections of a total of 400 μg of Type II collagen in Freund’s complete adjuvant at the base of the tail.

CIA Experimental Design

On study day 0 and again on day 21, the mice were anaesthetized with Isoflurane (VetOne, catalogue No. 502017), shaved at the base of the tail, and injected intradermally with 100 μL of Freund’s complete adjuvant (Sigma Aldrich, catalogue No. R134067) with supplemental *Mycobacterium tuberculosis* (H37 Ra: BD, catalogue No. 231141) (2.5 mg/mL final concentration) containing bovine type II collagen (BBP Batch No. 10, lot No. 111813) (2 mg/mL final concentration). On study day 21, the animals were randomized into the study based on body weight. Animal body weights were measured and animals enrolled in respective treatment groups. Unless otherwise specified, clinical scores were given for each of the paws (right front, left front, right rear, left rear) on study days 21 through 36. The mice were euthanized for necropsy on study day 36 (approximately 3 hours after the final dose), and samples were collected.

Immunohistological Staining

After 1-2 days in fixative and 4-5 days in 5% formic acid for decalcification, tissues were trimmed, and processed for paraffin embedding. Paws were embedded in paraffin in the frontal plane and the knees were embedded with the patella facing down. Ankles, if left attached to the hind paw, were also embedded in the frontal plane but may be detached and sectioned in the sagittal plane for special purposes. Left/right pairs were typically embedded in the same block. Sections were cut and stained with toluidine blue.

Scores for Synovitis, Pannus Formation, Degradation of Cartilage, and Bone

A. Paw Score Criteria

0=Normal. 0.5=Very minimal, affects only 1 joint or minimal multifocal periarticular infiltration of inflammatory cells. 1=Minimal infiltration of inflammatory cells in synovium and periarticular tissue of affected joints. 2=Mild infiltration of inflammatory cells. When referring to paws, generally restricted to affected joints (1-3 affected). 3=Moderate infiltration with moderate edema. When referring to paws, restricted to affected joints, generally 3-4 joints and the wrist or ankle. 4=Marked infiltration affecting most areas with marked edema, 1 or 2 unaffected joints may be present. 5=Severe diffuse infiltration with severe edema affecting all joints (to some extent) and periarticular tissues.

B. Knee Score Criteria

0=Normal. 0.5=Very minimal, affects only one area of the synovium or minimal multifocal periarticular infiltration of inflammatory cells. 1=Minimal infiltration of inflammatory cells in synovium and periarticular tissue of affected synovial areas. 2=Mild diffuse infiltration of inflammatory cells. 3=Moderate diffuse infiltration of inflammatory cells. 4=Marked diffuse infiltration of inflammatory cells. 5=Severe diffuse infiltration of inflammatory cells.

C. Cartilage Damage Score Criteria

0=Normal. 0.5=Very minimal=Affects marginal zones only of one to several areas (knees) or joints (paws). 1=Minimal=Generally minimal to mild loss of toluidine blue staining (proteoglycan) with no obvious chondrocyte loss or collagen disruption in affected joints/areas. 2=Mild=Generally mild loss of toluidine blue staining (proteoglycan) with focal areas of chondrocyte loss and/or collagen disruption in some affected joints/areas. Paws may have one or two digit joints with near total to total loss of cartilage. 3=Moderate=Generally moderate loss of toluidine blue staining (proteoglycan) with multifocal chondrocyte loss and/or collagen disruption in affected joints/areas. Paws may have three or four joints with near total or total loss. In the knee, some matrix remains on any affected surface with areas of severe matrix loss. 4=Marked=Marked loss of toluidine blue staining (proteoglycan) with multifocal marked (depth to deep zone or tidemark) chondrocyte loss and/or collagen disruption in most joints with a few unaffected or mildly affected. In the knee, one surface with total to near total cartilage loss. 5=Severe=Severe diffuse loss of toluidine blue staining (proteoglycan) with severe (depth to tide mark) chondrocyte loss and/or collagen disruption in most or all joints.

Pharmacokinetics

All serum/drug samples were frozen and stored at −80° C., unless otherwise specified. Before quantification in serum, a standard curve was made using compound 3, a structural analog of compound 5 that serves as an internal standard. This internal standard solution was used for tissue homogenization. LC-MS analysis was performed at the Duke Proteomics and Metabolomics Core Facility. The final concentration of compound 5 in the plasma was calculated per ml of plasma.

Statistical Analysis

GraphPad Prism 8 was used for statistical analysis. For each analysis, total n and SEM are presented in the figure legend. An alpha of 0.05 was used for all statistical analysis.

Example 6

Development and Evaluation of Selective and Orally Bioavailable TAK1 Inhibitors

This example describes the development and initial evaluation of TAK1 inhibitors of the present disclosure that exhibit high TAK1 kinase selectivity while being water soluble and orally bioavailable, thereby addressing the long felt need for orally administrable and selective TAK1 inhibitors.

Rational Selective TAK1 Inhibitor Design

Figure 8A:
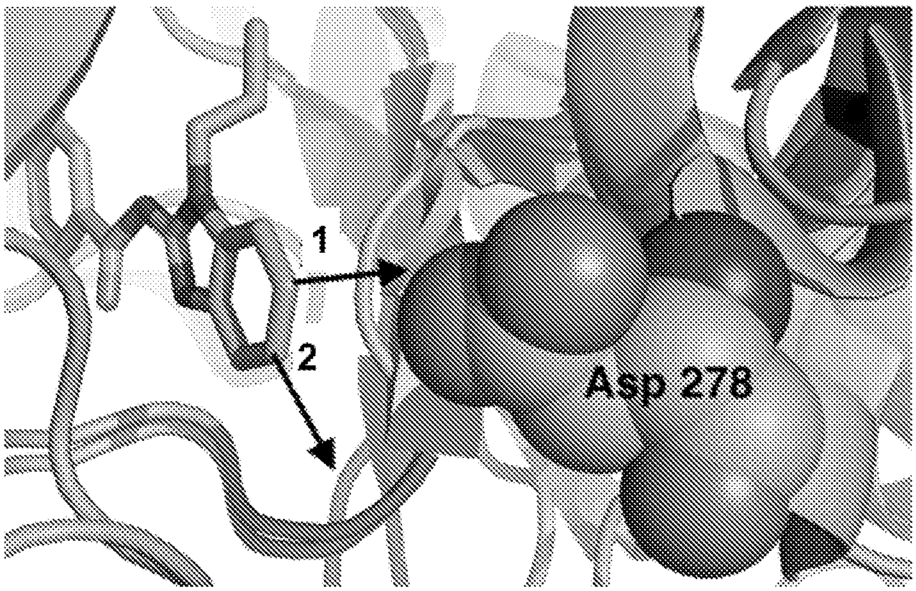
FIG. 8A shows an overlay of TAK1 (5V5N, blue) and IRAK4 (4RMZ, green) crystal structures with a benzimidazole-derived compound, in this case, compound 1.
Figure 8B:
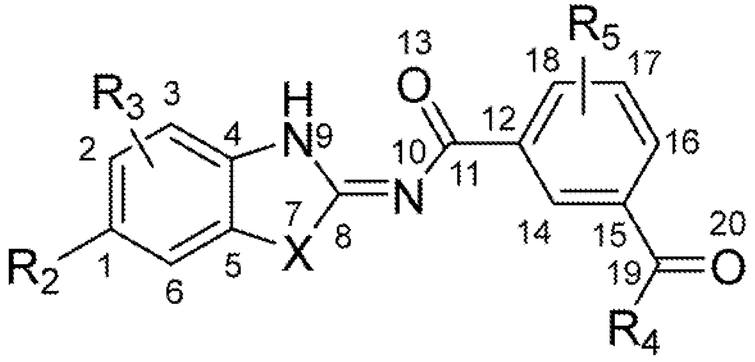
FIG. 8B shows the structure of Formula (I) with atom positions.

Starting from the scaffold of compound 1 (also referred to herein as takinib), which showed low bioavailability and exhibited some affinity for IRAK4, albeit ~12 fold less than TAK1, a structure-activity relationship (SAR) study was performed based on the co-crystal structure of compound 1 and TAK1 (FIG. 8A). The analysis revealed that the isophthalamide ring (FIG. 8C, pos. 12, 14-18) was snugly bound to parts of the binding pocket within TAK1, and that the benzimidazole (FIG. 8C, pos. 1, 2, N-7) was more solvent exposed. Affinity resins derived from acrylates at positions 1 and 2 were therefore prepared and, surprisingly, the resin from position 2 captured both TAK1 and IRAK4, whereas, the resin from position 1 only captured TAK1 (data not shown). This surprising finding provided supporting evidence suggesting that derivatives at position 1 may be selective for TAK1 over IRAK4. Furthermore, overlap of the takinib-TAK1 crystal structure with an IRAK4 structure containing a similar ligand confirmed accommodation of substitutions in the 2 position for TAK1 but not IRAK4, and revealed parts of the molecular structure which were solvent exposed (FIG. 8C, pos. 1, 2 and N-7), suggesting regions that can be modified to improve physicochemical parameters such as solubility without loss of specificity or potency for TAK1.

Based on these results, compounds 2-10 were prepared as described in EXAMPLES 1-4. The synthesized compounds as well as their $IC_{50}$ values for TAK1 and IRAK4 are shown below in TABLE 1.

TABLE 1

Examples of TAK1 inhibitors and Pharmacodynamic Properties

| Compound | *$R_1$ | *$R_2$ | *$R_3$ | $IC_{50}$ (TAK1) [nM] | $IC_{50}$ (IRAK4) [nM] | Ratio $IC_{50}$ (IRAK4)/ $IC_{50}$ (TAK1) |
|---|---|---|---|---|---|---|
| 1 | Propyl | H | H | 9 | 120 | 13 |
| 2 | 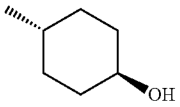 | H | 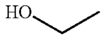 | nt | nt | n/a |
| 3 | 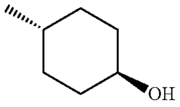 | H | 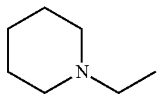 | 2.8 | 8.5 | 3 |
| 4 | Propyl | 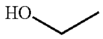 | H | 2.6 | 48 | 18 |
| 5 | Propyl | 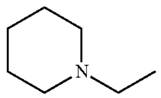 | H | 2.5 | 2,500 | 1000 |
| 6 | 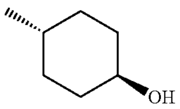 | 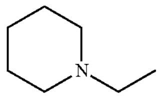 | H | 2.4 | 402 | 168 |
| 7 | 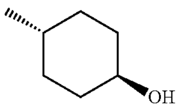 | 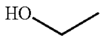 | H | 1.6 | 8.2 | 5 |
| 8 | Propyl | H | 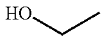 | 3.1 | 29 | 9 |

TABLE 1-continued

| Examples of TAK1 inhibitors and Pharmacodynamic Properties | | | | | | |
|---|---|---|---|---|---|---|
| Compound | $^*R_1$ | $^*R_2$ | $^*R_3$ | $IC_{50}$ (TAK1) [nM] | $IC_{50}$ (IRAK4) [nM] | Ratio $IC_{50}$ (IRAK4)/ $IC_{50}$ (TAK1) |
| 9 | Propyl | H | 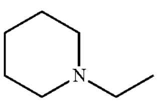 | 1.7 | 4.2 | 2 |
| 10 | Propyl | 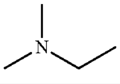 | H | 32 | 1,120 | 35 |

Figure 8C:
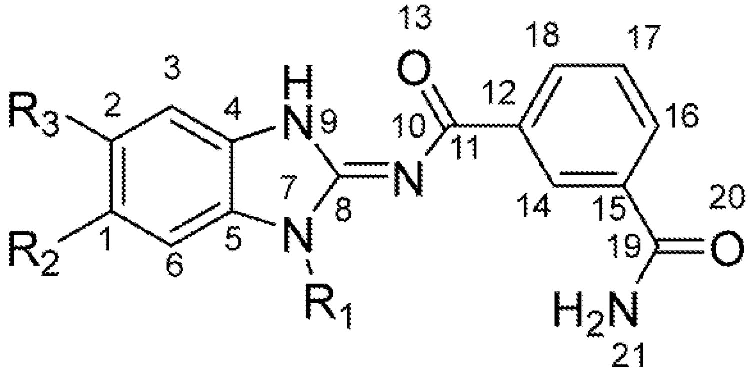
FIG. 8C shows the structure of Formula (II) with atom positions.

$^*R_1$, $R_2$, and $R_3$ of compounds 1-10 correspond to FIG. 8C (Formula (II)). Binding experiments to determine TAK1/RAK4-kinase selectivity were conducted as described in EXAMPLE 5.

The data showed that the hydroxylmethyl at $R_2$ seemed to be tolerated by IRAK4, suggesting that a larger substitution at position 1 ($R_2$) may drive selectivity toward TAK1. The inhibition data collected for compounds 5 and 6 with the piperidinomethyl substitution at position 1 ($R_2$) confirmed that hypothesis, showing selectivities for TAK1 over IRAK4 of 1000 and 168, respectively. Without being bound to any theory, it was assumed that the observed difference in TAK1 selectivity of compounds 5 and 6 may be due to a larger substituent at position 1 ($R_2$), which may have opened the binding pocket in a way that reduced the interaction of $R_2$ substituents with Asp 278 of TAK1 (see, e.g., FIG. 8A). Moreover, compounds 2-10 showed good water solubility as formate salts (>50 mg/mL).

Broader Kinome Selective Evaluation

Kinome selectivity of compound 5 was further screened using a kinase panel of 146 human kinases representing all gene family members within the human kinome. At 10 μM, compound 5 showed significant inhibition (<15% enzymatic activity) of TAK1, NUAK1, IRAK1, MAP4K5, CK1γ2, and ULK2.

Figure 1B:
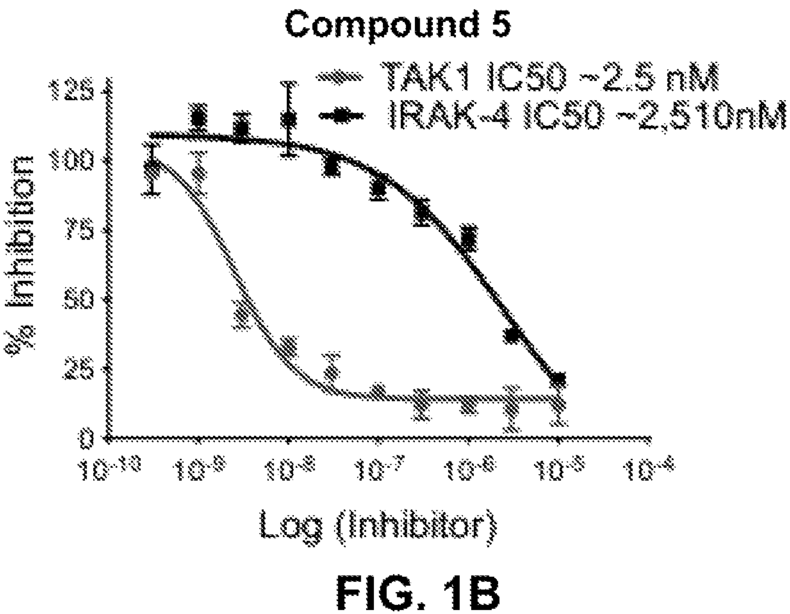
FIG. 1B shows percent inhibition of the kinases TAK1 and IRAK4 by compound 5 in a selectivity screening demonstrating minimal IRAK4 inhibition ($IC_{50}$=2,510 nM) while showing potent TAK1 inhibition ($IC_{50}$=2.5 nM).

Next, dose-response experiments of the top 10 kinases inhibited by compound 5 in the initial kinome screen were conducted as described in EXAMPLE 5. FIG. 1A shows percent inhibition of the top 10 kinases by compound 5 in a dose-response experiment. The top 10 kinases were selected in an initial kinome screen. FIG. 1A shows that TAK1 was most potently inhibited by compound 5 with a half maximal inhibitory concentration ($IC_{50}$) value of 8 nM, 3.6-fold more potent that the next kinase CLK2 (29 nM), and 4.1-fold GCK (33 nM). Half maximal inhibitory concentrations of other kinases such as ULK2 (63 nM), MAP4K5 (124 nM), IRAK1 (264 nM), NUAK (270 nM), CSNK1G2 (809 nM), CAMKKβ-1 (1,280 nM) and MLK1 (5,585 nM) are also shown. FIG. 1B shows percent inhibition of the kinases TAK1 and IRAK4 by compound 5 in a selectively screening demonstrating minimal IRAK4 inhibition ($IC_{50}$=2,510 nM) while showing potent TAK1 inhibition ($IC_{50}$=2.5 nM).

Example 7

In Vitro Cytokine Inhibition Profiles of Selective TAK1 Inhibitors

This example describes the results of in vitro cytokine inhibition experiments for compounds 3, 5, and 6 to determine the anti-inflammatory effects of these compounds since TAK1 inhibition can lead to significant reduction of TNF expression in pro-inflammatory stimulated immune cells.

Figure 1C:
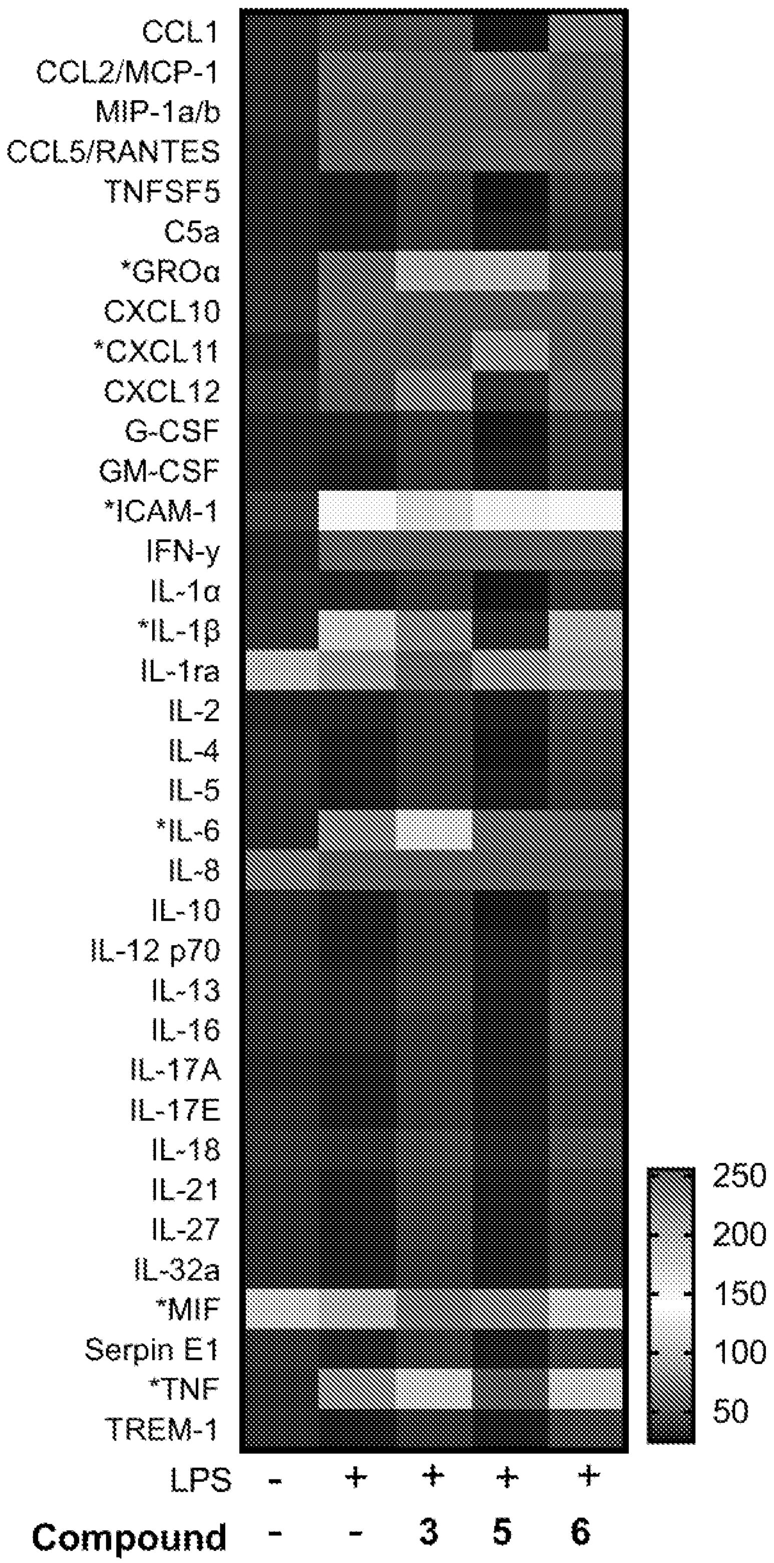
FIG. 1C shows results of a comparison experiment of various TAK1 inhibitors (compounds 3, 5, and 6) and their cytokine expression profiles in the THP-1 LPS induced inflammatory model.

To evaluate the anti-inflammatory effects of compounds 3, 5, and 6, THP-1 human macrophages were stimulated with LPS and IFNγ in the presence of TAK1 inhibitor (10 μM) or vehicle. The results, shown in FIG. 1C, demonstrate that compound 5 significantly attenuated TNF expression 11-fold, compared to 2.5-fold reduction with compound 3 and 1.2-fold by compound 6. Moreover, it was also observed that treatment with compound 5 led to significant reductions in CCL1 ($p<0.04$), GROa ($p<0.001$), CXCL11 ($p<0.0002$), ICAM-1 ($p<0.04$), IL-1B ($p<0.0001$), IL-6 ($p<0.0001$), and MIF ($p<0.0017$) expression compared to vehicle treated cells.

Figure 1D:
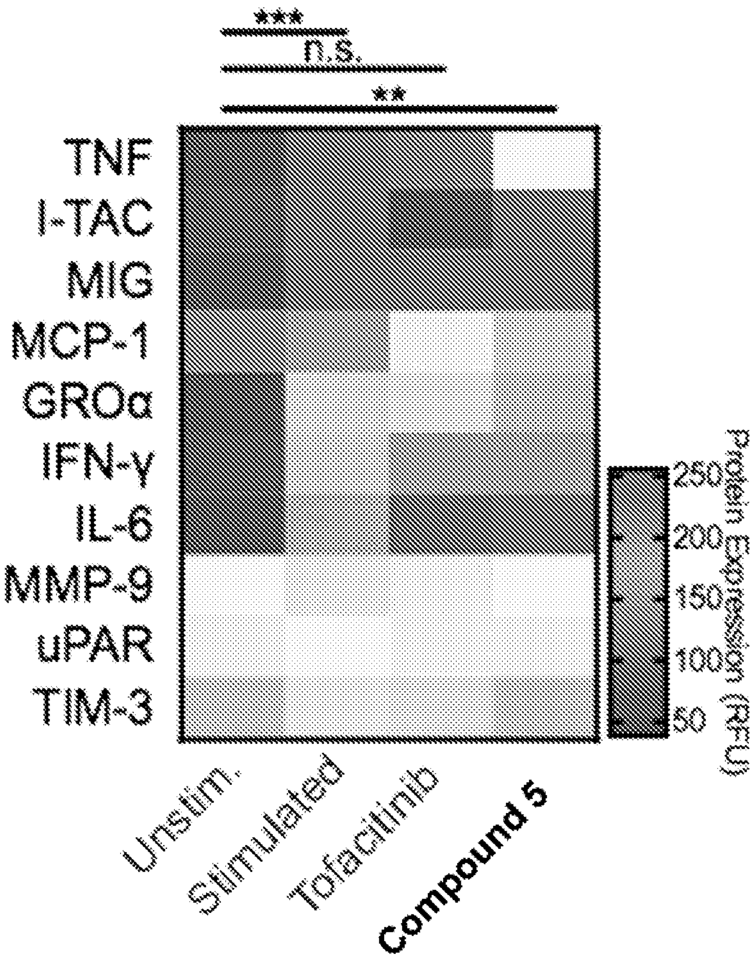
FIG. 1D shows TAK1-specific cytokine inhibition by compound 5 compared to the JAK inhibitor tofacitinib that is currently approved for the treatment of rheumatoid arthritis, psoriatic arthritis, and ulcerative colitis.

Next, the anti-inflammatory effects of compound 5 were compared in another in vitro cytokine inhibition experiment to the JAK inhibitor tofacitinib, a frontline therapeutic for rheumatoid arthritis, psoriatic arthritis, and ulcerative colitis. The resulting data, shown in FIG. 1D, demonstrate that acute inhibition of TAK1 in THP-1 human macrophages following LPS and IFNγ challenge using compound 5 significantly and selectively reduced TNF secretion with minimal to no TNF reduction seen in tofacitinib-treated cells.

Together, these results demonstrate the anti-inflammatory effects and potent TNF inhibition achieved by acute and selective TAK1 inhibitions using the compounds of the present disclosure, e.g., compound 5.

Example 8

Pharmacokinetic Profiles of Orally Administered, Selective TAK1 Inhibitors

This example describes the results of pharmacokinetic (PK) in vivo studies, demonstrating oral bioavailability of the selective TAK1 inhibitors of the present disclosure.

To that end, healthy adult Sprague Dawley rats (male, n=3) were administered compounds 3, 5, and 6 at 50 mg/kg via oral gavage. Sequential blood draws at 1, 2, 4, 8, 12 and 24 hours post-administration, as well as urine collection at 4, 12 and 24 hours post-administration were conducted, and drug concentration in the obtained samples was determined by LC-MS as described in EXAMPLE 5.

Figure 2A:
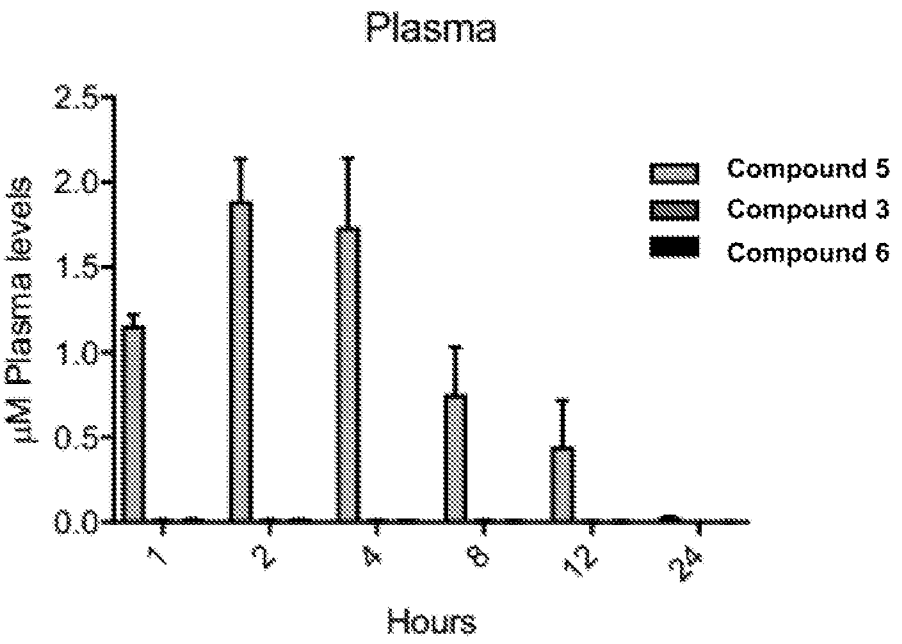
FIG. 2A shows the plasma concentration (in μM) of compounds 3, 5, and 6 as a function of time (measured at 1, 2, 4, 8, 12, and 24 hours post-administration) in adult Sprague Dawley rats (male) following the administration of 50 mg/kg compound via oral gavage. Experiments were performed in triplicates.
Figure 2B:
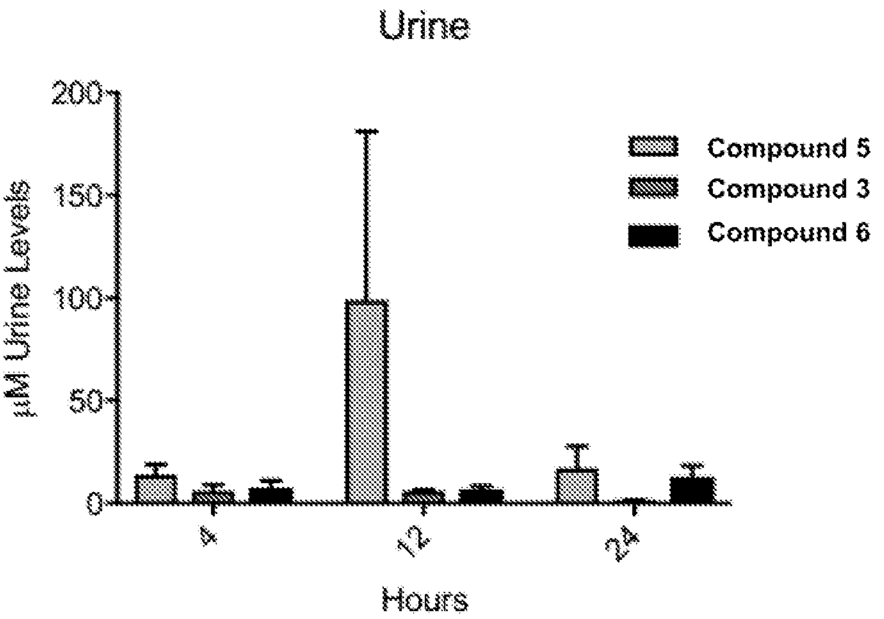
FIG. 2B shows the concentration (in μM) of compounds 3, 5, and 6 in collected urine samples as a function of time (measured at 4, 12, and 24 hours post-administration) of adult Sprague Dawley rats (male) following the administration of 50 mg/kg compound via oral gavage. Experiments were performed in triplicates.

FIGS. 2A-2B show that compounds 3 and 6 showed low nM plasma levels across all timepoints. Despite low plasma surveillance, both compounds 3 and 6 showed M urine levels up to 24 hours post gavage. Since both compounds 3 and 6 have the addition of the cyclohexanol to the 1st nitrogen of the benzimidazole, it was hypothesized whether the cyclohexanol moiety may contribute to the reduced bioavailability or metabolism of both compounds. FIGS. 2A-2B also show that compound 5, which lacks the cyclohexanol on the 1st nitrogen of the benzimidazole in favor of an n-propyl group, exhibited a $C_{max}$ of 1.89 μM in plasma 2 hours post gavage. Compound 5 also showed M plasma concentration up to 8-12 hours post gavage, and urine analysis of compound 5 showed a peak in urine concentration at 12 hours of 100 μM.

These results demonstrate that selective TAK1 inhibitors of the present disclosure, e.g., compound 5, provide, in addition to their kinase selectivity, good water solubility and high oral bioavailability, features of kinase inhibitors long sought after.

Example 9

Initial Toxicity Testing of TAK1 Inhibitors and their Evaluation in a CIA Model

This example describes initial toxicity screens of TAK1 inhibitors of the present disclosure as well as their evaluation in a CIA mouse model of inflammatory arthritis.

Initial Toxicity Screen

Figure 6A:
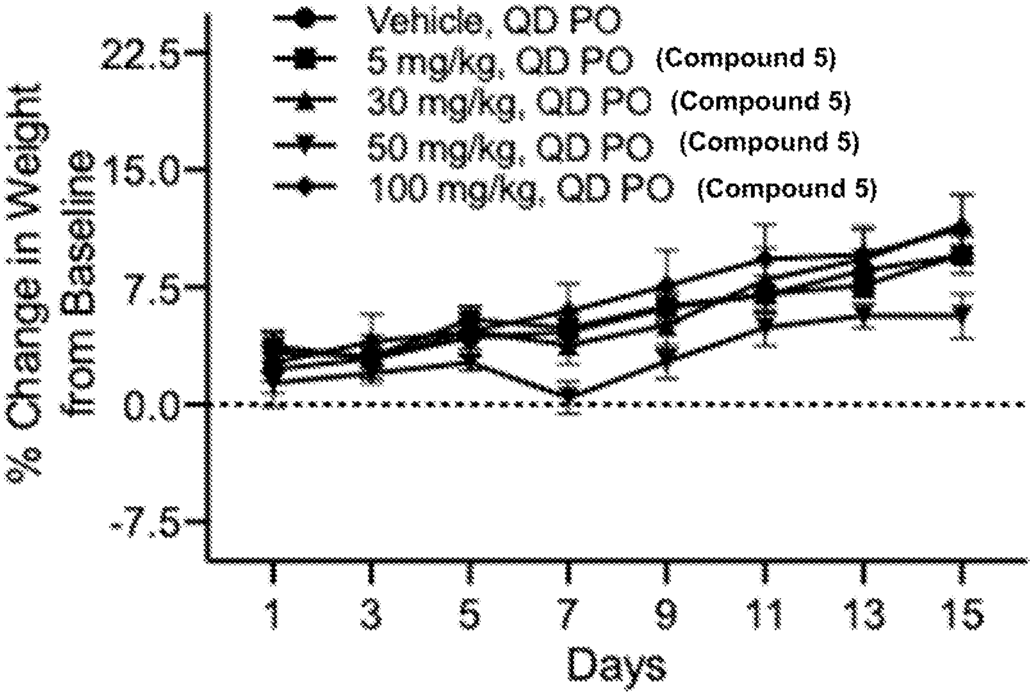
FIG. 6A shows the change in body weight relative to baseline over a period of 14 days in male CD-1 mice (n=4) treated orally and once daily with (i) vehicle (DMSO), (ii) compound 5 (5 mg/kg), (iii) compound 5 (30 mg/kg), (iv) compound 5 (50 mg/kg), or (v) compound 5 (100 mg/kg). The data showed no signs of morbidity throughout the study.

Maximum tolerated dose studies and toxicology of compound 5 further established the safety and tolerance of this compound. Here, mice were treated daily with compound 5 (PO) at 5, 30, 50 and 100 mg/kg dosing for 15 consecutive days. Daily body weights were taken as well as clinical observations. FIG. 6A shows that no significant weight loss was observed between any of the treatment groups. Following termination of the study, relative liver, spleen, kidney, brain, thymus, adrenals, heart, and testes weights were measured, and no significant weight loss was observed between any of the treatment groups in any of the tissues collected (see, FIGS. 6B-6G, respectively).

Compound Evaluation in a CIA Mouse Model of Inflammatory Arthritis

Figure 3A:
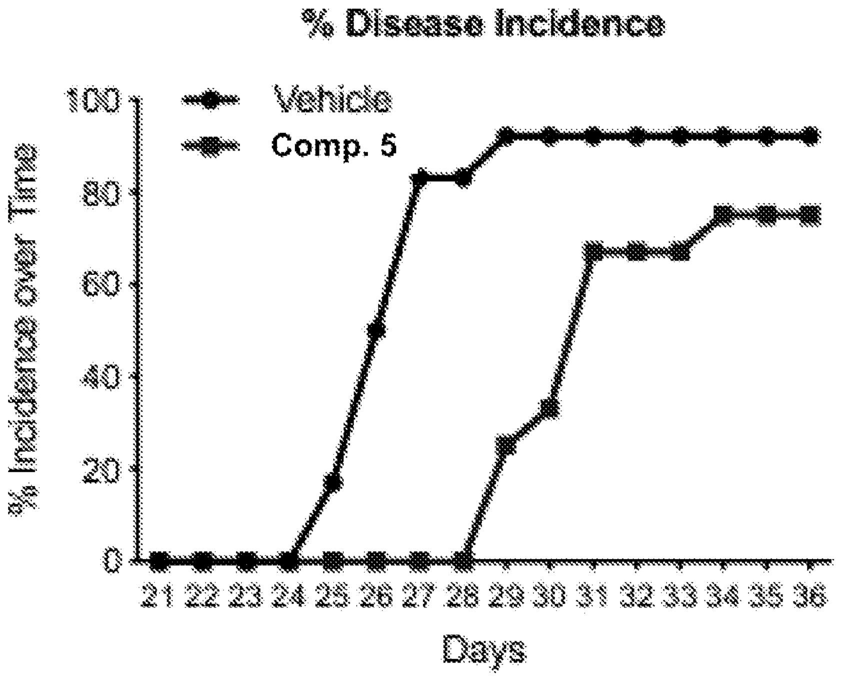
FIG. 3A shows the percent incidence of arthritis over time in a CIA mouse model of inflammatory arthritis. The data show that treatment with compound 5 (Comp. 5, 50 mg/kg, intraperitoneal (IP), once daily (QD) on days 21-26, and once every other day (Q2D) on days 27-36) significantly delayed disease onset and decreased disease incidence; e.g., 92% disease incidence on day 36 in vehicle (DMSO) treated animals (n=12) compared to 75% disease incidence on day 36 in animals (n=12) treated with compound 5.
Figure 3B:
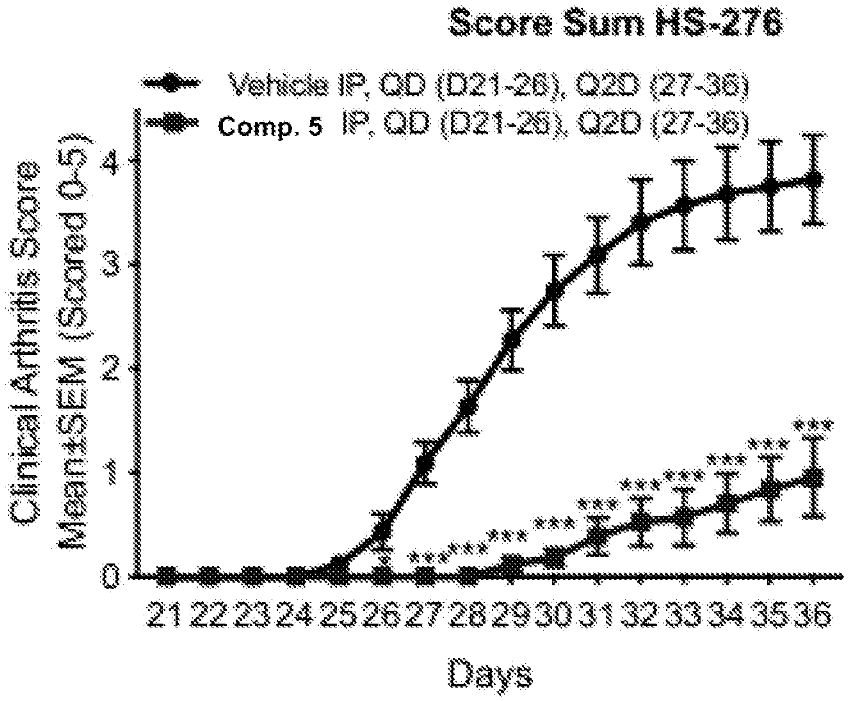
FIG. 3B shows the clinical arthritis score over time in the CIA mouse model of inflammatory arthritis. The data show that clinical arthritis scores for mice (n=12) treated with compound 5 (Comp. 5, 50 mg/kg, IP, once daily (QD) on days 21-26, and once every other day (Q2D) on days 27-36) were significantly reduced on days 26 through 36 as compared to the disease control (vehicle (DMSO)-treated) group.
Figure 3C:
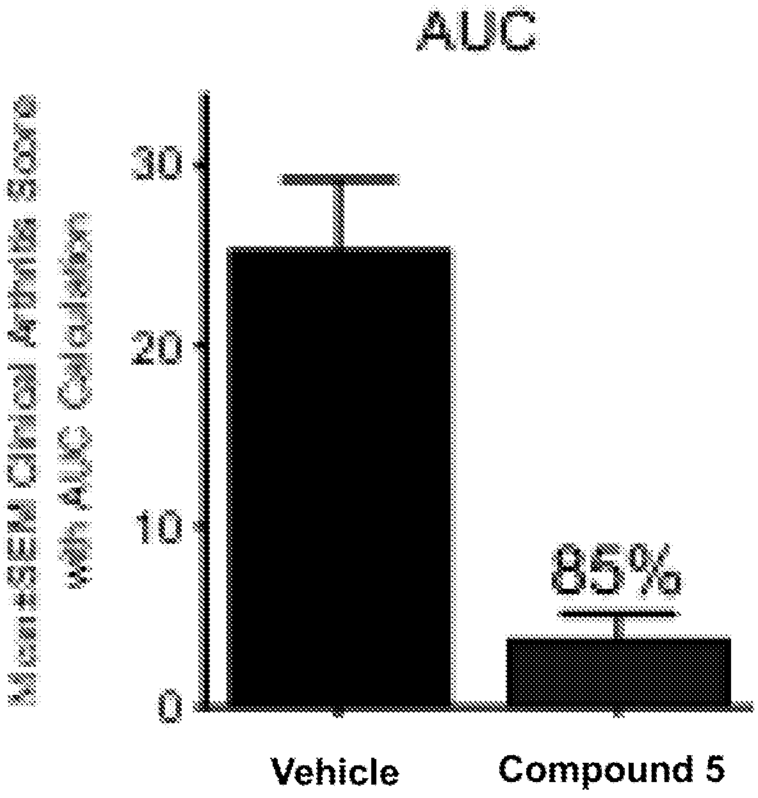
FIG. 3C shows a bar graph illustrating the results of area under the curve (AUC) calculations for the clinical arthritis scores shown in FIG. 3B. The data demonstrate that clinical arthritis scores were statistically (85%) reduced in mice (n=12) treated with compound 5 (Comp. 5, 50 mg/kg, IP, once daily (QD) on days 21-26, and once every other day (Q2D) on days 27-36) as compared to disease control (vehicle (DMSO)-treated) mice.

The CIA mouse model of inflammatory arthritis was established as described in EXAMPLE 5. FIG. 3A shows that treatment with compound 5 (50 mg/kg, intraperitoneal (IP), once daily (QD) on days 21-26, once every other day (Q2D) on days 27-36) significantly delayed disease onset and decreased disease incidence, e.g., 92% on day 36 in vehicle (DMSO) treated animals (n=12) compared to 75% disease incidence on day 36 in animals (n=12) treated with compound 5. Daily paw scores for disease control mice increased over the course of the study, peaking at termination (mean score of 3.50), and were statistically increased as compared to naïve mice (which had no clinical signs of arthritis) on days 27 through 36. FIG. 3B shows that clinical arthritis scores for mice treated with compound 5 (50 mg/kg) were significantly reduced on days 26 through 36 as compared to the disease control group. Area under the curve (AUC) calculations for clinical arthritis scores were statistically (85%) reduced in mice treated with compound 5 (50 mg/kg) as compared to disease control mice (FIG. 3C).

Figure 3D:
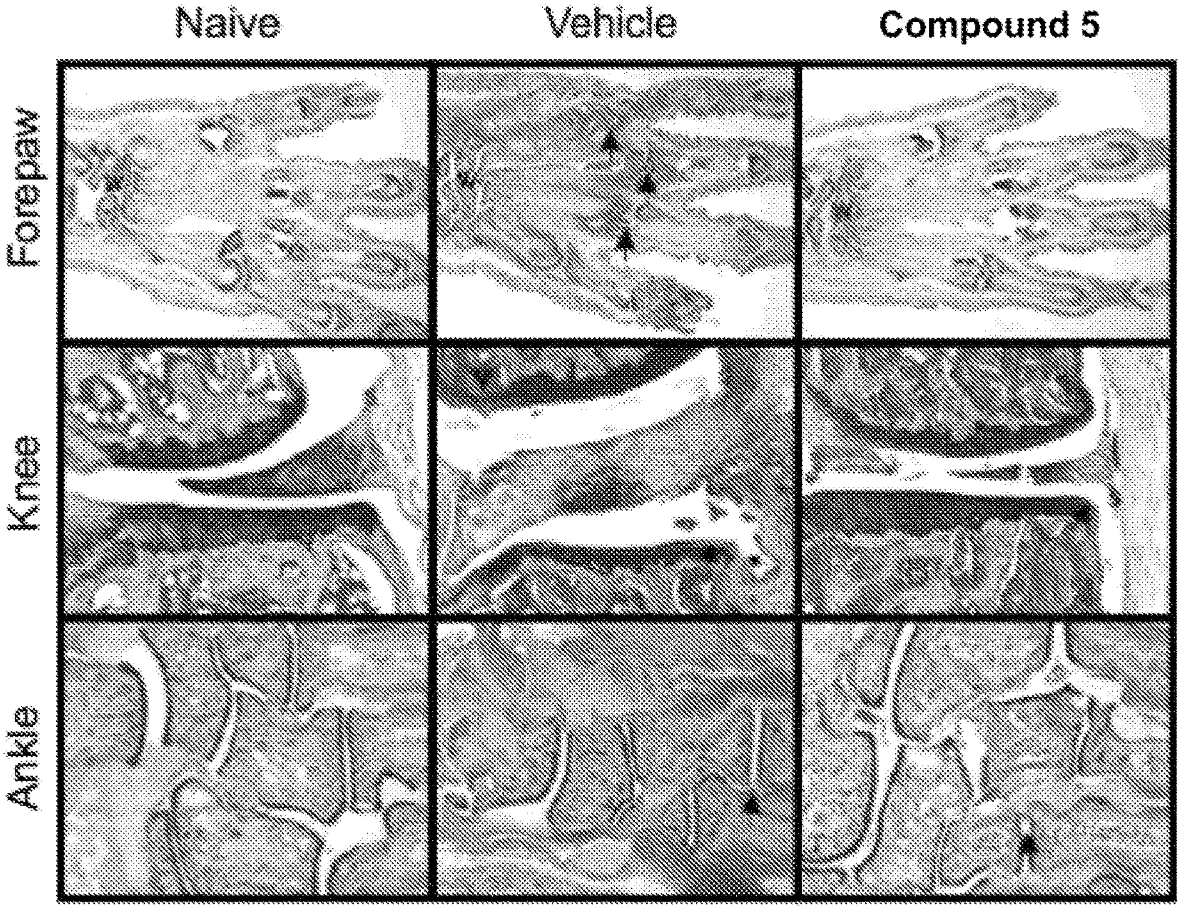
FIG. 3D shows histological evaluations of forepaw, knee, and angle joint tissues in animals (n=12) treated with compound 5 (Comp. 5, 50 mg/kg, IP, once daily (QD) on days 21-26, and once every other day (Q2D) on days 27-36) as compared to disease control (naïve, and vehicle (DMSO)-treated) mice. The data demonstrate that vehicle treated mice showed histopathologic changes consistent with those seen in animals having type II collagen induced arthritis including microscopic alteration and infiltration of synovium and periarticular tissue with neutrophils and mononuclear inflammatory cells, marginal zone pannus and bone resorption, and cartilage damage, whereas mice treated with compound 5 showed significantly fewer pathological changes and their histology results appeared comparable to those shown for naïve mice.
Figure 3E:
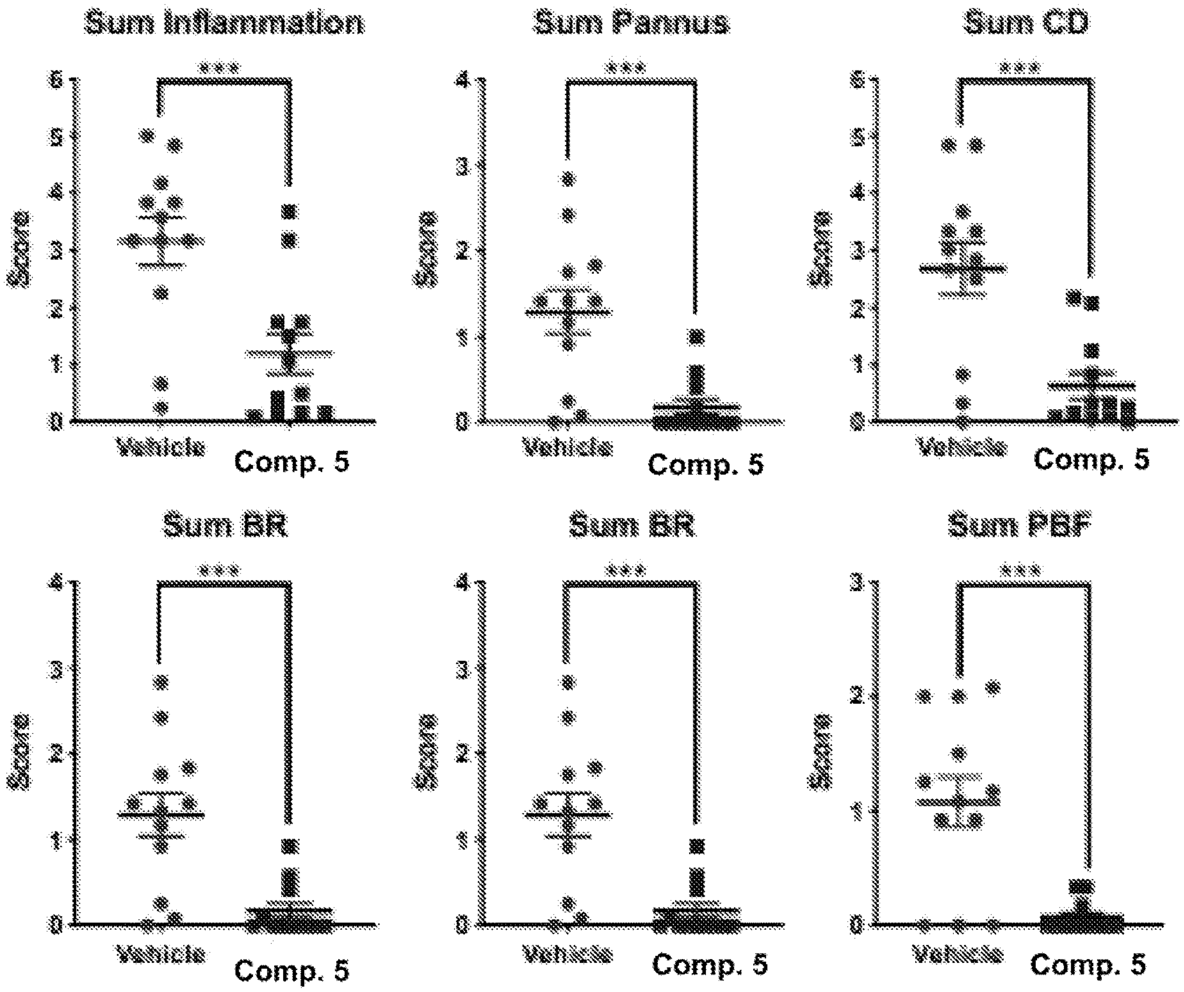
FIG. 3E shows a quantification of the histology results shown in FIG. 3D. The data show that mice (n=12) treated with compound 5 (Comp. 5, 50 mg/kg, IP, once daily (QD) on days 21-26, and once every other day (Q2D) on days 27-36) showed significantly reduced arthritis scores: 62% inflammation, 86% pannus, 76% cartilage damage, 87% bone resorption and 93% periosteal bone formation as compared to the vehicle treated control group.

FIG. 3D shows results of the evaluation of histological changes in vehicle versus treated mice that demonstrated that vehicle treated (but not compound 5 treated) mice had histopathologic changes consistent with those seen in type II collagen induced arthritis including microscopic alteration and infiltration of synovium and periarticular tissue with neutrophils and mononuclear inflammatory cells, marginal zone pannus and bone resorption, and cartilage damage. When considering all joints (paws and knees), mice treated with compound 5 (50 mg/kg) had significant reductions scores 62% inflammation, 86% pannus, 76% cartilage damage, 87% bone resorption and 93% periosteal bone formation as compared to the vehicle treated control group (FIG. 3E).

Taken together, these results demonstrate that the selective TAK1 inhibitors of the present disclosure, e.g., compound 5, can significantly delay disease onset and decrease disease incidence in vivo.

Example 10

Comparison of Selective TAK1 Inhibitors with Frontline RA Treatments in Treatment Refractory Settings Parental Administration This example describes the comparison of TAK1 inhibitors of the present disclosure with currently used frontline anti-inflammatory therapeutics in a CIA mouse model of human rheumatoid arthritis (RA). The data of this comparative study are shown in FIGS. 4A-4D.

To that end, compound 5 was first compared to vehicle, then to etanercept, methotrexate, and tofacitinib. The obtained data are shown in FIGS. 4A-4D.

Figure 4A:
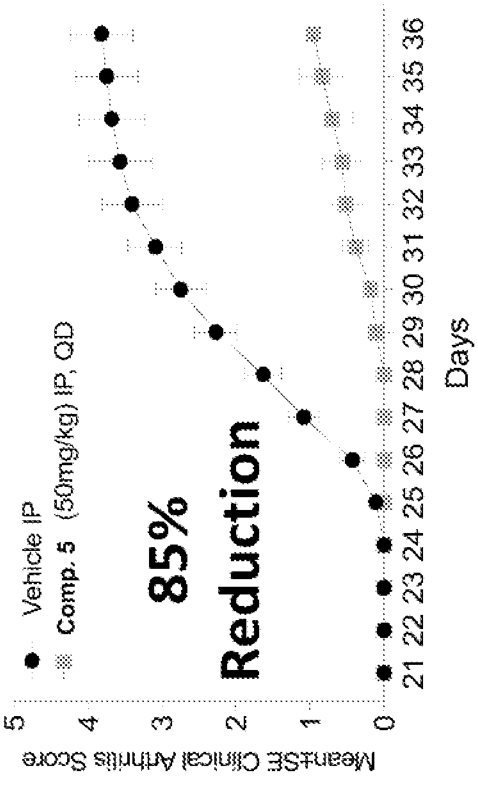
FIG. 4A shows the mean clinical arthritis score measured over time in a CIA mouse model of human rheumatoid arthritis for mice (n=12) treated either with vehicle (DMSO, IP, once daily) or compound 5 (Comp. 5, 50 mg/kg, IP, once daily). The data show an 85% reduction in clinical arthritis scores for mice treated with compound 5 compared to vehicle treated animals.

FIG. 4A shows the mean clinical arthritis score measured over time in a CIA mouse model of human RA for mice (n=12) treated either with vehicle (DMSO, IP, once daily) or compound 5 (50 mg/kg, IP, once daily). The data show an 85% reduction in clinical arthritis scores for mice treated with compound 5 compared to vehicle treated animals.

Figure 4B:
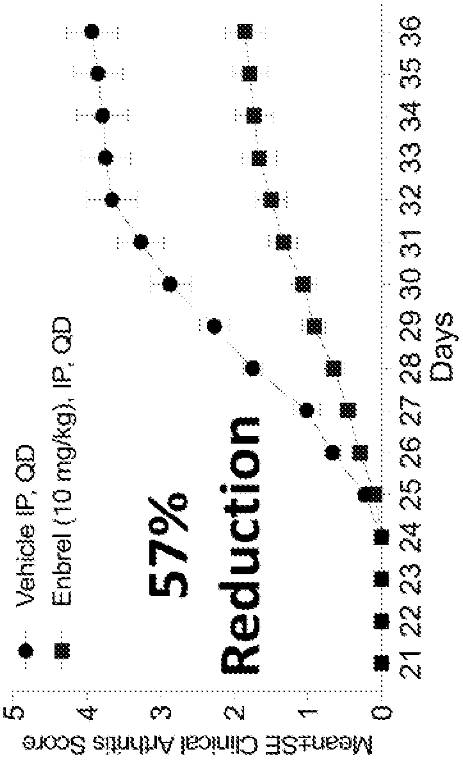
FIG. 4B shows the mean clinical arthritis score over time in the CIA mouse model of inflammatory arthritis for mice (n=12) treated either with vehicle (DMSO, IP, once daily) or the fusion protein etanercept (Enbrel®, 10 mg/kg, IP, once daily). The data show a reduction of only 57% (compared to 85% with compound 5) in clinical arthritis scores for mice treated with etanercept compared to vehicle treated animals.

FIG. 4B shows the mean clinical arthritis score measured over time in a CIA mouse model of human RA for mice (n=12) treated either with vehicle (DMSO, IP, once daily) or the fusion protein etanercept (Enbrel®, 10 mg/kg, IP, once daily). The data show a reduction of only 57% (compared to 85% with compound 5) in clinical arthritis scores for mice treated with etanercept compared to vehicle treated animals.

Figure 4C:
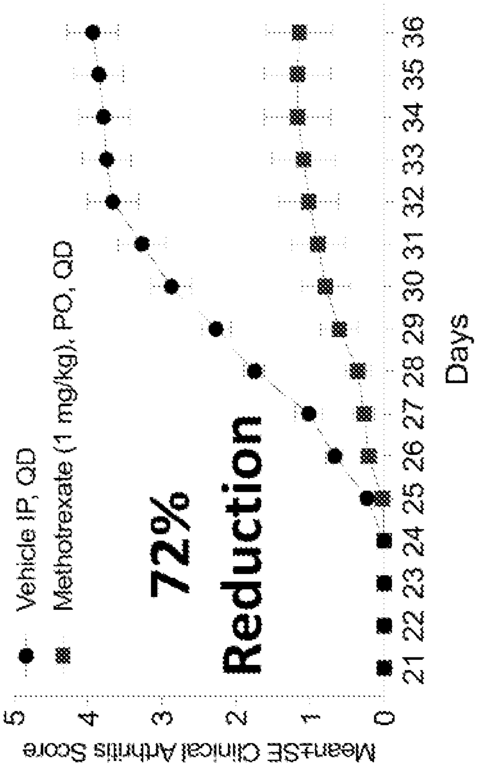
FIG. 4C shows the mean clinical arthritis score over time in the CIA mouse model of inflammatory arthritis for mice (n=12) treated either with vehicle (DMSO, IP, once daily) or methotrexate (1 mg/kg, peroral (PO), once daily). The data show a reduction of only 72% (compared to 85% with compound 5) in clinical arthritis scores for mice treated with methotrexate compared to vehicle treated animals.

FIG. 4C shows the mean clinical arthritis score measured over time in a CIA mouse model of human RA for mice (n=12) treated either with vehicle (DMSO, IP), once daily) or methotrexate (1 mg/kg, peroral (PO), once daily). The data show a reduction of only 72% (compared to 85% with compound 5) in clinical arthritis scores for mice treated with methotrexate compared to vehicle treated animals.

Figure 4D:
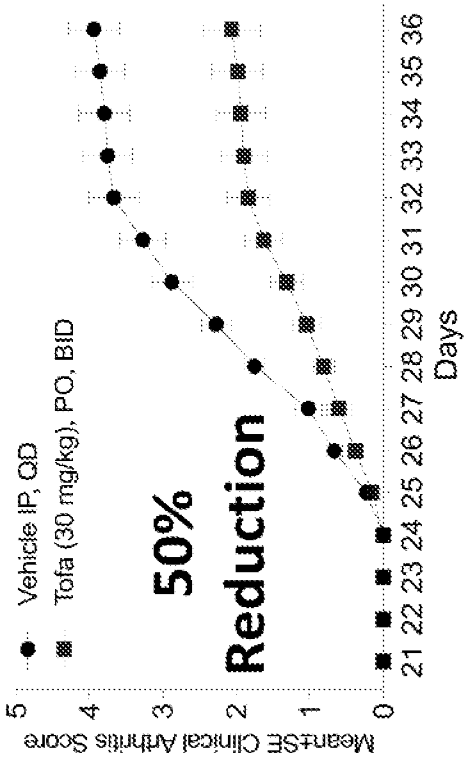
FIG. 4D shows the mean clinical arthritis score over time in the CIA mouse model of inflammatory arthritis for mice (n=12) treated either with vehicle (DMSO, IP, once daily) or the JAK inhibitor tofacitinib ("tofa", 30 mg/kg, peroral (PO), twice daily (BID)). The data show a reduction of only 50% (compared to 85% with compound 5) in clinical arthritis scores for mice treated with tofacitinib compared to vehicle treated animals.

FIG. 4D shows the mean clinical arthritis score measured over time in a CIA mouse model of human RA for mice (n=12) treated either with vehicle (DMSO, IP), once daily) or the JAK inhibitor tofacitinib (30 mg/kg, peroral (PO), twice daily (BID)). The data show a reduction of only 50% (compared to 85% with compound 5) in clinical arthritis scores for mice treated with tofacitinib compared to vehicle treated animals.

Thus, overall, these data demonstrate the superior in vivo performance of the orally bioavailable and selective TAK1 inhibitor compound 5 in a CIA mouse model of human RA over various types of RA frontline treatments, indicating that selective and potent TAK1 inhibition using the compounds of the present disclosure can provide a promising treatment approach for subjects suffering from RA and various other inflammatory, autoimmune, and/chronic diseases.

Oral Administration

In a follow-on study, it was investigated whether, and, if so, to what extend orally administered compound 5 has the ability to be used in anti-TNF refractory RA patients receiving a biological therapeutic, e.g., those patients who had been treated with and were found to be refractory to the biologic etanercept (Enbrel®). To that end, a recently developed pre-clinical model of Enbrel® refractory arthritis was utilized, in which mice develop neutralizing antibodies towards Enbrel® causing disease relapse mirroring patient populations. Using this model, mice (n=6) were initially treated with Enbrel® on days 21-30 until loss of efficacy (determined by an arthritic score of 1.5) around study days 29 to 31 showing the development of neutralizing antibodies and disease progression. At this point, a first treatment group was switched to once daily vehicle (DMSO, PO) from day 30 to day 36, and a second treatment group was switched to twice daily compound 5 (PO).

Figure 4E:
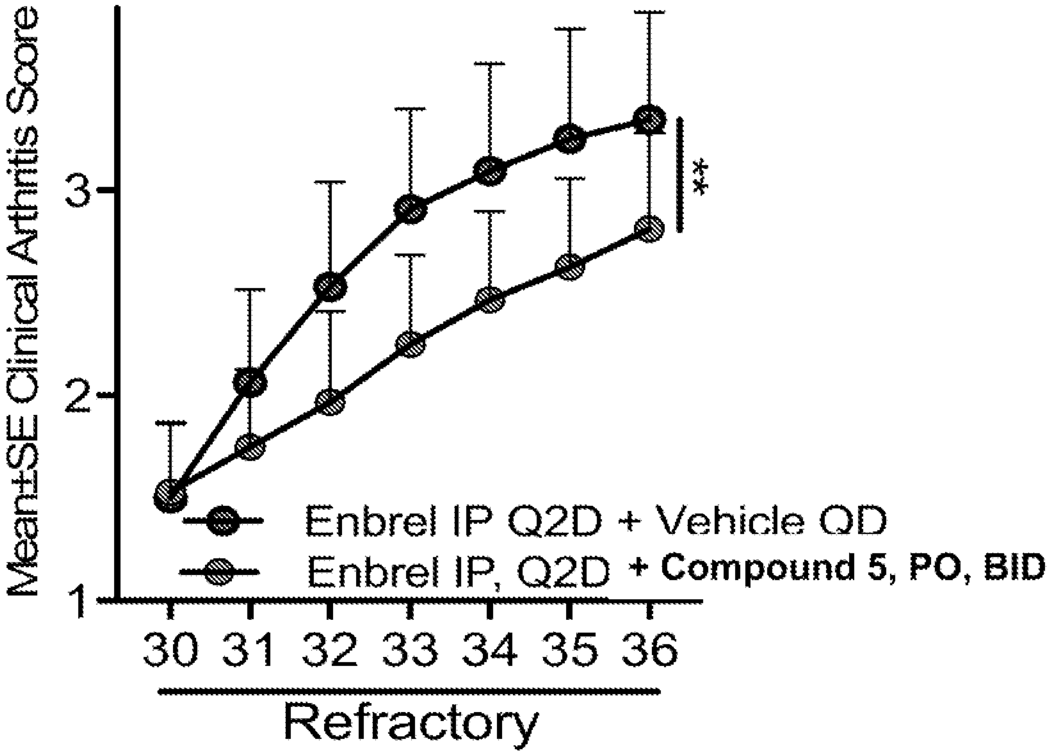
FIG. 4E shows the mean clinical arthritis score as a function of time in a refractory CIA rheumatoid arthritis (RA) mouse model for animals (n=6) treated either with (i) once every other day (Q2D) etanercept (Enbrel®, 10 mg/kg) on days 21-30 and, following development of neutralizing antibodies and disease progression, once daily vehicle (DMSO, PO), or (ii) once every other day (Q2D) etanercept (Enbrel®, 10 mg/kg) on days 21-30 and, following development of neutralizing antibodies and disease progression, twice daily compound 5 (PO). The data show that treatment of etanercept-refractory animals with compound 5 reduced the arthritis score by 40% compared to etanercept-refractory animals that were switched to vehicle.

The data, shown in FIG. 4E, demonstrate that treatment of etanercept-refractory animals with compound 5 reduced the arthritis score by 40% compared to etanercept-refractory animals that were switched to vehicle, suggesting that the orally bioavailable and selective TAK1 inhibitors of the present disclosure can be used to attenuate RA disease in a refractory setting.

Example 11

Evaluation of Parenterally and Orally Administered TAK1 Inhibitors

This example describes experiments comparing the in vivo performance of parenterally (intraperitoneal) and orally (oral gavage) administered TAK1 inhibitor (e.g., compound 5), as well as the safety of orally administered compounds.

In Vivo Efficacy of Orally Administered Compound 5 in Human RA Model

Figure 5A:
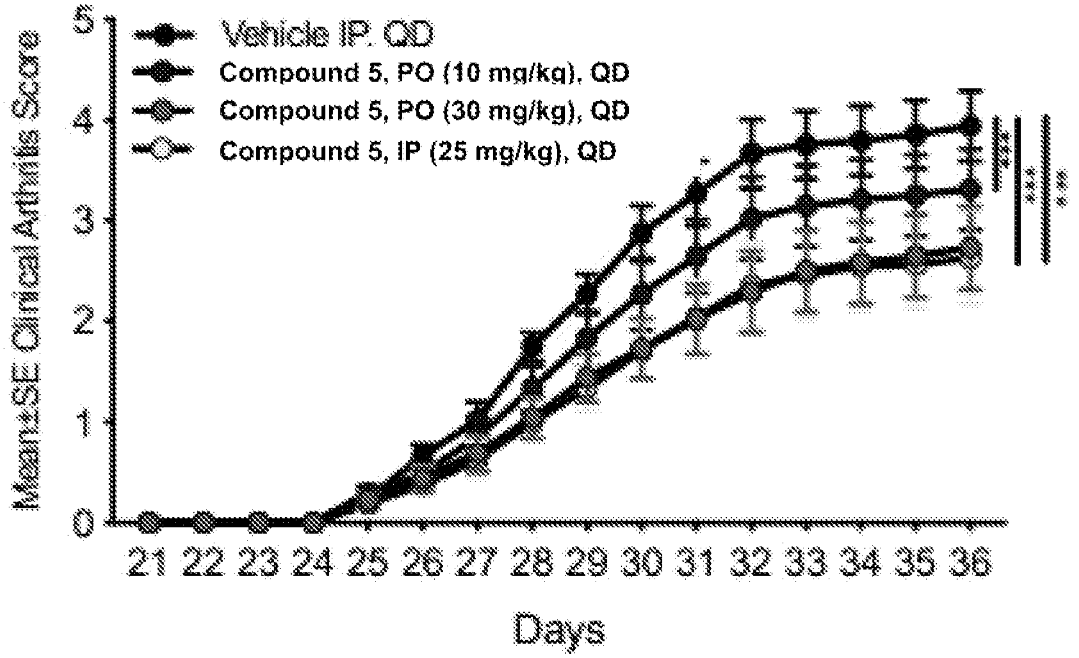
FIG. 5A shows the mean clinical arthritis score as a function of time in the CIA mouse model of inflammatory arthritis for mice treated either with (i) vehicle (DMSO, IP, QD), (ii) compound 5 (10 mg/kg, PO, QD), (iii) compound 5 (30 mg/kg, PO, QD), or (iv) compound 5 (25 mg/kg, IP, QD). The data show that compound 5 reduced the clinical arthritis score by 18% and 35% when orally dosed at 10 and 30 mg/kg, respectively, and thus showed similar efficacy to IP dosing for the 25 mg/kg regimen.
Figure 5B:
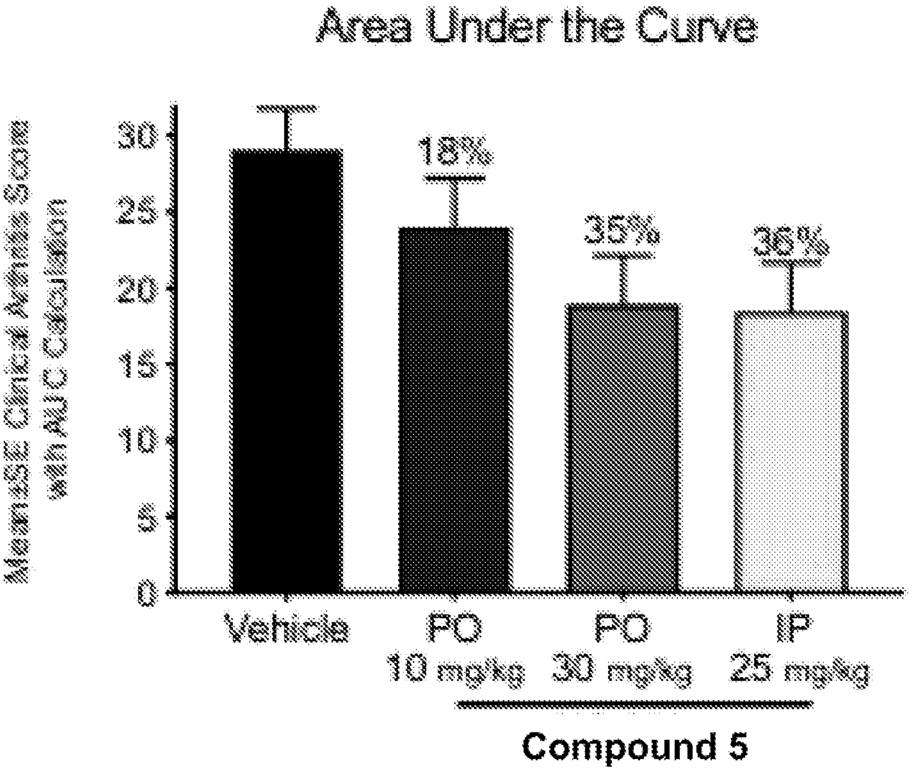
FIG. 5B shows a bar graph illustrating the results of area under the curve (AUC) calculations for the clinical arthritis scores shown in FIG. 5A. The data demonstrate that oral dosing of compound 5 showed similar efficacy to IP dosing with a measured 35% (PO) and 36% (IP) reduction in disease clinical score, respectively.

To that end, following disease onset (around day 21) in a human RA model as previously described, mice were treated with compound 5 at 10 and 30 mg/kg QD PO and 25 mg/kg IP for comparison. The resulting data, shown in FIGS. 5A-5B, demonstrate that compound 5 reduced the clinical arthritis score by 18% and 35% when orally dosed at 10 and 30 mg/kg, respectively, and thus showed similar efficacy to IP dosing for the 30 mg/kg regimen in this disease model.

These in vivo efficacy data were in line with the PK and bioavailability data and demonstrate the oral bioavailability of the compounds of the present disclosure.

Safety of Orally Administered Compound 5

Next, and as further described in EXAMPLE 9, a 14-day toxicology study of orally administered compound 5 in CD-1 mice (n=4) was conducted, using daily oral doses of 5, 30, 50 and 100 mg/kg of compound 5. In this study, the change in body weight from baseline as well as the weight of various organs were measured.

FIG. 6A shows that no weight loss was observed in treated animals compared to the vehicle control group over the course of this study for all treatment groups. Furthermore, no significant differences in blood chemistries or complete blood counts were observed (data not shown). FIGS. 6B-6G also show that daily oral dosing of compound 5 for 14 consecutive days did not cause any significant or dose-dependent changes in relative weight of liver, heart, thymus, kidneys, brain and spleen compared to vehicle.

Taken together, these data demonstrate that the compounds of the present disclosure are orally safe and bioavailable, and were shown to be effective in models of inflammatory arthritis when administered orally.

Example 12

TAK1 Inhibitors in Models of Viral-Induced Pulmonary Hyperinflammation

This example describes the use of TAK1-inhibiting compounds of the present disclosure in a model of viral-induced pulmonary hyperinflammation. Evidence suggests that pharmacological inhibition of TAK1 can profoundly reduce TNF expression in vivo and therefore dampen hyperinflammatory responses. In light of the current SARS-COV-2-induced pandemic, it was investigated whether compounds of the present disclosure can be used to dampen hyperinflammatory responses in patients suffering from COVID-19 by blocking the activation of immune cells mediated by the viral S-protein.

Macrophages stimulated with S-protein can show increased TNF expression as well as enhanced NF-κβ signaling leading to induction of a hyperinflammatory state. Thus, murine bone marrow derived macrophages (BMDMs) were challenged with full length (S1+S2 domain) SARS-CoV-2 spike protein for 24 hours in the presence of compound 5 or vehicle.

Figure 7:
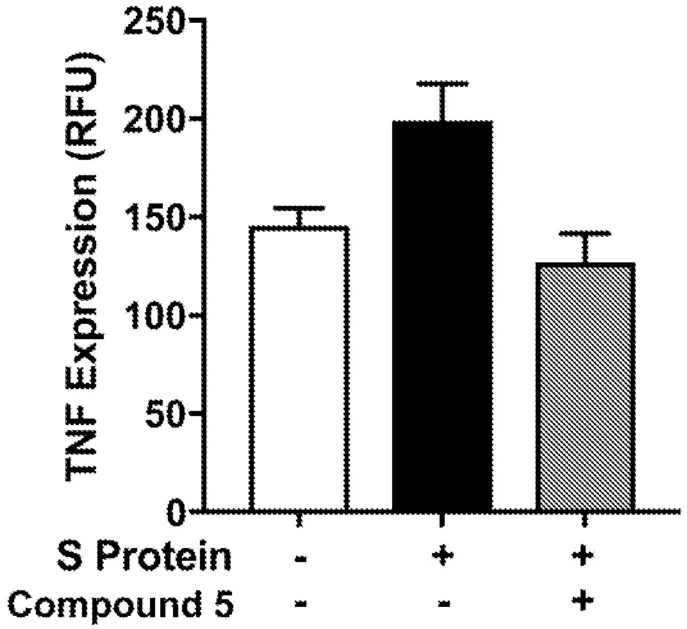
FIG. 7 shows tumor necrosis factor (TNF) expression (in relative fluorescent units (RFU)) in murine bone marrow derived macrophages for the following conditions (n=4): (i) baseline expression (no presence of SARS-CoV-2 spike protein (S-protein) or compound 5), (ii) presence of S-protein (S1+S2 domains) and vehicle, and (iii) presence of S-protein (S1+S2 domains) and compound 5. The data demonstrate the ability of TAK1 inhibitors, such as compound 5, to attenuate S-protein mediated increase in TNF expression.

FIG. 7 shows that selective TAK1 inhibition by compound 5 blocked SARS-CoV-2 spike protein TNF secretion in BMDMs, suggesting that the presently disclosed compounds may be used to reduce hyperinflammation in subjects suffering from viral-induced pulmonary hyperinflammation.

Example 13

Evaluation of TAK1 Inhibitors in Models of Neuropathic Pain

This example describes the use of compounds described herein for treatment of neuropathic/chronic pain in subjects in need thereof.

Is is hypothesized that TAK1 may be a key element in the TNF pro-survival/inflammatory signaling pathway, and that TAK1 may play a crucial role in mediating nuclear factor κβ (NF-κβ) as well as mitogen-activated protein kinases (MAPKs), important targets for inflammation and pain. Moreover, efficacy in chronic neuropathic pain has yet to be clinically demonstrated by anti-TNF biologics, likely due to issues regarding blood-brain barrier (BBB) bioavailability.

Preliminary studies have demonstrated that TAK1 inhibition blocks TNF-mediated neuronal priming. To further evaluate this potential indication, it is tested to what extend orally bioavailable compounds of this disclosure (e.g., compound 5) are capable of crossing the blood-brain barrier (BBB) and bind TAK1 within the central nervous system (CNS).

To that end, and in order to establish efflux of compound 5, MDCK-MDR1 cells are plated in a 96 well plate and allowed to differentiate for 5 days. Drug permeability is determined in both the A→B (Apical to Basolateral) and the B→A (Basolateral to Apical) direction. Following treatment of test article at 10 μM for 2 hours, supernatant from the donor and receiver sides are collected and drug concentration determined by LC-MS/MS. Control molecules ranitidine, and warfarin which have well defined BBB permeability as well as the Pg-P substrate talinolol are also assayed for reference.

Once blood-brain barrier (BBB) bioavailability is established, the compounds (e.g., compounds 5, 9, etc.) are evaluated for their therapeutic potential in various models, such as a monosodium urate-induced arthritis rat model of inflammatory pain, and/or a streptozotocin-induced rat model of diabetic neuropathy (neuropathic pain).

Example 14

Treatment of a TAK1-Mediated Disease or Disorder in a Subject

This example described the treatment of a TAK1-mediated disease or disorder in a subject (e.g., a human).

A pharmaceutical composition comprising a therapeutically effective amount (e.g., between about 1-100 mg/kg) of a TAK1 inhibitor of the present disclosure (e.g., compound 5) is orally administered to a human subject suffering from a TAK1-mediated disease or disorder. The TAK1 inhibitor is orally administered using an appropriate dosage form, such as a tablet or a capsule. The TAK1 inhibitor is administered to the subject once daily for at least 30 consecutive days. Following treatment, the subject shows favorable responses to TAK1 inhibition, including alleviation or abrogation of the disease and at least some of its attendant clinical symptoms.

What is claimed is:

1. A compound according to Formula (I):

(I)

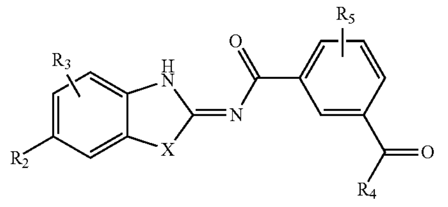

or a pharmaceutically acceptable salt or a tautomer thereof, wherein;

X is $NR_1$;

$R_1$ is H, $C_{1-6}$ alkyl, $C_{1-6}$ carbonyl, $C_{1-6}$ carboxy, substituted or unsubstituted aryl, substituted or unsubstituted heteroaryl, substituted or unsubstituted cyclo $(C_{3-8})$ alkyl, or or substituted or unsubstituted heterocyclo$(C_{3-8})$ alkyl;

$R_2$ is $C_{1-6}$ alkoxy, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo$(C_{3-8})$ alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6;

$R_3$ is H, $C_{1-6}$ alkyl, $C_{1-6}$ alkoxy, halogen, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo$(C_{3-8})$ alkyl, —$NR_8R_9$, $C_{1-6}$ alkyl-$NR_8R_9$, or $C_{1-6}$ alkoxy-$NR_8R_9$, wherein $R_8$ and $R_9$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_8$ and $R_9$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6;

$R_4$ is OH, $C_{1-6}$ alkoxy, $NH_2$, $NH(C_{1-6}$ alkyl), or $N(C_{1-6}$ alkyl) $(C_{1-6}$ alkyl); and $R_5$ is H, $C_{1-6}$ alkyl, $C_{1-6}$ alkoxy, or halogen;

wherein the $C_{1-6}$ alkyl, $C_{1-6}$ alkoxy, $C_{1-6}$ carbonyl and $C_{1-6}$ carboxy of $R_1$, $R_2$, $R_3$, $R_4$, $R_5$, $R_6$, $R_7$, $R_8$, and Ry are optionally and independently substituted by halo, OH, $NH_2$, $NH(C_{1-6}$ alkyl), or $N(C_{1-6}$ alkyl) $(C_{1-6}$ alkyl).

2. The compound of claim 1, wherein $R_4$ is $NH_2$.

3. The compound of claim 1, wherein $R_5$ is H.

4. The compound of claim 1, wherein $R_1$ is H, $C_{1-6}$ alkyl, or substituted or unsubstitued cyclo$(C_{3-8})$ alkyl.

5. The compound of claim 1, wherein Ri is $C_{1-6}$ alkyl or substituted cyclohexyl.

6. The compound of claim 1, wherein $R_3$ is H.

7. The compound of claim 1, wherein $R_2$ is substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo$(C_{3-8})$ alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6.

8. The compound of claim 1, wherein $R_2$ is —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring.

9. The compound of claim 1, wherein $R_2$ is —$CH_2$—N $(C_{1-6}$ alkyl) $(C_{1-6}$ alkyl) or —$CH_2$—$NR_6R_7$, wherein $R_6$ and $R_7$ are combined with the nitrogen atom to form a 5-, 6-, 7- or 8-membered, substituted or unsubstituted heterocycloalkane or substituted or unsubstituted heteroaromatic ring.

10. The compound of claim 1, wherein $R_2$ is —$CH_2$—$NR_6R_7$, wherein $R_6$ and $R_7$ are combined with the nitrogen atom to form a 5- or 6-membered, substituted or unsubstituted heterocycloalkane or substituted or unsubstituted heteroaromatic ring.

11. The compound of claim 1, wherein $R_2$ is —$CH_2$—$NR_6R_7$, wherein $R_6$ and $R_7$ are combined with the nitrogen atom to form a 6-membered, substituted or unsubstituted heterocycloalkane ring.

12. The compound of claim 1, wherein $R_2$ is substituted or unsubstituted piperidinomethyl.

13. The compound of claim 1, wherein the compound according to Formula (I) is selected from the group consisting of:

5

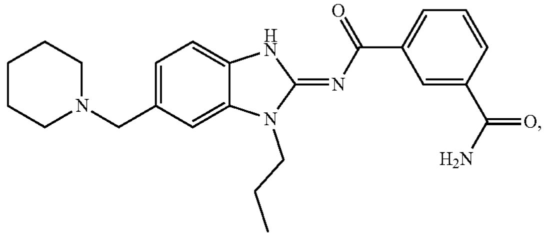

-continued

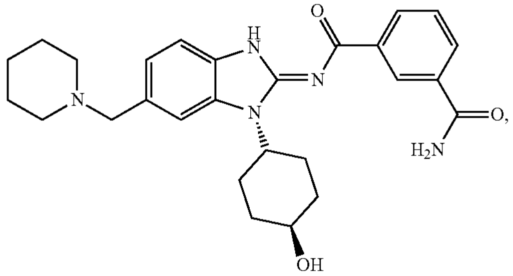

, and

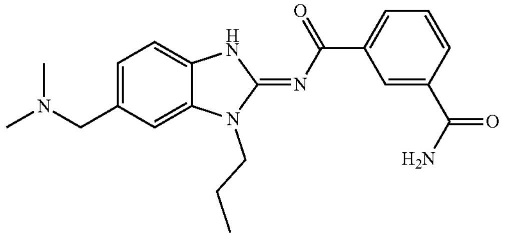

or a pharmaceutically acceptable salt, a tautomer, or a prodrug thereof.

14. The compound of claim 1, wherein the compound according to Formula (I) is:

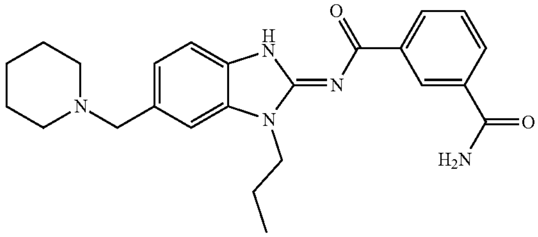

or a pharmaceutically acceptable salt, a tautomer, or a prodrug thereof.

15. A pharmaceutical composition comprising a compound according to claim 1, and a pharmaceutically acceptable carrier or excipient.

16. The compound of claim 1, wherein the compound has a ratio of $IC_{50}$ (IRAK) to $IC_{50}$ (TAK1) of at least about 25.

17. A method of treating chronic pain in a subject in need thereof, the method comprising administering to the subject a pharmaceutical composition comprising an effective amount of a compound according to Formula (I):

(I)

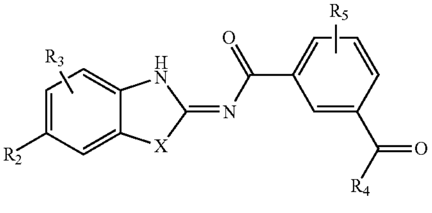

or a pharmaceutically acceptable salt or a tautomer thereof, wherein;

X is $NR_1$;

$R_1$ is H, $C_{1-6}$ alkyl, $C_{1-6}$ carbonyl, $C_{1-6}$ carboxy, substituted or unsubstituted aryl, substituted or unsubstituted heteroaryl, substituted or unsubstituted cyclo ($C_{3-8}$) alkyl, or or substituted or unsubstituted heterocyclo($C_{3-8}$) alkyl;

$R_2$ is $C_{1-6}$ alkyl, $C_{1-6}$ alkoxy, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_6R_7$, $C_{1-6}$ alkyl-$NR_6R_7$, or $C_{1-6}$ alkoxy-$NR_6R_7$, wherein $R_6$ and $R_7$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_6$ and $R_7$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6;

$R_3$ is H, $C_{1-6}$ alkyl, $C_{1-6}$ alkoxy, halogen, substituted or unsubstituted —Y—$(CH_2)_n$-aryl, substituted or unsubstituted —Y—$(CH_2)_n$-heteroaryl, substituted or unsubstituted —Y—$(CH_2)_n$-cyclo($C_{3-8}$) alkyl, —$NR_8R_9$, $C_{1-6}$ alkyl-$NR_8R_9$, or $C_{1-6}$ alkoxy-$NR_8R_9$, wherein $R_8$ and $R_9$ are independently selected from the group consisting of H, $C_{1-6}$ alkyl, hetero-$C_{1-6}$ alkyl, substituted or unsubstituted aryl and substituted or unsubstituted aryl-$C_{1-6}$ alkyl; alternatively, $R_8$ and $R_9$ may be combined with the nitrogen atom to form a 5-, 6-, 7- or 8-membered, substituted or unsubstituted heterocycloalkane or substituted or unsubstituted heteroaromatic ring, wherein Y is selected from the group consisting of a bond, O and S, and wherein the subscript n is an integer from 0 to 6;

$R_4$ is OH, $C_{1-6}$ alkoxy, $NH_2$, NH($C_{1-6}$ alkyl), or N($C_{1-6}$ alkyl) ($C_{1-6}$ alkyl); and $R_5$ is H, $C_{1-6}$ alkyl, $C_{1-6}$ alkoxy, or halogen;

wherein the $C_{1-6}$ alkyl, $C_{1-6}$ alkoxy, $C_{1-6}$ carbonyl and $C_{1-6}$ carboxy of $R_1$, $R_2$, $R_3$, $R_4$, $R_5$, $R_6$, $R_7$, $R_8$, and Ry are optionally and independently substituted by halo, OH, $NH_2$, NH($C_{1-6}$ alkyl), or N($C_{1-6}$ alkyl) ($C_{1-6}$ alkyl).

18. The method of claim 17, wherein the compound has a ratio of $IC_{50}$ (IRAK) to $IC_{50}$ (TAK1) of at least about 25, 50, 100, 500, 1,000 or 2,000.

19. The method of claim 17, wherein the compound has a blood plasma concentration of at least about 0.25, 0.5, 1.0, or 1.5 μM measured 2 hours after oral administration of 50 mg/kg of the compound to a subject.

20. The method of claim 17, wherein the subject is treatment refractory to a previously administered anti-inflammatory agent and wherein the anti-inflammatory agent is an anti-TNF biologic.

* * * * *